(12) United States Patent
Duvall et al.

(10) Patent No.: US 10,172,956 B2
(45) Date of Patent: Jan. 8, 2019

(54) POLYMERIC NANOPARTICLES

(71) Applicant: Vanderbilt University, Nashville, TN (US)

(72) Inventors: Craig L. Duvall, Nashville, TN (US); Christopher E. Nelson, Nashville, TN (US); James Kintzing, Nashville, TN (US); Joshua M. Shannon, Nashville, TN (US); Mukesh K. Gupta, Nashville, TN (US); Scott A. Guelcher, Thompsons Station, TN (US); Elizabeth J. Adolph, Nashville, TN (US); Jeffrey M. Davidson, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 14/438,596

(22) PCT Filed: Oct. 28, 2013

(86) PCT No.: PCT/US2013/067149
§ 371 (c)(1),
(2) Date: Apr. 24, 2015

(87) PCT Pub. No.: WO2014/066912
PCT Pub. Date: May 1, 2014

(65) Prior Publication Data
US 2015/0283254 A1   Oct. 8, 2015

Related U.S. Application Data

(60) Provisional application No. 61/719,276, filed on Oct. 26, 2012.

(51) Int. Cl.
| | |
|---|---|
| *C07H 21/04* | (2006.01) |
| *A61K 47/48* | (2006.01) |
| *C12N 15/88* | (2006.01) |
| *A61K 48/00* | (2006.01) |
| *C08F 283/06* | (2006.01) |
| *C12N 15/113* | (2010.01) |
| *C08J 3/12* | (2006.01) |
| *A61K 9/51* | (2006.01) |

(52) U.S. Cl.
CPC ...... *A61K 47/489* (2013.01); *A61K 47/48176* (2013.01); *A61K 47/48215* (2013.01); *A61K 47/48869* (2013.01); *A61K 48/00* (2013.01); *C08F 283/06* (2013.01); *C08J 3/126* (2013.01); *C12N 15/113* (2013.01); *C12N 15/88* (2013.01); *A61K 9/5138* (2013.01); *A61K 48/0041* (2013.01); *C08F 2438/03* (2013.01); *C08J 2353/00* (2013.01); *C12N 15/1137* (2013.01); *C12N 2310/14* (2013.01); *C12N 2310/351* (2013.01); *C12N 2320/30* (2013.01); *C12Y 502/01008* (2013.01)

(58) Field of Classification Search
None
See application file for complete search history.

(56) References Cited

U.S. PATENT DOCUMENTS

| | | |
|---|---|---|
| 6,312,727 B1 | 11/2001 | Schacht et al. |
| 2009/0156459 A1 | 6/2009 | Castillo et al. |
| 2011/0052917 A1 | 3/2011 | Kataoka et al. |
| 2011/0123636 A1* | 5/2011 | Stayton ................ A61K 9/1075 424/497 |
| 2015/0231302 A1 | 8/2015 | Duvall et al. |

FOREIGN PATENT DOCUMENTS

WO   2009140421   11/2009

OTHER PUBLICATIONS

Aliabadi et al. ("Single and combinational siRNA therapy of cancer cells: probing changes in targeted and nontargeted mediators after siRNA treatment." Molecular pharmaceutics 13. 12 (2016): 4116-4128).*
Verbaan, F. J.; Oussoren, C.; van Dam, I. M.; Takakura, Y.; Hashida, M.; Crommelin, D. J.; Hennink, W. E.; Storm, G., The Fate of Poly(2-Dimethyl Amino Ethyl)Methacrylate-Based Polyplexes after Intravenous Administration. Int J Pharm 2001, 214, 99-101.
Petersen, H.; Fechner, P. M.; Martin, A. L.; Kunath, K.; Stolnik, S.; Roberts, C. J.; Fischer, D.; Davies, M. C.; Kissel, T., Polyethylenimine-Graft-Poly(Ethylene Glycol) Copolymers: Influence of Copolymer Block Structure on DNA Complexation and Biological Activities as Gene Delivery System. Bioconjugate Chem 2002, 13, 845-854.
Rungsardthong, U.; Deshpande, M.; Bailey, L.; Vamvakaki, M.; Armes, S. P.; Garnett, M. C.; Stolnik, S., Copolymers of Amine Methacrylate with Poly(Ethylene Glycol) as Vectors for Gene Therapy. J Control Release 2001, 73, 359-80.

(Continued)

*Primary Examiner* — Kimberly Chong
(74) *Attorney, Agent, or Firm* — Stites & Harbison PLLC; Sean P. Ritchie; Richard S. Myers, Jr.

(57) ABSTRACT

The presently-disclosed subject matter includes nanoparticles that comprise a plurality of assembled polymers. In some embodiments the polymers comprise a first block that includes hydrophilic monomers, the first block substantially forming an outer shell of the nanoparticle, and a second block that includes cationic monomers and hydrophobic monomers, the second block substantially forming a core of the nanoparticle. In some embodiments a polynucleotide is provided that is bound to the cationic monomers of the nanoparticle. The presently-disclosed subject matter also comprises methods for using the present nanoparticles to include RNAi in a cell as well as methods for making the present nanoparticles.

35 Claims, 28 Drawing Sheets

(56) References Cited

OTHER PUBLICATIONS

Venkataraman, S.; Ong, W. L.; Ong, Z. Y.; Joachim Loo, S. C.; Ee, P. L.; Yang, Y. Y., The Role of Peg Architecture and Molecular Weight in the Gene Transfection Performance of Pegylated Poly(Dimethylaminoethyl Methacrylate) Based Cationic Polymers. Biomaterials 2011, 32, 2369-78.
Sato, A.; Choi, S. W.; Hirai, M.; Yamayoshi, A.; Moriyarna, R.; Yamano, T.; Takagi, M.; Kano, A.; Shimamoto, A.; Maruyama, A., Polymer Brush-Stabilized Polyplex for a Sirna Carrier with Long Circulatory Half-Life. Journal of Controlled Release 2007, 122, 209-216.
Verbaan, F. J.; Oussoren, C.; Snel, C. J.; Crommelin, D. J.; Hennink, W. E.; Storm, G., Steric Stabilization of Poly(2-Dimethylamino)Ethyl Methacrylate)-Based Polyplexes Mediates Prolonged Circulation and Tumor Targeting in Mice. J Gene Med 2004, 6, 64-75.
Glodde, M.; Sirsi, S. R.; Lutz, G. J., Physiochemical Properties of Low and High Molecular Weight Poly(Ethylene Glycol)-Grafted Poly(Ethylene Imine) Copolymers and Their Complexes with Oligonucleotides. Biomacromolecules 2006, 7, 347-356.
Itaka, K.; Yamauchi, K.; Harada, A.; Nakamura, K.; Kawaguchi, H.; Kataoka, K., Polyion Complex Micelles from Plasmid DNA and Poly(Ethylene Glycol)-Poly(L-Lysine) Block Copolymer as Serum-Tolerable Polyplex System: Physicochemical Properties of Micelles Relevant to Gene Transfection Efficiency. Biomaterials 2003, 24, 4495-506.
Luo, D.; Haverstick, K.; Belcheva, N.; Han, E.; Saltzman, W. M., Poly(Ethylene Glycol)-Conjugated Pamam Dendrimer for Biocompatible, High-Efficiency DNA Delivery. Macromolecules 2002, 35, 3456-3462.
Lee H.; Jeong, J. H.; Park, T. G. A New Gene Delivery Formulation of Polyethylenimine/DNA Complexes Coated with Peg Conjugated Fusogenic Peptide. J Control Release 2001, 76, 183-92.
Convertine, A. J.; Benoit, D. S. W.; Duvall, C. L.; Hoffman, A. S.; Stayton, P. S., Development of a Novel Endosomolytic Diblock Copolymer for Sirna Delivery. Journal of Controlled Release 2009, 133, 221-229.
Duvall, C. L.; Convertine, A. J.; Benoit, D. S.; Hoffman, A. S.; Stayton, P. S., Intracellular Delivery of a Proapoptotic Peptide Via Conjugation to a Raft Synthesized Endosomolytic Polymer. Mol Pharm 2010, 7, 468-76.
Convertine, A. J.; Diab, C.; Prieve, M.; Paschal, A.; Hoffman, A. S.; Johnson, P. H.; Stayton, P. S., Ph-Responsive Polymeric Micelle Carriers for Sirna Drugs. Biomacromolecules 2010.
Manganiello, M. J.; Cheng, C.; Convertine, A. J.; Bryers, J. D.; Stayton, P. S., Diblock Copolymers with Tunable Ph Transitions for Gene Delivery. Biomaterials 2012, 33, 2301-9.
Cheng, C.; Convertine, A. J.; Stayton, P. S.; Bryers, J. D., Multifunctional Triblock Copolymers for Intracellular Messenger Rna Delivery. Biomaterials 2012, 33, 6868-6876.
Gary, D. J.; Lee, H.; Sharma, R.; Lee, J. S.; Kim, Y.; Cui, Z. Y.; Jia, D.; Bowman, V. D.; Chipman, P. R.; Wan, L., et al., Influence of Nano-Carrier Architecture on in Vitro Sirna Delivery Performance and in Vivo Biodistribution: Polyplexes Vs Micelleplexes. ACS Nano 2011, 5, 3493-505.
Xiao, K.; Li, Y.; Luo, J.; Lee, J. S.; Xiao, W.; Gonik, A. M.; Agarwal, R. G.; Lam, K S., The Effect of Surface Charge on in Vivo Biodistribution of Peg-Oligocholic Acid Based Micellar Nanoparticles. Biomaterials 2011, 32, 3435-46.
Zuckerman, J. E.; Choi, C. H. J.; Han, H.; Davis, M. E., Polycation-Sirna Nanoparticles Can Disassemble at the Kidney Glomerular Basement Membrane. P Natl Acad Sci USA 2012, 109, 3137-3142.
Naeye, B.; Deschout, H.; Caveliers, V.; Descamps, B.; Braeckmans, K; Vanhove, C.; Demeester, J.; Lahoutte, T.; De Smedt, S. C.; Raemdonck, K., In Vivo Disassembly of Iv Administered Sirna Matrix Nanoparticles at the Renal Filtration Barrier. Biomaterials 2013, 34, 2350-2358.
Boussif, O.; Lezoualc'h, F.; Zanta, M. A.; Mergny, M. D.; Scherman, D.; Demeneix, B.; Behr, J. P., A versatile vector for gene and oligonucleotide transfer into cells in culture and in vivo: polyethylenimine. Proc Natl Acad Sci U S A 1995, 92, (16), 7297-301.
Kichler, A.; Chillon, M.; Leborgne, C.; Danos, O.; Frisch, B., Intranasal gene delivery with a polyethylenimine-PEG conjugate. J Control Release 2002, 81, (3), 379-88.
Piest, M.; Engbersen, J. F. J., Effects of charge density and hydrophobicity of poly(amido amine)s for non-viral gene delivery. Journal of Controlled Release 2010, 148, (1), 83-90.
Ogris, M.; Brunner, S.; Schuller, S.; Kircheis, R.; Wagner, E., PEGylated DNA/transferrin-PEI complexes: reduced interaction with blood components, extended circulation in blood and potential for systemic gene delivery. Gene Ther 1999, 6, (4), 595-605.
Sharma, R.; Lee, J. S.; Bettencourt, R. C.; Xiao, C.; Konieczny, S. F.; Won, Y. Y., Effects of the incorporation of a hydrophobic middle block into a PEG-polycation diblock copolymer on the physicochemical and cell interaction properties of the polymer-DNA complexes. Biomacromolecules 2008, 9, (11), 3294-307.

* cited by examiner

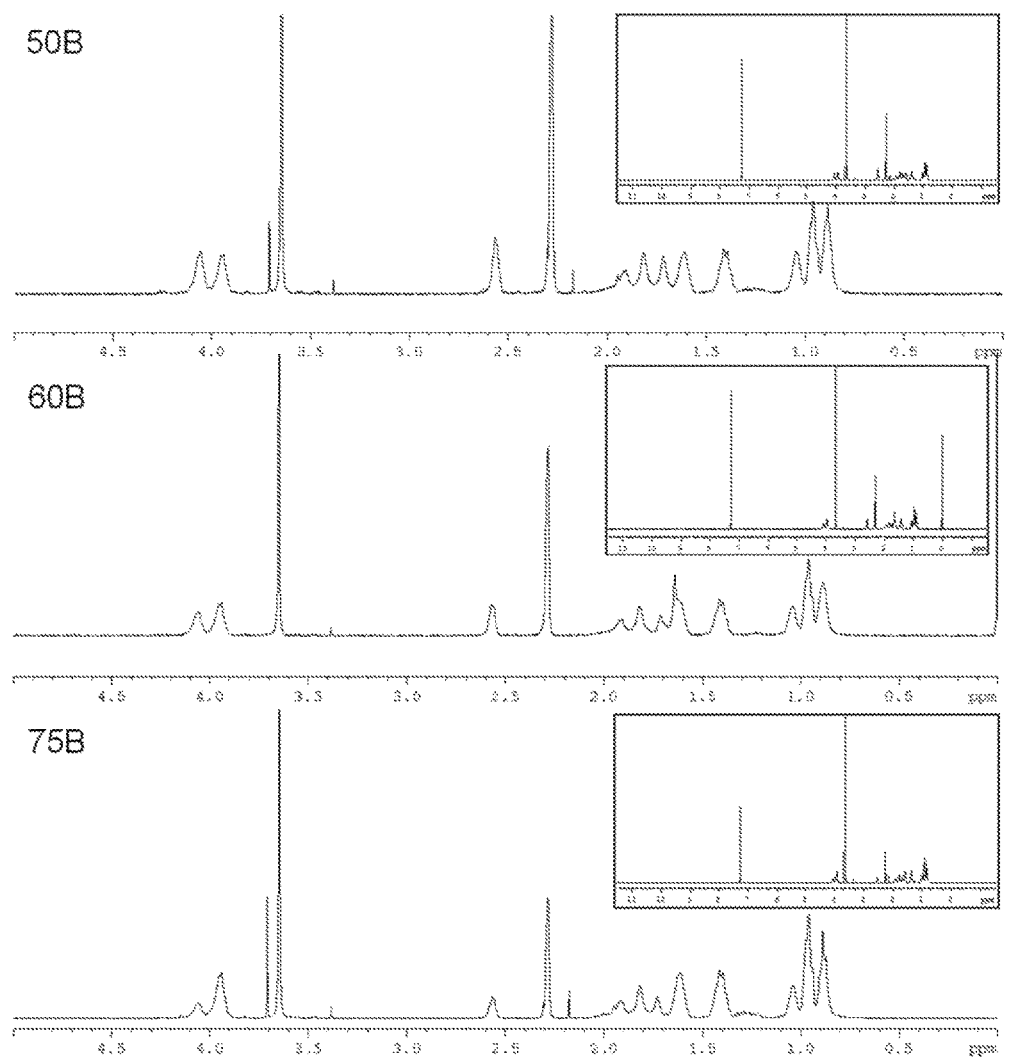
Figure 2 con't

40B

50B

POLYMERIC NANOPARTICLES

RELATED APPLICATIONS

This application claims priority from International Patent Application No. PCT/US2013/67149, filed Oct. 28, 2013, which claims priority from U.S. Provisional Application Ser. No. 61/719,276, filed Oct. 26, 2012, the entire disclosures of which are incorporated herein by this reference.

GOVERNMENT INTEREST

This invention was made with government support under Grant Number DMR-1005023 awarded by the National Science Foundation and Grant Numbers 5R01AR056138-02 and R21EB012750 awarded by the National Institutes of Health. The government has certain rights in the invention.

TECHNICAL FIELD

The presently-disclosed subject matter relates to nanoparticles. In particular, embodiments of the presently-disclosed subject matter relate to pH-responsive, polymeric nanoparticles for the delivery of biologically active agents.

INTRODUCTION

The discovery of RNA interference (RNAi) has motivated extensive efforts toward harnessing gene-silencing biomacromolecules for clinical therapeutic use. Small-interfering RNA (siRNA) have advanced into clinical trials for indications such as macular degeneration, skin disorders, and targeted delivery to melanoma. However, effective delivery has been a limitation to more rapid and widespread adoption of siRNA for clinical use due to its poor filtration and aggregating, susceptibility to enzymes, such as nucleases, poor membrane permeability, and poor intracellular cytosolic delivery.

To address these issues, a variety of strategies have attempted to protect siRNA and improve intracellular delivery including electrostatic complexation with cationic lipids, polymers, and polysacccharides, as well as conjugation to cell-penetrating/fusogenic peptides, dendrimers, antibodies, vitamins, and nanoparticles, but these previous strategies all have shortcomings. For example, intravenous administration of cationic lipoplexes or nanoparticles, which is desirable for many therapeutic applications, often results in particle instability and nonspecific interactions with blood components that induce opsonization, aggregation of red blood cells, platelet activation, excessive biodistribution to the lungs, and, in extreme cases, rapid mortality. Furthermore, these materials generally lack tunability, particularly with regard to release kinetics, and have been limited to rapid burst release of siRNA, and other known materials requires complex equipment (e.g., electrospinning apparatus) to prefabricate materials to a defined size and geometry. Other known polymer siRNA carriers are unsuitable due to cytotoxicity.

Similarly, nonviral gene therapy has potential for use in tissue restoration and treatment of myriad diseases. Plasmids (pDNA) production is efficient, and DNA therapy limits the immunogenic risk of viral vectors. Naked pDNA uptake and utilization is inefficient; however, efficient synthetic plasmid carriers face several in vivo challenges that have impeded the development of efficient and nontoxic nonviral options for pDNA delivery.

Accordingly, there remains a need for improved compositions and methods for delivery of polynucleic acids, such as siRNA, that meet these and other long-felt needs.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

Embodiments of the presently-disclosed subject matter include a nanoparticle comprising a plurality of polymers. In some embodiments the polymer includes a first block and a second block. In some embodiments the first block includes hydrophilic monomers, and the first block substantially forms an outer shell of the nanoparticle. In some embodiments the second block includes cationic monomers and hydrophobic monomers, and the second block substantially forms a core of the nanoparticle. Exemplary nanoparticles can further comprise a polynucleotide that is bound to the cationic monomers.

The hydrophilic monomers in some embodiments can include ethylene glycol (EG) monomers, and in specific embodiments the ethylene glycol (EG) monomers can form a poly(ethylene glycol) including a molecular weight of about 500 Da to about 20,000 Da.

In some embodiments the cationic monomers are cationic at about pH 7.0, at about endosomal pH, or a combination thereof. In some embodiments the cationic monomers have a greater cationic charge below about pH 7.0 than at about pH 7.0. In this regard, exemplary cationic monomers include N,N-di($C_1$-$C_6$)alkyl-amino($C_1$-$C_6$)alkyl-ethacrylate, N,N-di($C_1$-$C_6$)alkyl-amino($C_1$-$C_6$)alkyl-methacrylate, N,N-di($C_1$-$C_6$)alkyl-amino($C_1$-$C_6$)alkyl-acrylate, or combinations thereof. In specific embodiments the cationic monomers include 2-(dimethylamino)ethyl methacrylate (DMAEMA).

In some embodiments the hydrophobic monomers include ($C_2$-$C_8$)alkyl-ethacrylate, ($C_2$-$C_8$)alkyl-methacrylate, ($C_2$-$C_8$)alkyl-acrylate, or combinations thereof. In specific embodiments the hydrophobic monomer includes butyl methacrylate (BMA).

In some embodiments the polynucleotide of the nanoparticles is electrostatically bound to at least one of the cationic monomers. Exemplary polynucleotides can induce RNAi. The polynucleotides can include siRNA.

The nanoparticles can comprise an assembly of the plurality of polymers. That said, in some embodiments the plurality of polymers can at least partially disassemble at a pH below about pH 7.0, at below about pH 6.0, at below pH 5.5, or the like. Furthermore, the polymers that comprise a nanoparticle can include a polydispersity of about less than 1.10 and/or the polymers can include a polydispersity of about less than 1.05.

In some embodiments of nanoparticles, the second block of the polymers is itself a diblock copolymer. In certain embodiments the diblock copolymer includes a cationic block and a hydrophobic block, where the cationic block includes the cationic monomers, and the hydrophobic block includes the hydrophobic monomers. In some embodiments, the second block is configured such that the hydrophobic block of the second block links the first block to the cationic block of the second block (i.e., hydrophobic block is disposed between the first block that includes the hydrophilic monomers and the cationic block of the second block).

The second block can have various concentrations of hydrophobic monomer relative to cationic monomer. In some embodiments the second block comprises about 5 mol % to about 75 mol % of the hydrophobic monomer. In some embodiments the second block comprises about 10 mol % to about 60 mol % of the hydrophobic monomer. In some embodiments the second block comprises about 25 mol % to about 50 mol % of the hydrophobic monomer.

The nanoparticles can also comprise different concentrations of cationic monomer to polynucleotide. In some embodiments this concentration is measured as a ratio of cationic charge of the cationic monomers to the anionic charge of the polynucleotides, which can be referred to herein as an N:P ratio. In some embodiments a nanoparticle can comprise a N:P ratio of about 0.5 to about 20. In other embodiments the nanoparticle can comprise a N:P ratio of about 1 to about 10.

Exemplary nanoparticles can be measured on a nanoscale. In this regard, certain nanoparticles can comprise a diameter (e.g., hydrodynamic diameter) of about 10 nm to about 100 nm.

In certain embodiments the second block consists essentially of the cationic block that includes the cationic monomers and the hydrophobic block that includes the hydrophobic monomers. In some embodiments the second block consists of the cationic block that includes the cationic monomers and the hydrophobic block that includes the hydrophobic monomers. In other embodiments the polymers consist essentially of or consist of the first block and the second block. In some embodiments the polymers do not comprise a block in addition to the first block and the second block. In yet further embodiments the polymers to do not comprise an alkyl-acrylic acid monomer.

The presently-disclosed subject matter further includes methods for inducing RNAi in a cell. Exemplary methods can comprise contacting a nanoparticle to the cell. The nanoparticle can include a plurality of polymers each comprising a first block that includes hydrophilic monomers, the first block substantially forming an outer shell of the nanoparticle, and a second block that includes cationic monomers and hydrophobic monomers, the second block substantially forming a core of the nanoparticle, and the nanoparticles can further include a polynucleotide that is bound to the cationic monomers, the polynucleotide being capable of inducing RNAi in the cell. Any of the nanoparticles described herein can be utilized for inducing RNAi in a cell.

In some embodiments the polynucleotide is capable of inhibiting proliferation of the cell. In exemplary embodiments the cell is a cancer cell. In this regard, the presently-disclosed subject matter can further include treating cancer in a subject in need thereof by administering the nanoparticle to the subject, the nanoparticles then being capable of contacting cancer cells in the subject.

The presently-disclosed subject matter further includes a method for making a nanoparticle. Exemplary methods include providing a plurality of polymers in a solution, the polymers including a first block that includes hydrophilic monomers and a second block that includes cationic monomers and hydrophobic monomers, adjusting a pH of the solution to a low pH (e.g., less than about pH 7.0), adding a polynucleotide to the solution and allowing the polynucleotide to bind to the cationic monomers, and raising the pH of the solution to a high pH (e.g., at least about pH 7.0) to form the nanoparticle. The resulting nanoparticle can include the first block that substantially forms an outer shell of the nanoparticle and the second block that substantially forms a core of the nanoparticle. In some embodiments the step of adjusting the pH of the solution to a low pH (e.g., less than about pH 7.0) includes adjusting the pH to a value of about pH 4.0 to about pH 6.0.

Further features and advantages of the present presently-disclosed subject matter will become evident to those of ordinary skill in the art after a study of the present application.

DESCRIPTION OF EXEMPLARY EMBODIMENTS

Figure 1:
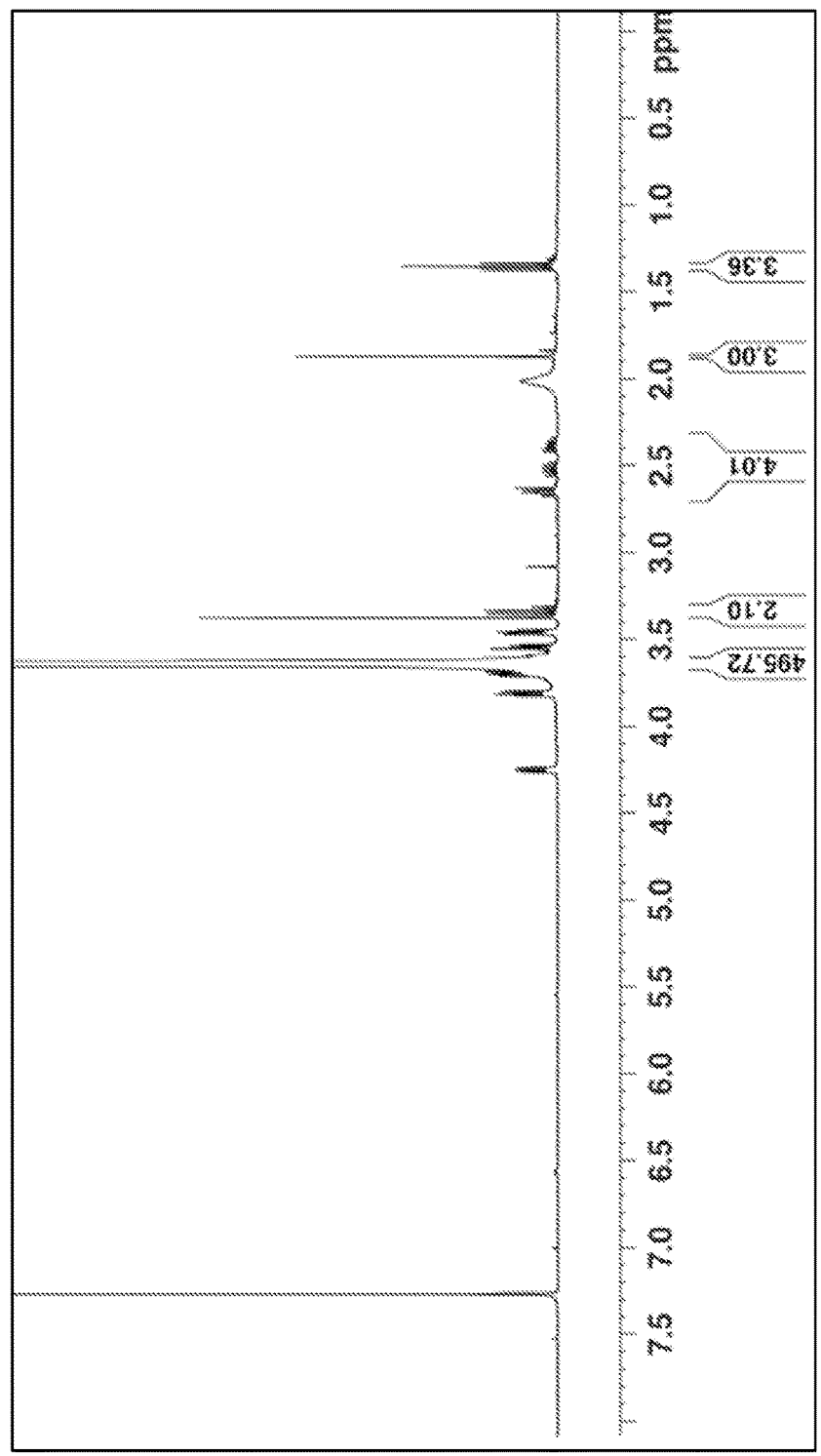
FIG. 1 includes a plot showing integration of the $\delta$ 1.88 s ($CCNCH_3$) ECT peak and the 3.65 s ($—OCH_2CH_2—$) PEG peak revealing the percent conjugation thereof.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes nanoparticles that can deliver active agents to cells. In particular, the presently-disclosed subject matter includes nanoparticles that can deliver polynucleotides to cells. In some embodiments the nanoparticles include polymeric nanoparticles that are formed by a plurality of assembled polymers. In some embodiments the nanoparticles are cytocompatible such that they are minimally or wholly non-toxic when administered to a subject and/or to a sample of cells. Exemplary nanoparticles can also be pH-responsive such that at a particular pH and/or range of pH the nanoparticles deliver the active agent they carry, disrupt membranes, or a combination thereof. In some embodiments this pH-responsive characteristic can be utilized to achieve endosomal escape of the nanoparticles and/or the active agents to achieve delivery to the cytosol. Furthermore, in some embodiments the present nanoparticles are stable, including some embodiments of nanoparticles that are stable in the blood of subject, thereby enhancing the circulation time and/or biodistribution of the present nanoparticles within a sample and/or within a subject.

In particular embodiments of the present nanoparticles, the nanoparticles can comprise a plurality of polymers that include: (i) a first block that includes hydrophilic monomers, the first block substantially forming an outer shell of the nanoparticle, and (ii) a second block that includes cationic monomers and hydrophobic monomers, the second block substantially forming a core of the nanoparticle. The nanoparticles can further comprise a polynucleotide that serves as an active agent that is bound to the cationic monomers of the second block.

The term "nanoparticle" as used herein, refers to particles that generally can be measured on a nanometer scale and, for example, may be about 1 nm to about 999 nm in diameter. In some embodiments nanoparticles include particles that include a diameter of less than about 500 nm. In this regard, as used herein the diameter of the nanoparticles can refer to the hydrodynamic diameter of the nanoparticles. Accordingly, nanoparticle is a term that can be used to describe the characteristics, and particularly the size, of a particle. Nanoparticle is also inclusive of micelles that can be measured on a nanoscale, including polymeric micelles that includes polymers having a hydrophobic end and a hydrophilic end, and wherein the hydrophobic ends of the polymers form a core of the nanoparticle and the hydrophilic ends of the polymers form an outer shell (i.e., corona) of the nanoparticle.

Polymer

In some embodiments the polymers that form the nanoparticles include at least two blocks, which are referred to herein as a first block and a second block. Furthermore, each of the first block and/or the second block can be copolymers of one or more monomer species. The term "copolymer", as used herein, refers to a polymer comprising two or more different monomers.

In some embodiments of the polymer, the polymer is a block copolymer. Furthermore, in some embodiments the second block of the polymer is a block copolymer. A "block" copolymer refers to a structure comprising one or more sub-combination of constitutional or monomeric units. In some embodiments, constitutional units are derived via additional processes from one or more polymerizable monomers. In some embodiments, the block copolymer is a diblock copolymer. A diblock copolymer comprises two blocks; a schematic generalization of such a polymer is represented by the following: $[A_aB_b \ldots ]_m\text{-}[X_xY_y \ldots ]_n$, wherein each letter stands for a constitutional or monomeric unit, and wherein each subscript to a constitutional unit represents the mole fraction of that unit in the particular block, the three dots indicate that there may be more (there may also be fewer) constitutional units in each block and m and n indicate the molecular weight of each block in the diblock copolymer. In some instances, the number and the nature of each constitutional unit is separately controlled for each block. The schematic is not meant and should not be construed to infer any relationship whatsoever between the number of constitutional units or the number of different types of constitutional units in each of the blocks. Nor is the schematic meant to describe any particular number or arrangement of the constitutional units within a particular block. In each block the constitutional units may be disposed in a purely random, an alternating random, a regular alternating, a regular block or a random block configuration unless expressly stated to be otherwise. A purely random configuration, for example, may have the form: x-x-y-z-x-y-y-z-y-z-z-z . . . . An exemplary alternating random configuration may have the form: x-y-x-z-y-x-y-z-y-x-z . . . , and an exemplary regular alternating configuration may have the form: x-y-z-x-y-z-x-y-z . . . . An exemplary regular block configuration may have the following general configuration: . . . x-x-x-y-y-y-z-z-z-x-x-x . . . , while an exemplary random block configuration may have the general configuration: . . . x-x-x-z-z-x-x-y-y-y-z-z-z-x-x-z-z-z- . . . . In a gradient polymer, the content of one or more monomeric units increases or decreases in a gradient manner from one end to another end of a polymer.

Accordingly, embodiments of the present polymers can include copolymers, block copolymers, or the like. In certain embodiments the first block will include a hydrophilic character, and therefore will be comprised of monomer species that include a hydrophilic character. In certain embodiments the second block will include a hydrophobic character, and therefore will be comprised of monomer species that include a hydrophobic character.

Referring now to the first block, in some embodiments the first block of the polymers include a hydrophilic monomer. Exemplary hydrophilic monomers include ethylene glycol (EG) monomers. First blocks comprising a plurality of bound EG monomers form poly(ethylene glycol) (PEG) chains. In some embodiments the PEG of the first block can include a molecular weight of about 500 Da, 1,000 Da, 2,000 Da, 3,000 Da, 4,000 Da, 5,000 Da, 6,000 Da, 7,000 Da, 8,000 Da, 9,000 Da, 10,000 Da, 11,000 Da, 12,000 Da, 13,000 Da, 14,000 Da, 15,000 Da, 16,000 Da, 17,000 Da, 18000 Da, 19,000 Da, or 20,000 Da. In some embodiments the PEG includes a molecular weight of more than about 20,000 Da.

In some embodiments the first block forms an outer shell (corona) of the nanoparticle. In some embodiments comprising a hydrophilic first block, the hydrophilic outer shell can serve to protect the nanoparticles. More specifically, such blocks on the polymers can reduce or eliminate the extent to which the nanoparticles adsorb proteins. Hydrophilic outer shells on exemplary nanoparticles can also inhibit hemolysis or aggregation of erythrocytes, avoid immune stimulation, improve circulation time, protect the cargo (e.g., active agent) from enzymatic degradation, provide colloidal stability and 'stealth', or a combination thereof.

The second block of exemplary polymers can substantially form a core of the nanoparticle. For example, nanoparticles that are a micelle can be comprised of polymers, wherein the hydrophilic first block forms a corona of the micellar nanoparticle and the second block forms the interior of the micellar nanoparticle.

In some embodiments the second block is comprised of cationic monomers and hydrophobic monomers. In some embodiments the cationic monomers are capable of binding polynucleotide molecules, such as siRNA molecules, or other molecules having an anionic charge. The bond between the cationic monomers and the polynucleotide or other anionic molecules can be an electrostatic bond. The hydrophobic monomers are provided to impart a hydrophobic character to the second block, thereby facilitating assembly of the polymers into nanoparticles.

In various embodiments, such cationic and/or hydrophobic monomers include, but are not limited to, cationic monomers selected from: methyl methacrylate, ethyl acrylate, propyl methacrylate (all isomers), butyl methacrylate (all isomers), 2-ethylhexyl methacrylate, isobornyl methacrylate, methacrylic acid, benzyl methacrylate, phenyl methacrylate, methacrylonitrile, alpha-methylstyrene, methyl acrylate, ethyl acrylate, propyl acrylate (all isomers), butyl acrylate (all isomers), 2-ethylhexyl acrylate, isobornyl acrylate, acrylic acid, benzyl acrylate, phenyl acrylate, acrylonitrile, styrene, acrylates and styrenes selected from glycidyl methacrylate, 2-hydroxyethyl methacrylate, hydroxypropyl methacrylate (all isomers), hydroxybutyl methacrylate (all isomers), N,N-dimethylaminoethyl methacrylate, N,N-diethylaminoethyl methacrylate, triethyleneglycol methacrylate, oligoethyleneglycol methacrylate, itaconic anhydride, itaconic acid, glycidyl acrylate, 2-hydroxyethyl acrylate, hydroxypropyl acrylate (all isomers), hydroxybutyl acrylate (all isomers), N,N-dimethylaminoethyl acrylate, N,N-diethylaminoethyl acrylate, triethyleneglycol acrylate, methacrylamide, N-methylacrylamide, N,N-dimethylacrylamide, N-tert-butylmethacrylamide, N-n-butylmethacrylamide, N-methylolacrylamide, N-ethylolacrylamide, vinyl benzoic acid (all isomers), diethylaminostyrene (all isomers), alpha-methylvinyl benzoic acid (all isomers), diethylamino alpha-methylstyrene (all isomers), p-vinylbenzenesulfonic acid, p-vinylbenzene sulfonic sodium salt, trimethoxysilylpropyl methacrylate, triethoxysilylpropyl methacrylate, tributoxysilylpropyl methacrylate, dimethoxymethylsilylpropyl methacrylate, diethoxymethylsilylpropyl methacrylate, dibutoxymethylsilylpropyl methacrylate, diisopropoxymethylsilylpropyl methacrylate, dimethoxysilylpropyl methacrylate, diethoxysilylpropyl methacrylate, dibutoxysilylpropyl methacrylate, diisopropoxysillpropyl methacrylate, trimethoxysilylpropyl acrylate, triethoxysilylpropyl acrylate, tributoxysilylpropyl acrylate, dimethoxymethylsilylpropyl acrylate, diethoxymethylsilylpropyl acrylate, dibutoxymethylsilylpropyl acrylate, diisopropoxymethylsilylpropyl acrylate, dimethoxysilylpropyl acrylate, diethoxysilylpropyl acrylate, dibutoxysilylpropyl acrylate, diisopropoxysilylpropyl acrylate, vinyl acetate, vinyl butyrate, vinyl benzoate, vinyl chloride, vinyl fluoride, vinyl bromide, maleic anhydride, N-arylmaleimide, N-phenylmaleimide, N-alkylmaleimide, N-butylimaleimide, N-vinylpyrrolidone, N-vinylcarbazole, butadiene, isoprene, chloroprene, ethylene, propylene, 1,5-hexadienes, 1,4-hexadienes, 1,3-butadienes, 1,4-pentadienes, vinylalcohol, vinylamine, N-alkylvinylamine, allylamine, N-alkylallylamine, diallylamine, N-alkyldiallylamine, alkylenimine, acrylic acids, alkylacrylates, acrylamides, methacrylic acids, alkylmethacrylates, methacrylamides, N-alkylacrylamides, N-alkylmethacrylamides, styrene, N-isopropylacryamide, vinylnaphthalene, vinyl pyridine, ethylvinylbenzene, aminostyrene, vinylimidazole, vinylpyridine, vinylbiphenyl, vinylanisole, vinylimidazolyl, vinylpyridinyl, vinylpolyethyleneglycol, dimethylaminomethylstyrene, trimethylammonium ethyl methacrylate, trimethylammonium ethyl acrylate, dimethylamino propylacrylamide, trimethylammonium ethylacrylate, trimethylanunonium ethyl methacrylate, trimethylammonium propyl acrylamide, dodecyl acrylate, octadecyl acrylate, or octadecyl methacrylate monomers, or combinations thereof.

In some embodiments, functionalized versions of these monomers are optionally used. A functionalized monomer, as used herein, is a monomer comprising a masked or non-masked functional group, e.g. a group to which other moieties can be attached following the polymerization. The non-limiting examples of such groups are primary amino groups, carboxyls, thiols, hydroxyls, azides, and cyano groups. Several suitable masking groups are available (see, e.g., T. W. Greene & P. G. M. Wuts, Protective Groups in Organic Synthesis (2nd edition) J. Wiley & Sons, 1991. P. J. Kocienski, Protecting Groups, Georg Thieme Verlag, 1994).

In some embodiments the cationic monomers include N,N-di($C_1$-$C_6$)alkyl-amino($C_1$-$C_6$)alkyl-ethacrylate, N,N-di($C_1$-$C_6$)alkyl-amino($C_1$-$C_6$)alkyl-methacrylate, N,N-di($C_1$-$C_6$)alkyl-amino($C_1$-$C_6$)alkyl-acrylate, or combinations thereof. In some embodiments the hydrophobic monomers include ($C_2$-$C_8$)alkyl-ethacrylate, ($C_2$-$C_8$)alkyl-methacrylate, ($C_2$-$C_8$)alkyl-acrylate, or combinations thereof. In specific embodiments the cationic monomers include 2-(dimethylamino)ethyl methacrylate (DMAEMA). In other specific embodiments the hydrophobic monomers include butyl methacrylate (BMA).

The term "alkyl" refers to alkyl groups with the general formula $C_nH_{2n+1}$, where n=about 1 to about 18 or more. The groups can be straight-chained or branched. Alkyl, when used herein, also comprise "lower alkyls," which refer to alkyl groups with the general formula $C_nH_{2n+1}$, where n=1 to about 6. In some embodiments, n=1 to about 3. Examples include methyl, ethyl, propyl, isopropyl, n-butyl, sec-butyl, t-butyl, isobutyl, n-pentyl, isopentyl, neopentyl, n-hexyl, and the like. In this regard, the term "cycloalkyl" refers to a non-aromatic carbon-based rings composed of at least three carbon atoms, such as cyclopropyl, cyclohexyl, and the like. The term alkyl is inclusive of cycloalkyls.

In some embodiments, the cationic monomer comprises nitrogen species such as ammonium, —NRR'R", guanidinium (—NRC(═NR'H)$^+$NR"R'", including canonical forms that are known to those skilled in the art) wherein the R groups are independently hydrogen, alkyl, cycloalkyl or aryl or two R groups bonded to the same or adjacent nitrogen atoms may be also be joined to one another to form a heterocyclic species such as but not limited to pyrrole, imidazole, or indole.

The second block can also comprise a membrane disruption character that is pH-responsive. At a specific pH, within a range of pH, above a certain pH, and/or below a certain pH the second block can be imparted with a pH-responsive character. In some embodiments the present polymers can comprise a pKa of about 5.0, about 5.5, about 6.0, about 6.5, about 7.0, or about 7.4. Without being bound by theory or mechanism, the cationic monomers can become protonated or become increasingly protonated at a certain pH. Thus, exemplary cationic monomers can be cationic at about physiological pH and/or at about pH 6.0, about pH 7.0, about pH 8.0, at about endosomal pH (e.g., about pH 5 to pH 6), or a combination thereof. In some embodiments the cationic monomers become increasingly protonated at a pH of below about pH 7.4, below about pH 7.0, below about pH 6.5, below about pH 6.0, below about pH 5.0, below about pH 4.5, or below about pH 4.0.

Without being bound by theory or mechanism, exemplary pH-responsive second blocks can become protonated and/or increasingly pronated at certain pHs, thereby making the second blocks cationic and/or increasingly cationic. Once the cationic charge reaches a certain level the charges form a repulsive force within the core of a nanoparticle, which can partially disassemble or wholly disassemble the nanoparticle. Partially disassembled nanoparticles include those that experience morphological changes due to the nanoparticles swelling, the polymers in the nanoparticles becoming increasingly disordered, or the like. Wholly disassembled nanoparticles include those that are disassembled such that some or all of the polymers become unimers in solution. Regardless of the extent of disassembly, at least partial disassembly can lead to exposure of the core of the nanoparticles. Thus, the pH-responsive character of the second block can cause exemplary nanoparticles to disassemble and/or expose their core when in an environment having a certain pH or a pH within a range.

In this regard, in some embodiments of nanoparticles, the plurality of polymers that comprise the nanoparticle can at least partially disassemble to expose a core of the nanoparticle at a pH below about physiological pH. In other embodiments the nanoparticles can at least partially disassemble to expose a core of the nanoparticle at below about pH 7.0. In still further embodiments, the nanoparticles can at least partially disassemble to expose a core of the nanoparticle at below about pH 6.8, pH 6.6, pH 6.4, pH 6.2, pH 6.0, pH 5.8, pH 5.6, pH 5.4, pH 5.2, pH 5.0, pH 4.8, pH 4.6, pH 4.4, pH 4.2, or pH 4.0. In some embodiments the nanoparticles can at least partially disassemble to expose a core of the nanoparticle at below about pH 4.0. As discussed herein, in some embodiments the pH at which the nanoparticles are pH-responsive and/or the pH at which the nanoparticles at least partially disassemble can be tuned by adjusting the types of monomers and relative concentrations of monomers in the polymers, the types of monomers and relative concentrations of monomers in first block of the polymers, the types of monomers and relative concentrations of monomers in the second block of the polymers, or a combination thereof.

In some embodiments the second block comprises hydrophobic monomers and cationic monomers. In some embodiments the molar ratio of hydrophobic monomers relative to all of the hydrophobic monomers and cationic monomers can be about 10 mol %, 15 mol %, 20 mol %, 25 mol %, 30 mol %, 35 mol %, 40 mol %, 45 mol %, 50 mol %, 55 mol %, 60 mol %, 65 mol %, 70 mol %, 75 mol %, 80 mol %, 85 mol %, and/or 95 mol %. In some embodiments the hydrophobic monomers comprise less than about 75 mol %, about 50 mol %, or about 25 mol % of the monomer species in the second block of the polymer. In some embodiments the molar ratio of cationic monomers relative to all of the hydrophobic monomers and cationic monomers can be about 10 mol %, 15 mol %, 20 mol %, 25 mol %, 30 mol %, 35 mol %, 40 mol %, 45 mol %, 50 mol %, 55 mol %, 60 mol %, 65 mol %, 70 mol %, 75 mol %, 80 mol %, 85 mol %, and/or 95 mol %. In some embodiments the cationic monomers comprise less than about 75 mol %, about 50 mol %, or about 25 mol % of the monomer species in the second block of the polymer.

In some embodiments the second block of the polymer is a diblock copolymer that includes a cationic block and a hydrophobic block, the cationic block including cationic monomers (e.g., DAEMA) and the hydrophobic block including hydrophobic monomers (e.g., BMA). In some embodiments the second block consists essentially of a hydrophobic monomer and a cationic monomer. In some embodiments the second block consists essentially of BMA and DMAEMA. In some embodiments the second block consists of a hydrophobic monomer and a cationic monomer. In some embodiments the second block consists of BMA and DMAEMA. In some embodiments the second block does not comprise an alkylacrylic acid, including a ($C_1$-$C_6$)alkyl-acrylic acid, such as propylacrylic acid (PAA).

In some embodiments the second block comprises, consists essentially of, or consists of two types of monomers. Exemplary second blocks having two types of monomers can be relatively simpler and less expensive to synthesize than blocks having three or more types of monomers. The characteristics of second blocks having two monomers can be tuned by varying the total and relative concentrations of the hydrophobic monomer and cationic monomer.

In some embodiments the second block is a diblock copolymer wherein the hydrophobic block links the second block to the first block. In some embodiments the second block is a diblock copolymer wherein the cationic block links the second block to the first block. In this regard, the aforementioned linkage can be a direct linkage, in which the blocks are directly bound to one another, or an indirect linkage, in which one or more compounds, monomers, and/or polymers are located between the bound blocks.

Polynucleotide Carrier

The presently-disclosed subject matter further relates to nanoparticles comprising a plurality of polymers that include a first block that includes hydrophilic monomers, the first block substantially forming an outer shell of the nanoparticle, and a second block that includes cationic monomers and hydrophobic monomers, the second block substantially forming a core of the nanoparticle, the nanoparticles further comprising a polynucleotide that is bound to the cationic monomers.

The terms "nucleotide," "polynucleotide," "nucleic acid," and "nucleic acid sequence" refer to deoxyribonucleotides or ribonucleotides and polymers thereof in either single or double stranded form. The terms are inclusive of oligonucleotides. The terms are also inclusive of plasmids (pDNA). Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified versions thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed base and/or deoxyinosine residues (Batzer et al. (1991) Nucleic Acid Res 19:5081; Ohtsuka et al. (1985) J Biol Chem 260:2605 2608; Rossolini et al. (1994) Mol Cell Probes 8:91 98).

In some embodiments the polynucleotide is a nucleotide capable of inducing RNA interference (RNAi). In specific embodiments the polynucleotide includes DNA, RNA, siRNA, miRNA, pDNA, or a combination thereof. There is no particular limitation on the size of the polynucleotide, and exemplary polynucleotides can comprise about 5, 10, 15, 20, 25, 30, 35, 40, 45, 50, or more nucleic acids in sequence. Thus, as described further below, exemplary polynucleotides can inhibit one or more functions in a cell that is contacted by the nanoparticles comprising the polynucleotide.

Furthermore, the term "siRNA" is used herein as it is in the art, and generally refers to a duplex, as well as single strands, of RNA that are relatively short (e.g., 18-30 base pairs). Some siRNA target complementary mRNA in the antisense strand. Some siRNA play a role in the RNAi pathway and can partially or completely silence a particular gene.

Embodiments of the polymers that form a nanoparticle can comprise a "charge ratio". The charge ratio refers to a ratio of the number of positive charges (cationic) on the cationic monomers that comprise the second block of the polymers (N) to the number of negative charges (anionic) on the polynucleotides that are incorporated into the nanoparticle (P). In some embodiments the cationic charges are cationic amines of the cationic monomers. In some embodiments the anionic charges are anionic charges of the phosphate groups on the backbone the polynucleotide (e.g., siRNA). The ratio can thus be referred to as a N:P ratio. In some embodiments the ratio is calculated at physiological pH, neutral pH, or a combination thereof. In further embodiments, for the purpose of calculating a N:P ratio, the cationic monomers are assumed to have about half (50%) of their cationic species (e.g., amines) charged at the neutral and/or physiological pH.

Exemplary nanoparticles are formed with a particular N:P ratio so as to determine or estimate the dosage of polynucleotides in the nanoparticles. Exemplary nanoparticles are also made at a N:P ratio that achieves the desired characteristics, including size, stability, surface charge, and the like, for the nanoparticles. In some embodiments the N:P ratio is a value between about 0.5 and about 20. In some embodiments the N:P ratio is a value between about 1.0 and about 30. In some embodiments the N:P ratio is a value between about 5.0 and about 15, or a value between about 10 and 10. In further embodiments the N:P ratio is a value of about 1, 2, 3, 4, 5, 6, 7, 8, 9, 10, 11, 12, 13, 14, 15, 16, 17, 18, 19, or 20.

In some embodiments the polynucleotide is bound to the polymer via electrostatic bonds between the polynucleotide and the cationic monomers of polymer. Exemplary nanoparticles comprise a first block that forms an outer shell of the nanoparticle and a second block that forms a core of the nanoparticle, the second block comprising cationic monomers. By virtue of this configuration, in some embodiments the polynucleotides that are bound to the polymers are substantially located within a core of the nanoparticle.

In some embodiments comprising a first hydrophilic block that forms an outer shell of the nanoparticle, the polynucleotide is substantially located within the core of the nanoparticle by virtue of being bound to second block of the polymer that forms the core of the nanoparticles. In some embodiments the first block comprises PEG that forms an outer shell (i.e., corona) of the nanoparticle, and this outer shell can protect the core of the nanoparticle against exposure to the surrounding environment.

Also, in exemplary nanoparticles comprising a hydrophilic first block that forms an outer shell and a core that includes the polynucleotide, the outer shell of the nanoparticle can have a substantially neutral surface charge. Thus, embodiments of the present nanoparticles can comprise a surface zeta-potential of about zero (i.e., neutral zeta-potential). In other embodiments the nanoparticles comprise a surface zeta-potential of about −10 mV to about +10 mV, and in some embodiments the nanoparticles comprise a surface zeta-potential of about −20 mV to about +20 mV, and in still further embodiments nanoparticles comprise a surface zeta-potential of about −30 mV to about +30 mV. In some instances zeta-potentials, such as positive zeta-potentials, can enhance cellular uptake of the nanoparticles in a nonspecific manner. Embodiments that have substantially about neutral surface zeta-potentials can experience relatively less cellular uptake and/or non-specific cellular uptake relative to charged nanoparticles. In some embodiments, nanoparticles that comprise PEG in the first block that forms a corona have a substantially about neutral surface zeta-potentials.

Exemplary nanoparticles comprising surface PEGylation and/or other neutrally charged coronas benefit from enhanced circulation half-life. Enhanced circulation half-life can also further enhance biodistribution of the nanoparticles that have been administered to a subject. Such shielding improves circulation by decreasing aggregation with or adsorption to blood components. Such shield can be configured to not fully shield the nanoparticle core from interaction, maintaining the pH-responsive character of the nanoparticles caused by the components contained in the core, second block. The combination of core hydrophobicity and PEG shielding achieved in certain nanoparticles can increase the circulation half-life and improve passive tumor accumulation and/or, through functionalization with targeting ligands, retention in other target tissues.

Nanoparticle Synthesis

The presently-disclosed subject matter further comprises methods for making a nanoparticle. Exemplary methods first comprise providing a plurality of polymers in a solution. Exemplary polymers include a first block that includes hydrophilic monomers and a second block that includes cationic monomers and hydrophobic monomers. The step of providing a plurality of polymers can include synthesizing the polymers. Polymers described here are prepared in any suitable manner. Suitable synthetic methods used to produce the polymers provided herein include, by way of non-limiting example, cationic, anionic and free radical polymerization. In some instances, when a cationic process is used, the monomer is treated with a catalyst to initiate the polymerization. Optionally, one or more monomers are used to form a copolymer. In some embodiments, such a catalyst is an initiator, including, e.g., protonic acids (Bronsted acid) or Lewis acids, in the case of using Lewis acid some promoter such as water or alcohols are also optionally used. In some embodiments, the catalyst is, by way of non-limiting example, hydrogen iodide, perchloric acid, sulfuric acid, phosphoric acid, hydrogen fluoride, chlorosulfonic acid, methansulfonic acid, trifluoromehtanesulfonic acid, aluminum trichloride, alkyl aluminum chlorides, boron trifluoride complexes, tin tetrachloride, antimony pentachloride, zinc chloride, titanium tetrachloride, phosphorous pentachloride, phosphorus oxychloride, or chromium oxychloride. In certain embodiments, polymer synthesis is performed neat or in any suitable solvent. Suitable solvents include, but are not limited to, pentane, hexane, dichloromethane, chloroform, or dimethyl formamide (DMF). In certain embodiments, the polymer synthesis is performed at any suitable reaction temperature, including, e.g., from about −50° C. to about 100° C., or from about 0° C. to about 70° C.

In certain embodiments, the polymers are prepared by the means of a free radical polymerization. When a free radical polymerization process is used, (i) the monomer, (ii) optionally, the co-monomer, and (iii) an optional source of free radicals are provided to trigger a free radical polymerization process. In some embodiments, the source of free radicals is optional because some monomers may self-initiate upon heating at high temperature. In certain instances, after forming the polymerization mixture, the mixture is subjected to polymerization conditions. Polymerization conditions are those conditions that cause at least one monomer to form at least one polymer, as discussed herein. Such conditions are optionally varied to any suitable level and include, by way of non-limiting example, temperature, pressure, atmosphere, ratios of starting components used in the polymerization mixture and reaction time. The polymerization is carried out in any suitable manner, including, e.g., in solution, dispersion, suspension, emulsion or bulk.

In some embodiments, initiators are present in the reaction mixture. Any suitable initiators is optionally utilized if useful in the polymerization processes described herein. Such initiators include, by way of non-limiting example, one or more of alkyl peroxides, substituted alkyl peroxides, aryl peroxides, substituted aryl peroxides, acyl peroxides, alkyl hydroperoxides, substituted alkyl hydroperoxides, aryl hydroperoxides, substituted aryl hydroperoxides, heteroalkyl peroxides, substituted heteroalkyl peroxides, heteroalkyl hydroperoxides, substituted heteroalkyl hydroperoxides, heteroaryl peroxides, substituted heteroaryl peroxides, heteroaryl hydroperoxides, substituted heteroaryl hydroperoxides, alkyl peresters, substituted alkyl peresters, aryl peresters, substituted aryl peresters, or azo compounds. In specific embodiments, benzoylperoxide (BPO) and/or AIBN are used as initiators.

In some embodiments, polymerization processes are carried out in a living mode, in any suitable manner, such as but not limited to Atom Transfer Radical Polymerization (ATRP), nitroxide-mediated living free radical polymerization (NMP), ring-opening polymerization (ROP), degenerative transfer (DT), or Reversible Addition Fragmentation Transfer (RAFT). Using conventional and/or living/controlled polymerizations methods, various polymer architectures can be produced, such as but not limited to block, graft, star and gradient copolymers, whereby the monomer units are either distributed statistically or in a gradient fashion across the chain or homopolymerized in block sequence or pendant grafts. In other embodiments, polymers are synthesized by Macromolecular design via reversible addition-fragmentation chain transfer of Xanthates (MADIX) (Direct Synthesis of Double Hydrophilic Statistical Di- and Triblock Copolymers Comprised of Acrylamide and Acrylic Acid Units via the MADIX Process", Daniel Taton, et al., Macromolecular Rapid Communications, 22, No. 18, 1497-1503 (2001).)

In certain embodiments, Reversible Addition-Fragmentation chain Transfer or RAFT is used in synthesizing ethylenic backbone of embodied polymers. RAFT is a living polymerization process. RAFT comprises a free radical degenerative chain transfer process. In some embodiments, RAFT procedures for preparing a polymer described herein employs thiocarbonylthio compounds such as, without limitation, dithioesters, dithiocarbamates, trithiocarbonates and xanthates to mediate polymerization by a reversible chain transfer mechanism. In certain instances, reaction of a polymeric radical with the C=S group of any of the preceding compounds leads to the formation of stabilized radical intermediates. Typically, these stabilized radical intermediates do not undergo the termination reactions typical of standard radical polymerization but, rather, reintroduce a radical capable of re-initiation or propagation with monomer, reforming the C=S bond in the process. In some instances, this cycle of addition to the C=S bond followed by fragmentation of the ensuing radical continues until all monomer has been consumed or the reaction is quenched. Low concentration of active radicals at any particular time can limits normal termination reactions.

Method of making nanoparticles can further comprise allowing the polymers in solution to form nanoparticles. In some embodiments the first block of the polymer is hydrophilic and the second block of the polymer comprises hydrophobic monomers, such that the polymers can form micellar nanoparticles in solution with the first block of the polymers forming a nanoparticle outer shell and the second block of the polymers forming a nanoparticle core.

As previously described, the second block can further comprise cationic monomers, and in some embodiments the cationic monomers become protonated or become increasingly protonated as the pH decreases. In some embodiments a method of making a nanoparticle includes adjusting the pH of a solution such that the cationic charges of the second block decrease to a point where the cationic repulsive forces can decrease and permit assembly of the nanoparticles. For example, a method of making a nanoparticle can include providing the present polymers in solution and adjusting the pH of the solution to more than about pH 5.0, more than about pH 5.5, more than about pH 6.0, more than about pH 6.5, more than about pH 7.0, or more than about pH 7.5. In some embodiments a method of making a nanoparticle can include providing the present polymers in solution and adjusting the pH of the solution to more than about endosomal pH, which can be about pH 5.0 to about pH 6.0, to about physiological pH, and/or to about more than physiological pH, which can be about pH 7.4. As the pH of the solution increases, the cationic charge of the second block can decrease so that the hydrophilic character of the first block and the hydrophobic character of the second block (e.g., hydrophobic monomers) permits assembly of the nanoparticles form the polymers.

Exemplary methods also comprise methods for making nanoparticles that comprise a polynucleotide. Exemplary methods comprise adding the polynucleotide to the solution that includes the polymers so that the polymers assemble into nanoparticles that comprise the polynucleotides. In some embodiments the polynucleotides are added to a solution comprising pre-assembled nanoparticles. In some embodiments the polynucleotides are added to a solution that partially or wholly comprises polymers that are unimers in the solution. Polymers that are unimers can expose both their first block and their second block, permitting the polynucleotide to contact or come into proximity with the cationic monomers that are on the second block. Incorporating polynucleotides to a solution that comprises at least some polymers that are unimers can permit the polynucleotides to bind (e.g., electrostatically) the cationic monomers of the polymers. Furthermore, as the polynucleotides bind the cationic monomers they can decrease or neutralize the cationic charge of the cationic monomers.

In some embodiments the polynucleotides are substantially found in the core of the nanoparticle. In some embodiments nanoparticles having polynucleotides in their core are formed by providing a plurality of the present polymers in solution and adjusting the solution to less than about pH 7.0, or any of the pHs stated above that can provide at least some of the polymers in a unimeric state. Next, the polynucleotides can be added to the solution and can be allowed to bind to the cationic monomers on the polymers. In some embodiments the binding of the polynucleotides decreases or neutralizes the cationic charge of the cationic monomers to a level sufficient to permit assembly of the nanoparticles. In other embodiments and/or to further permit assembly of the nanoparticles, embodiments of the present methods can comprise raising the pH of the solution to at least about pH 6.0, to at least pH 6.5, to at least pH 7.0, to at least pH 7.5, and/or to at least physiological pH. In some embodiments, as the pH raises, the cationic charges of the cationic monomers can further decrease and/or be neutralized further permitting assembly of the nanoparticles.

Thus, in some embodiments polynucleotides are added to a solution that comprises the polymers at relatively low pH, and subsequently the pH of the solution is raised to a relatively higher pH. In some embodiments the polynucleotide is added to the polymers in a solution of a pH of about 4.0 to about 6.0. The pH of the solution can then be raised to any pH that suitably permits the nanoparticles to assemble. In certain embodiments the pH of the solution is subsequently raised to about physiological pH.

In some embodiments the pH at which the polymers exists as unimers in solution depends on the ratio of cationic monomers to hydrophobic monomers in the second block of the polymers. For instance, as the relative concentration of hydrophobic monomers increases, the pH at which the polymers exists as unimers can decrease, since a greater amount of cationic repulsive forces are required to counteract the hydrophilic-hydrophobic forces of the polymers that otherwise drive nanoparticle assembly. In some embodiments the cationic monomer is DMAEMA and the hydrophobic monomer is BMA, and the pH at which the polymers exist as unimers decreases as the ratio of BMA to DMAEMA increases. The lowering of pH causes the DMAEMA to become increasingly protonated, which causes the polymers to exist as solubilized unimers due to electrostatic repulsion between poly(DMAEMA-co-BMA) blocks. In this unimeric state, the cationic polymer segments are exposed, and mixing with polynucleotide triggers electrostatic interactions that drive formation of nanoparticles core-stabilized by electrostatic (PEG-DMAEMA) or a combination of electrostatic and hydrophobic interactions PEG-(DMAEAM-co-BMA).

The resulting nanoparticles can comprise a diameter of about 1 nm to about 1000 nm. In some embodiments the nanoparticles comprise a diameter of about 1 to about 100 nm, of about 1 to about 50 nm, or of about 1 to about 25 nm. In some embodiments the nanoparticles include a diameter of about 100 nm, 200 nm, 300 nm, 400 nm, 500 nm, 600 nm, 700 nm, 800 nm, 900 nm, or 1000 nm. In some embodiments the nanoparticles include a diameter of about 10 nm, 20 nm, 30 nm, 40 nm, 50 nm, 60 nm, 70 nm, 80 nm, or 90 nm. In some embodiments the diameter of the nanoparticles refers to a hydrodynamic diameter. In some embodiments the diameter is one measured by known methods. In certain embodiments the diameter is one measured with transmission electron microscopy (TEM), with dynamic light scattering (DLS), or the like.

The presently-disclosed subject matter further includes pharmaceutical compositions comprising the nanoparticles described herein as well as a pharmaceutically acceptable carrier. As such, it should be understood that all recitations of nanoparticles herein are inclusive of pharmaceutical compositions thereof. For example, methods for treating a subject by administering nanoparticles can be inclusive of methods for treating a subject by administering pharmaceutical compositions that include nanoparticles.

The term "pharmaceutically acceptable carrier" refers to sterile aqueous or nonaqueous solutions, dispersions, suspensions or emulsions, as well as sterile powders for reconstitution into sterile injectable solutions or dispersions just prior to use. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The formulations can be presented in unit-dose or multi-dose containers, for example sealed ampoules and vials, and can be stored in a frozen or freeze-dried (lyophilized) condition requiring only the addition of sterile liquid carrier immediately prior to use.

For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art.

Liquid preparations for oral administration can take the form of, for example, solutions, syrups or suspensions, or they can be presented as a dry product for constitution with water or other suitable vehicle before use. Such liquid preparations can be prepared by conventional techniques with pharmaceutically acceptable additives such as suspending agents (e.g., sorbitol syrup, cellulose derivatives or hydrogenated edible fats); emulsifying agents (e.g. lecithin or *acacia*); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate. Preparations for oral administration can be suitably formulated to give controlled release of the active compound. For buccal administration the compositions can take the form of tablets or lozenges formulated in conventional manner.

The compositions can also be formulated as a preparation for implantation or injection. Thus, for example, the compounds can be formulated with suitable polymeric, aqueous, and/or hydrophilic materials, or resins, or as sparingly soluble derivatives (e.g., as a sparingly soluble salt). The compounds can also be formulated in rectal compositions, creams or lotions, or transdermal patches.

Methods of Use

The presently-disclosed subject matter includes methods for using the present nanoparticles. Some exemplary methods include methods for inducing RNAi in a cell, the methods comprising contacting a nanoparticle to the cell, the nanoparticle including a plurality of polymers each comprising a first block that includes hydrophilic monomers, the first block substantially forming an outer shell of the nanoparticle, a second block that includes cationic monomers and hydrophobic monomers, the second block substantially forming a core of the nanoparticle, and a polynucleotide that is bound to the cationic monomers, the polynucleotide being capable of inducing RNAi in the cell.

RNAi references the partial or complete silencing of a gene by the administration of a polynucleotide, and namely an RNA molecule. RNAi can therefore be used to reduce or eliminate the expression of certain genes, proteins, or the like in certain cells. As used herein, the reduction and/or elimination of certain genes, proteins, enzymes, functions or the like are collectively referred to as the inhibition of certain function. Thus, the present nanoparticles can be used to inhibit certain aspects of cells, and thus can serve as "inhibitors". In specific embodiments the nanoparticles can inhibit the proliferation of a cell.

The term "inhibiting" or "inhibition" does not necessarily refer to the ability to completely inactivate all target biological activity in all cases. Rather, the skilled artisan will understand that the term "inhibiting" refers to decreasing biological activity of a target, such as can occur with a ligand binding site of the target, or protein in a biochemical pathway of the target, is blocked. Such decrease in biological activity can be determined relative to a control, wherein an inhibitor is not administered and/or placed in contact with the target. For example, in some embodiments, a decrease in activity relative to a control can be about a 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% decrease. The term "inhibitor" thus refers to nanoparticles and compositions thereof that can inactivate or decrease the biological activity of a target.

In some embodiments the present nanoparticles can be used to treat a condition (e.g., disease) of a subject. In specific embodiments the nanoparticles can treat a condition of interest by inhibiting a particular pathway, protein, or the like. In some embodiments nanoparticles that include RNAi can treat a particular condition. Thus, some embodiments of the presently-disclosed subject matter include methods of treating a condition in a subject in need thereof, the method comprising administering the present nanoparticles to the subject.

The terms "treatment" or "treating" refer to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "effective amount", as used herein, refers to an amount of nanoparticles sufficient to produce a measurable biological response (e.g., tissue regeneration/repair). Actual dosage levels of the nanoparticles can be varied so as to administer an amount of antioxidant molecules that is effective to achieve the desired response for a particular subject and/or application. The selected dosage level will depend upon a variety of factors including the type of tissue being addressed, the types of cells and gel beads used, combination with other drugs or treatments, severity of the condition being treated, and the physical condition and prior medical history of the subject being treated. Preferably, a minimal dose is administered, and dose is escalated in the absence of dose-limiting toxicity to a minimally effective amount.

The term "administering" refers to any method of providing a nanoparticle to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, and parenteral administration, including injectable such as intravenous administration, intra-arterial administration, intramuscular administration, and subcutaneous administration. Administration can be continuous or intermittent. In various aspects, a nanoparticle can be administered therapeutically; that is, administered to treat an existing disease or condition. In further various aspects, a nanoparticle can be administered prophylactically; that is, administered for prevention of a disease or condition.

Furthermore, the term "subject" includes both human and animal subjects. Thus, veterinary therapeutic uses are provided in accordance with the presently disclosed subject matter and the presently-disclosed subject matter provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

Embodiments of the present nanoparticles can provide cytosolic delivery of polynucleotides and/or other active agents when contacted with a cell and/or administered to a subject. For some administration methods, such as intravenous delivery systems, avoidance of destabilization and/or nonspecific interactions with cells and other blood components helpful for hemocompatibility and for maximizing blood circulation time in order to allow for passive tumor accumulation or active tissue targeting of intact, nanoparticles. In some embodiments the hydrophilic character of the first block can protect the core of the nanoparticles, include the polynucleotides in the core of the nanoparticle, from interaction with the surrounding environment. In some embodiments a neutral or substantially neutral surface zetapotential of a nanoparticle can reduce or prevent it being uptaken by cells. For example, cationic surface charges can drive cellular uptake, and therefore nanoparticles that comprise neutral first blocks that form a corona can exhibit stable behavior in blood or other cellular environment. In some embodiments the corona can act as a steric shield for the nanoparticle. This protection can increase the circulation time of the nanoparticles. This protection can also increase the biodistribution of the nanoparticles.

In some embodiments nanoparticles can have a circulation half-life in a subject of about 6 hours, 12 hours, 18 hours, 24 hours, 30 hours, 36 hours, 42 hours, or 48 hours. In some embodiments the nanoparticles can comprise a circulation half-life of more than about 48 hours. In some embodiments circulation half-life can be enhanced by increasing the concentration of hydrophobic monomer in the second block of the polymer, thereby increasing the forces necessary to disassemble the nanoparticles.

In some embodiments delivery of the nanoparticles to an environment having a relatively lower pH can cause at least the partial disassembly of the nanoparticles. In particular, some nanoparticles have a pH-responsive character, and when exposed to a lower pHs the nanoparticles at least partially dissemble to expose the core of the nanoparticles. Without being bound by theory or mechanism, in some embodiments a lower pH can increase the cationic charges on the cationic monomers present in the core of a nanoparticle, and the repulsive forces due to the increased cationic charges can cause the nanoparticles to at least partially disassemble.

The at least partially disassembly of the nanoparticles can expose the polynucleotides that are bound to in the core of the nanoparticles to the surrounding environment. Thus, at least partial disassembly of the nanoparticles can allow the polynucleotides to be delivered to their final target. At least partial disassembly can also expose the cationic monomer (e.g., DMAEMA) and hydrophobic monomer (e.g., BMA) of the second block to the surrounding environment, and the cationic monomer and/or hydrophobic monomer can have a membrane disruptive character. More specifically, exposure of the monomers in the second block of the polymers that comprise the nanoparticles can induce the disruption of any membranes that contain the nanoparticles. Thus, in some embodiments, after the uptake of the nanoparticles into a cell, the nanoparticles can at least partially disassemble to deliver the polynucleotide in a pH-responsive manner. In some embodiments the nanoparticles at least partially disassemble at about or below an endosomal pH, and therefore after uptake of the nanoparticles into the endosome, endosomal pH's can drive the nanoparticles to disassemble. The at least partially disassembled nanoparticles can then disrupt the endosomal or liposomal membranes so that the polynucleotide can be delivered to the cytosol of a particular cell.

Targeting

In certain embodiments, present nanoparticles further comprise at least one targeting agent. The term "targeting agent" is used herein to refer to a moiety, compound, etc. that specifically binds a particular type or category of cells and/or other particular type compounds. (e.g., a moiety that targets a specific cell or type of cell). A "targeting agent" can be specific (e.g., have an affinity) for the surface of certain target cells, a target cell surface antigen, a target cell receptor, or a combination thereof. In some embodiments a "targeting agent" refers to an agent that has a particular action (e.g., cleaves) when exposed to a particular type or category of substances and/or cells, and this action can drive the nanoparticle to target a particular type or category of cell. Thus, the term "targeting agent" can refer to an agent that is part of a nanoparticle and that plays a role in the nanoparticle's targeting mechanism, although the agent itself may or may not be specific for the particular type or category of cell itself.

In certain instances, the efficiency of the cell uptake of the nanoparticles is enhanced and/or make more specific by incorporation of targeting agents into the present nanoparticles. In certain embodiments, nanoparticles described herein comprise one or more small molecule targeting agents (e.g., carbohydrate moieties). Suitable targeting agents also include, by way of non-limiting example, antibodies, antibody-like molecules, or peptides, such as an integrin-binding peptides such as RGD-containing peptides, or small molecules, such as vitamins, e.g., folate, sugars such as lactose and galactose, or other small molecules. Cell surface antigens include a cell surface molecule such as a protein, sugar, lipid or other antigen on the cell surface. In specific embodiments, the cell surface antigen undergoes internalization. Examples of cell surface antigens targeted by the targeting agents of embodiments of the present nanoparticles include, but are not limited, to the transferrin receptor type 1 and 2, the EGF receptor, HER2/Neu, VEGF receptors, integrins, NGF, CD2, CD3, CD4, CD8, CD19, CD20, CD22, CD33, CD43, CD38, CD56, CD69, and the asialoglycoprotein receptor. A targeting agent can also comprise an artificial affinity molecule, e.g., a peptidomimetic or an aptamer. In some embodiments, the targeting agent is a proteinaceous targeting agent (e.g., a peptide, and antibody, an antibody fragment). In some specific embodiments, a nanoparticle can comprise a plurality of different targeting agents.

In some embodiments, one or more targeting agents are coupled to the polymers that form the nanoparticle. In different embodiments the targeting agents can be bound to the first block of the present polymers, the second block of the present polymers, a pendant group of one or more monomeric units on the first block and/or the second block, or a combination there. In different embodiments targeting ligands are attached to either end of a polymer (e.g., block copolymer) of the nanoparticles, or to a side chain or a pendant group of a monomeric unit, or incorporated into a polymer. In some instances, the targeting agent is covalently coupled to the first block and/or the second block of the present polymers. In some embodiments the targeting agent is bound to the polymers such that the targeting agent is substantially at or near the surface of the resulting nanoparticles. In certain embodiments, a monomer comprising a targeting agent residue (e.g., polymerizable derivative of a targeting agent such as an (alkyl)acrylic acid derivative of a peptide) is co-polymerized to form the copolymer forming the nanoparticle provided herein.

In certain embodiments, one or more targeting agent is coupled to the polymer of the present nanoparticles through a linking moiety. In some embodiments, the linking moiety coupling the targeting agent to the membrane-destabilizing polymer is a cleavable linking moiety (e.g., comprises a cleavable bond), In some embodiments, the linking moiety is cleavable and/or comprises a bond that is cleavable in endosomal conditions. In some embodiments, the linking moiety is cleavable and/or comprises a bond that is cleavable by a specific enzyme (e.g., a phosphatase, or a protease), In some embodiments, the linking moiety is cleavable and/or comprises a bond that is cleavable upon a change in an intracellular parameter (e.g., pH, redox potential). In some embodiments, the linking moiety is cleavable and/or comprises a bond that is cleavable upon exposure to a matrix metalloproteinase (MMP) (e.g., MMP-cleavable peptide linking moiety).

In certain embodiments the targeting mechanism of the nanoparticle depends on a cleavage of a cleavable segment in the polymer. For instance, the present polymers can comprise a cleavable segment that, when cleaved, exposes the nanoparticle and/or the core of a nanoparticle. The cleavable segment can be located at either or both terminal ends of the present polymers in some embodiments. IN some embodiments the cleavable segment is located along a length of a polymer, and optionally can be located between blocks of a polymer. For example, in certain embodiments the cleavable segment is located between a first block and a second block of a polymer, and when the nanoparticle is exposed to a particular cleaving substance the first block is cleaved from the second block. In specific embodiments the cleavable segment is an MMP-cleavable peptide that is cleaved upon exposure to MMP.

Attachment of the targeting agent to the polymer is achieved in any suitable manner, e.g., by any one of a number of conjugation chemistry approaches including but not limited to amine-carboxyl linkers, amine-sulfhydryl linkers, amine-carbohydrate linkers, amine-hydroxyl linkers, amine-amine linkers, carboxyl-sulfhydryl linkers, carboxyl-carbohydrate linkers, carboxyl-hydroxyl linkers, carboxyl-carboxyl linkers, sulfhydryl-carbohydrate linkers, sulfhydryl-hydroxyl linkers, sulfhydryl-sulfhydryl, linkers, carbohydrate-hydroxyl linkers, carbohydrate-carbohydrate linkers, and hydroxyl-hydroxyl linkers. In specific embodiments, "click" chemistry is used to attach the targeting agent to the polymers of the nanoparticles provided herein (for example of "click" reactions, see Wu, P.; Fokin, V, V. Catalytic Azide-Alkyne Cycloaddition: Reactivity and Applications, *Aldrichim. Acta* 2007, 40, 7-17). A large variety of conjugation chemistries are optionally utilized (see, for example, Bioconjugation, Aslam and Dent, Eds, Macmillan, 1998 and chapters therein). In some embodiments, targeting agents are attached to a monomer and the resulting compound is then used in the polymerization synthesis of a polymer copolymer) utilized in a nanoparticle described herein. In some embodiments, the targeting agent is attached to the sense or antisense strand of siRNA bound to a polymer of the nanoparticle. In certain embodiments, the targeting agent is attached to a 5' or a 3' end of the sense or the antisense strand.

Conditions for Treatment

Conditions that can be treated with embodiments of the present nanoparticles, and particularly the polynucleotides (e.g., siRNA) delivered by the nanoparticles herein include, without limitation, pathogenic disorders, cancers, inflammatory diseases, enzyme deficiencies, inborn errors of metabolism, infections, auto-immune diseases, cardiovascular diseases, neurological, neurodegenerative, diseases, neuromuscular diseases, blood disorders and clotting disorders. In some embodiments, the non-limiting examples of the siRNA decreases or down-regulate expression of, or can be originated from, PTP1B, dual-specificity phosphatases (DSP), c-myc, c-myb, c-fos, c-jun, c-raf, c-src, bcl-2, vascular endothelial growth factor (VEGF), VEGF-B, VEGF-C, VEGF-D, or PIGF.

In some embodiments, the nanoparticles (e.g., micelles) provided herein are useful in treating a subject at risk for or afflicted with disorders associated with and/or caused by high plasma levels or cholesterol, apolipoprotein b, and/or LDL cholesterol, e.g. hypercholesterolemia. In some embodiments the polynucleotide inhibits (e.g., silences) proprotein convertase subtilisin/kexin type 9 (PCSK9) gene responsible for regulation of low density lipoprotein (LDLR) levels and function, and thus nanoparticles comprising such polynucleotides can be used to treat a subject having or at risk for a disorder characterized by unwanted PCSK9 expression, e.g., disorders associated with and/or caused by high plasma levels or cholesterol, apolipoprotein b, and/or LDL cholesterol, e.g. hypercholesterolemia. In some embodiments, the polymeric carrier deliver PCSK9-silencing polynucleotide agent (e.g., siRNA) to a cell expressing PCSK9. In some embodiments, the cell is a liver cell.

In some embodiments, the nanoparticles are useful in treating a subject at risk for or afflicted with unwanted cell proliferation (e.g., malignant or nonmalignant cell proliferation). The treatment comprises providing a polymeric carrier comprising a polynucleotide, wherein the polynucleotide is homologous and can silence (e.g., by cleavage) a gene which promotes unwanted cell proliferation; and administering a therapeutically effective dose of the polymeric carrier to a subject (e.g., a human subject.).

In certain embodiments, the gene to be inhibited can include, but is not limited to, a growth factor or growth factor receptor gene, a phosphatase, a kinase, e.g., a protein tyrosine, serine or threonine kinase gene, an adaptor protein gene, a gene encoding a G protein superfamily molecule, or a gene encoding a transcription factor. In some instances, the polymeric carrier comprises a polynucleotide which silences a gene which is expressed in a specific tissue or organ, including, but not limited to lung, pancreas, liver, kidney, ovary, muscle, skin, breast, colon, stomach, and the like.

In some embodiments, the polynucleotide inhibits one or more of the following genes: the PDGF beta gene, and thus can be used to treat a subject having or at risk for a disorder characterized by unwanted PDGF beta expression, e.g., testicular and lung cancers; an Erb-B gene (e.g., Erb-B-2 or Erb-B-3), and thus can be used to treat a subject having or at risk for a disorder characterized by unwanted Erb-B expression, e.g., breast or lung cancer; the Src gene, and thus can be used to treat a subject having or at risk for a disorder characterized by unwanted Src expression, e.g., colon cancers; the CRK gene, and thus can be used to treat a subject having or at risk for a disorder characterized by unwanted CRK expression, e.g., colon and lung cancers; the GRB2 gene, and thus can be used to treat a subject having or at risk for a disorder characterized by unwanted GRB2 expression, e.g., squamous cell carcinoma; the RAS gene, and thus can be used to treat a subject having or at risk for a disorder characterized by unwanted RAS expression, e.g., pancreatic, colon and lung cancers, and chronic leukemia; the MEKK gene, and thus can be used to treat a subject having or at risk for a disorder characterized by unwanted MEKK expression, e.g., squamous cell carcinoma, melanoma or leukemia; the JNK gene, and thus can be used to treat a subject having or at risk for a disorder characterized by unwanted JNK expression, e.g., pancreatic or breast cancers; the RAF gene, and thus can be used to treat a subject having or at risk for a disorder characterized by unwanted RAF expression, e.g., lung cancer or leukemia; the Erk1/2 gene, and thus can be used to treat a subject having or at risk for a disorder characterized by unwanted Erk1/2 expression, e.g., lung cancer; the PCNA(p21) gene, and thus can be used to treat a subject having or at risk for a disorder characterized by unwanted PCNA expression, e.g., lung cancer; the MYB gene, and thus can be used to treat a subject having or at risk for a disorder characterized by unwanted MYB expression, e.g., colon cancer or chronic myelogenous leukemia; the c-MYC gene, and thus can be used to treat a subject having or at risk for a disorder characterized by unwanted c-MYC expression, e.g., Burkitt's lymphoma or neuroblastoma; the JUN gene, and thus can be used to treat a subject having or at risk for a disorder characterized by unwanted JUN expression, e.g., ovarian, prostate or breast cancers; the FOS gene, and thus can be used to treat a subject having or at risk for a disorder characterized by unwanted FOS expression, e.g., skin or prostate cancers; the BCL-2 gene, and thus can be used to treat a subject having or at risk for a disorder characterized by unwanted BCL-2 expression, e.g., lung or prostate cancers or Non-Hodgkin lymphoma; the Cyclin D gene, and thus can be used to treat a subject having or at risk for a disorder characterized by unwanted Cyclin D expression, e.g., esophageal and colon cancers; the VEGF gene, and thus can be used to treat a subject having or at risk for a disorder characterized by unwanted VEGF expression, e.g., esophageal and colon cancers; the EGFR gene, and thus can be used to treat a subject having or at risk for a disorder characterized by unwanted EGFR expression, e.g., breast cancer; the Cyclin A gene, and thus can be used to treat a subject having or at risk for a disorder characterized by unwanted Cyclin A expression, e.g., lung and cervical cancers; the Cyclin E gene, and thus can be used to treat a subject having or at risk for a disorder characterized by unwanted Cyclin E expression, e.g., lung and breast cancers; the WNT-1 gene, and thus can be used to treat a subject having or at risk for a disorder characterized by unwanted WNT-1 expression, e.g., basal cell carcinoma; the beta-catenin gene, and thus can be used to treat a subject having or at risk for a disorder characterized by unwanted beta-catenin expression, e.g., adenocarcinoma or hepatocellular carcinoma; the c-MET gene, and thus can be used to treat a subject having or at risk for a disorder characterized by unwanted c-MET expression, e.g., hepatocellular carcinoma; the PKC gene, and thus can be used to treat a subject having or at risk for a disorder characterized by unwanted PKC expression, e.g., breast cancer; the NFKB gene, and thus can be used to treat a subject having or at risk for a disorder characterized by unwanted NFKB expression, e.g., breast cancer; the STAT3 gene, and thus can be used to treat a subject having or at risk for a disorder characterized by unwanted STAT3 expression, e.g., prostate cancer; the survivin gene, and thus can be used to treat a subject having or at risk for a disorder characterized by unwanted survivin expression, e.g., cervical or pancreatic cancers; the Her2/Neu gene, and thus can be used to treat a subject having or at risk for a disorder characterized by unwanted Her2/Neu expression, e.g., breast cancer; the topoisomerase I gene, and thus can be used to treat a subject having or at risk for a disorder characterized by unwanted topoisomerase I expression, e.g., ovarian and colon cancers; the topoisomerase II alpha gene, and thus can be used to treat a subject having or at risk for a disorder characterized by unwanted topoisomerase II expression, e.g., breast and colon cancers.

In other embodiments the polynucleotide inhibits mutations in one of the following genes: the p73 gene, and thus can be used to treat a subject having or at risk for a disorder characterized by unwanted p73 expression, e.g., colorectal adenocarcinoma; the p21(WAF1/CIP1) gene, and thus can be used to treat a subject having or at risk for a disorder characterized by unwanted p21(WAF1/CIP1) expression, e.g., liver cancer; the p27(KIP1) gene, and thus can be used to treat a subject having or at risk for a disorder characterized by unwanted p27(KIP1) expression, e.g., liver cancer; the PPM1D gene, and thus can be used to treat a subject having or at risk for a disorder characterized by unwanted PPM1D expression, e.g., breast cancer; the RAS gene, and thus can be used to treat a subject having or at risk for a disorder characterized by unwanted RAS expression, e.g., breast cancer; the caveolin I gene, and thus can be used to treat a subject having or at risk for a disorder characterized by unwanted caveolin I expression, e.g., esophageal squamous cell carcinoma; the MIB I gene, and thus can be used to treat a subject having or at risk for a disorder characterized by unwanted MIB I expression, e.g., male breast carcinoma (MBC); MTAI gene, and thus can be used to treat a subject having or at risk for a disorder characterized by unwanted MTAI expression, e.g., ovarian carcinoma; the M68 gene, and thus can be used to treat a subject having or at risk for a disorder characterized by unwanted M68 expression, e.g., human adenocarcinomas of the esophagus, stomach, colon, and rectum.

In some embodiments the polynucleotide inhibits mutations in tumor suppressor genes, and thus can be used as a method to promote apoptotic activity in combination with chemotherapeutics. In some embodiments the in the tumor suppressor gene is selected from one or more of the following tumor suppressor genes: the p53 tumor suppressor gene, the p53 family member DN-p63, the pRb tumor suppressor gene, the APC1 tumor suppressor gene, the BRCA1 tumor suppressor gene, the PTEN tumor suppressor gene.

In some embodiments the polynucleotide inhibits one of the following fusion genes: mLL fusion genes, e.g., mLL-AF9, and thus can be used to treat a subject having or at risk for a disorder characterized by unwanted mLL fusion gene expression, e.g., acute leukemias; the BCR/ABL fusion gene, and thus can be used to treat a subject having or at risk for a disorder characterized by unwanted BCR/ABL fusion gene expression, e.g., acute and chronic leukemias; the TEL/AML1 fusion gene, and thus can be used to treat a subject having or at risk for a disorder characterized by unwanted TEL/AML1 fusion gene expression, e.g., childhood acute leukemia; the EWS/FLI1 fusion gene, and thus can be used to treat a subject having or at risk for a disorder characterized by unwanted EWS/FLI1 fusion gene expression, e.g., Ewing Sarcoma; the TLS/FUS1 fusion gene, and thus can be used to treat a subject having or at risk for a disorder characterized by unwanted TLS/FUS1 fusion gene expression, e.g., Myxoid liposarcoma; the PAX3/FKHR fusion gene, and thus can be used to treat a subject having or at risk for a disorder characterized by unwanted PAX3/FKHR fusion gene expression, e.g., Myxoid liposarcoma; the AML1/ETO fusion gene, and thus can be used to treat a subject having or at risk for a disorder characterized by unwanted AML1/ETO fusion gene expression, e.g., acute leukemia.

In some embodiments the polynucleotide inhibits one of the following genes: the alpha v-integrin gene, and thus can be used to treat a subject having or at risk for a disorder characterized by unwanted alpha V integrin, e.g., brain tumors or tumors of epithelial origin; the Flt-1 receptor gene, and thus can be used to treat a subject having or at risk for a disorder characterized by unwanted Flt-1 receptors, e.g., cancer and rheumatoid arthritis; the tubulin gene, and thus can be used to treat a subject having or at risk for a disorder characterized by unwanted tubulin, e.g., cancer and retinal neovascularization.

In some aspects the polynucleotides provided can treat a subject infected with a virus or at risk for or afflicted with a disorder or disease associated with a viral infection, wherein the polynucleotide is homologous to and/or can silence, e.g., by cleavage, a viral gene or a cellular gene which mediates viral function, e.g., entry or growth; and administering a therapeutically effective dose of said oligonucleotide agent to a subject, e.g., a human subject. In some embodiments the condition to be treated with the present polynucleotides includes Human Papilloma Virus (HPV), Human Immunodeficiency Virus (HIV), and/or a disorder mediated by HPV and/or, e.g., cervical cancer or Acquired Immune Deficiency Syndrome (AIDS). In some embodiments, the HPV gene is selected from the group of E2, E6, or E7. In another embodiment the expression of a human gene that is required for HPV replication is reduced. In some embodiments, the expression of an HIV gene is inhibited. In other embodiments, the HIV gene is CCR5, Gag, or Rev. In some embodiments the expression of a human gene that is required for HIV replication is inhibited. In some embodiments, the gene is CD4 or Tsg101.

In some aspects the polynucleotides provided can treat a subject infected by the Hepatitis B Virus (HBV) or at risk for or afflicted with a disorder mediated by HBV, e.g., cirrhosis and heptocellular carcinoma. In one embodiment, the expression of a HBV gene is inhibited. In some aspects the polynucleotides provided can treat a subject infected with, or at risk for or afflicted with a disorder mediated by a virus selected from the following viruses: the Hepatitis A Virus (HAV); Hepatitis C Virus (HCV); any of the group of Hepatitis Viral strains comprising hepatitis D, E, F, G, or H; the Respiratory Syncytial Virus (RSV); the herpes Cytomegalovirus (CMV); the herpes Epstein Ban Virus (EBV); Kaposi's Sarcoma-associated Herpes Virus (KSHV); the JC Virus (JCV); myxovirus (e.g., virus causing influenza), rhinovirus (e.g., virus causing the common cold), or coronavirus (e.g., virus causing the common cold); the St. Louis Encephalitis flavivirus; the Tick-borne encephalitis flavivirus; the Murray Valley encephalitis flavivirus; the dengue flavivirus; the Simian Virus 40 (SV40); the encephalomyocarditis virus (EMCV); the measles virus (MV); the Varicella zoster virus (VZV); an adenovirus (e.g. virus causing a respiratory tract infection); the poliovirus; or a poxvirus (a poxvirus causing smallpox).

In some aspects the polynucleotides provided can treat a subject infected by the Herpes Simplex Virus (HSV) or at risk for or afflicted with a disorder mediated by HSV, e.g., genital herpes and cold sores as well as life-threatening or sight-impairing disease, e.g., mainly in immunocompromised subjects. In some embodiments, the expression of a HSV gene is inhibited. In some embodiments the expression of a human gene that is required for HSV replication is inhibited.

In some aspects the polynucleotides provided can treat a subject infected by the West Nile Virusor at risk for or afflicted with a disorder mediated by West Nile Virus. In some embodiments, the expression of a West Nile Virus gene is inhibited, such as the West Nile Virus gene selected from the group comprising E, NS3, or NS5. In some embodiments the expression of a human gene that is required for West Nile Virus replication is inhibited.

In some aspects the polynucleotides provided can treat a subject infected by the Human T Cell Lymphotropic Virus (HTLV), or a disease or disorder associated with this virus, e.g., leukemia or myelopathy. In some embodiments, the expression of a HTLV gene is inhibited. In some embodiments, the HTLV1 gene is the Tax transcriptional activator. In some embodiments, the expression of a human gene that is required for HTLV replication is inhibited.

In some aspects the polynucleotides provided can treat a subject infected with a pathogen, e.g., a bacterial, amoebic, parasitic, or fungal pathogen, such as *plasmodium* that causes malaria. In such methods, the provided polynucleotide is homologous to and/or can inhibit, e.g., by cleavage of a pathogen gene or a gene involved in the pathogen's growth; and administering an effective dose of said oligonucleotide agent to a subject, e.g., a human subject. The target gene can be selected from a gene involved in the pathogen's growth, cell wall synthesis, protein synthesis, transcription, energy metabolism, e.g., the Krebs cycle, or toxin production. Thus, in some embodiments, the polymeric carrier comprises an oligonucleotide agent useful for of treating patients infected by a. In some embodiments, the expression of a *plasmodium* gene is reduced.

In some aspects the polynucleotides provided can treat a subject infected by *Mycobacterium ulcerans, Mycobacterium tuberculosis, Mycobacterium leprae, Staphylococcus aureus, Streptococcus pneumoniae, Streptococcus pyogenes, Chlamydia pneumoniae, Mycoplasma pneumoniae*, or a disease or disorder associated with any of these pathogens. In some embodiments, the expression of a bacterial gene and/or a human gene that is required for the replication of these bacteria is inhibited.

In some aspects the polynucleotides provided can treat a subject at risk for or afflicted with a disease or disorder characterized by an unwanted immune response, e.g., an inflammatory disease or disorder or an autoimmune disease or disorder. In some embodiments, the disease or disorder is an ischemia or reperfusion injury, e.g., ischemia or reperfusion injury associated with acute myocardial infarction, unstable angina, cardiopulmonary bypass, surgical intervention e.g., angioplasty, e.g., percutaneous transluminal coronary angioplasty, the response to a transplanted organ or tissue, e.g., transplanted cardiac or vascular tissue; or thrombolysis. In other embodiments, the disease or disorder is restenosis, e.g., restenosis associated with surgical intervention e.g., angioplasty, e.g., percutaneous transluminal coronary angioplasty. In other embodiments, the disease or disorder is Inflammatory Bowel Disease, e.g., Crohn Disease or Ulcerative Colitis. In some embodiments, the disease or disorder is inflammation associated with an infection or injury. In other embodiments, the disease or disorder is asthma, allergy, lupus, multiple sclerosis, diabetes, e.g., type II diabetes, arthritis, e.g., rheumatoid or psoriatic. In certain embodiments the polynucleotide inhibits an integrin or co-ligand thereof, e.g., VLA4, VCAM, ICAM, or it can inhibit a selection or co-ligand thereof, e.g., P-selectin, E-selectin (ELAM), I-selectin, P-selectin glycoprotein-1 (PSGL-1). In certain embodiments the polynucleotide inhibits a component of the complement system, e.g., C3, C5, C3aR, C5aR, C3 convertase, and C5 convertase, a chemokine or receptor thereof, e.g., TNFI, TNFJ, IL-1I, IL-1J, IL-2, IL-2R, IL-4, IL-4R, IL-5, IL-6, IL-8, TNFRI, TNFRII, IgE, SCYA11, and CCR3, or GCSF, Gro1, Gro2, Gro3, PF4, MIG, Pro-Platelet Basic Protein (PPBP), MIP-1I, MIP-1J, RANTES, MCP-1, MCP-2, MCP-3, CMBKR1, CMBKR2, CMBKR3, CMBKR5, AIF-1, or I-309.

In some aspects the polynucleotides provided can treat a subject at risk for or afflicted with a neurological disease or disorder. In some embodiments the disease or disorder is Alzheimer Disease or Parkinson Disease. In certain embodiments the polynucleotide inhibits an amyloid-family gene, e.g., APP; a presenilin gene, e.g., PSEN1 and PSEN2, or I-synuclein. In other embodiments the disease or disorder is a neurodegenerative trinucleotide repeat disorder, e.g., Huntington disease, dentatorubral pallidoluysian atrophy or a spinocerebellar ataxia, e.g., SCA1, SCA2, SCA3 (Machado-Joseph disease), SCA7 or SCA8. In some embodiments the polynucleotide inhibits HD, DRPLA, SCA1, SCA2, MJD1, CACNL1A4, SCA7, or SCA8.

In certain aspects, the nanoparticles herein comprise an polynucleotide capable of cleaving or inhibits more than one gene. In these embodiments the polynucleotide is selected so that it has sufficient homology to a sequence found in more than one gene, e.g. a sequence conserved between these genes. Thus in some embodiments an polynucleotide targeted to such sequences effectively silences the entire collection of genes. In some embodiments the nanoparticles are provided with two or more types of polynucleotides, wherein the polynucleotides inhibit different genes of the same disease or different diseases.

The presently-disclosed subject matter is further illustrated by the following specific but non-limiting examples. The following examples may include compilations of data that are representative of data gathered at various times during the course of development and experimentation related to the present invention.

EXAMPLES

Example 1

This Example describes the synthesis and characterization of a PEG-(DMAEMA-co-BMA) polymer. For this Example, all materials were obtained from Sigma-Aldrich (St. Louis, Mo.) and were used as received unless otherwise noted. An alumna column was utilized to remove inhibitors from DMAEMA and BMA monomers, and final purification of polymers was done with PD10 desalting columns (GE Healthcare, Waukesha, Wis.).

First a 4-cyano-4-(ethylsulfanylthiocarbonyl) sulfanylpentanoic acid (ECT) and PEG-ECT was synthesized. To achieve this, the reversible addition fragmentation chain transfer (RAFT) chain transfer agent (CTA) ECT was synthesized, and the R-group of the CTA was subsequently conjugated to PEG. Briefly, dicyclohexylcarbodimide (DCC, 4 mmol, 0.82 g) was added to the stirring solution of mono methoxy-poly(ethylene glycol) (Mn=5000, 2 mmol, 10 g), ECT (4 mmol, 1.045 g), and DMAP (10 mg) in 50 mL of dichloromethane. The reaction mixture was stirred for 48 h. The precipitated cyclohexyl urea was removed by filtration and dichloromethanane layer was concentrated and precipitated into diethyl ether twice. The precipitated PEG-ECT was washed three times with diethyl ether and dried under vacuum (Yield ~10 g). $^1$H NMR (400 MHz CDCL$_3$) revealed 91% substitution of the PEG (FIG. 1).

Figure 2:
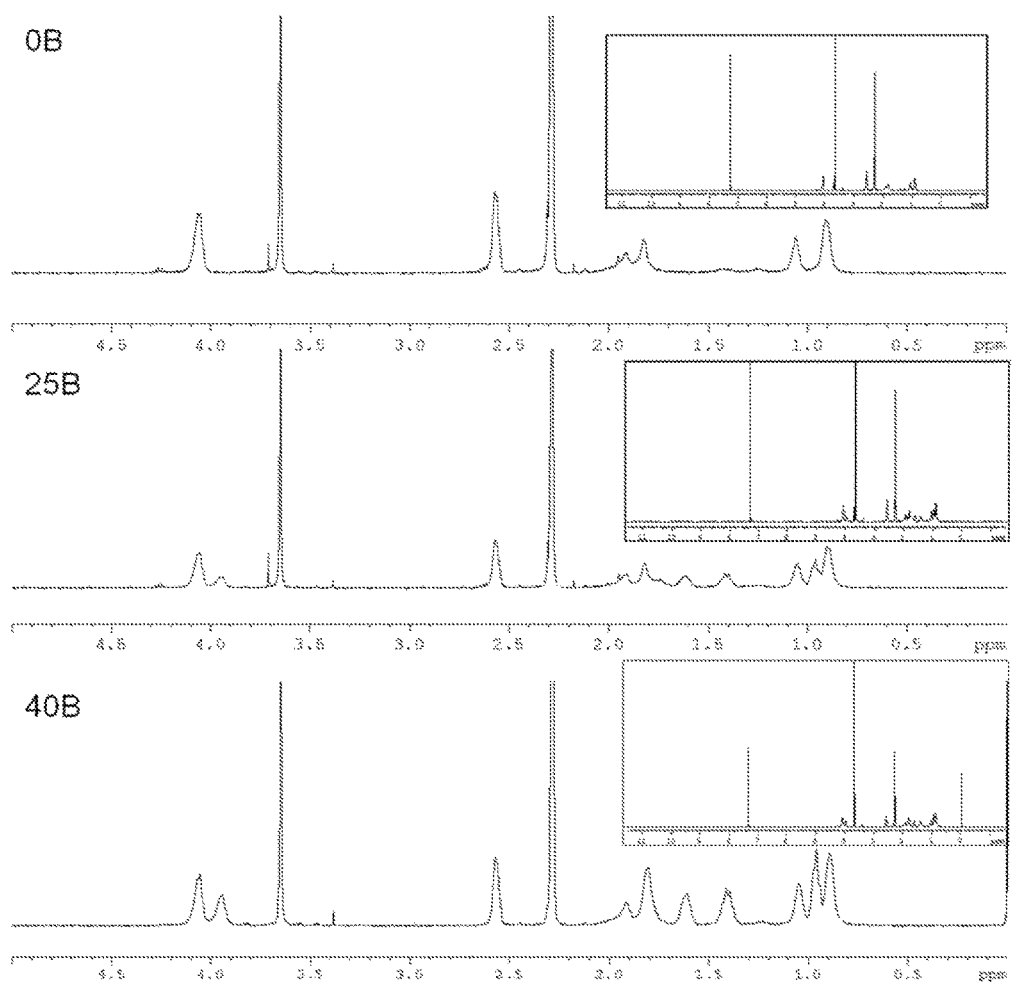
FIG. 2 includes NMR spectra of a polymer panel showing the analysis by $^1H$ NMR (400 MHz, $CDCl_3$), which were used to quantify molecular weight by integrating the $\delta$ 3.65 s ($—OCH_2CH_2—$) PEG peak and comparing to the $\delta$ 2.58 s ($—CH_2NH_2$) of the DMAEMA, the $\delta$ 4.05 s ($—O—CH_2CH_2—$) of the DMAEMA and the $\delta$ 3.95 s ($—O—CH_2CH_2—$) of the BMA.
Figure 3:
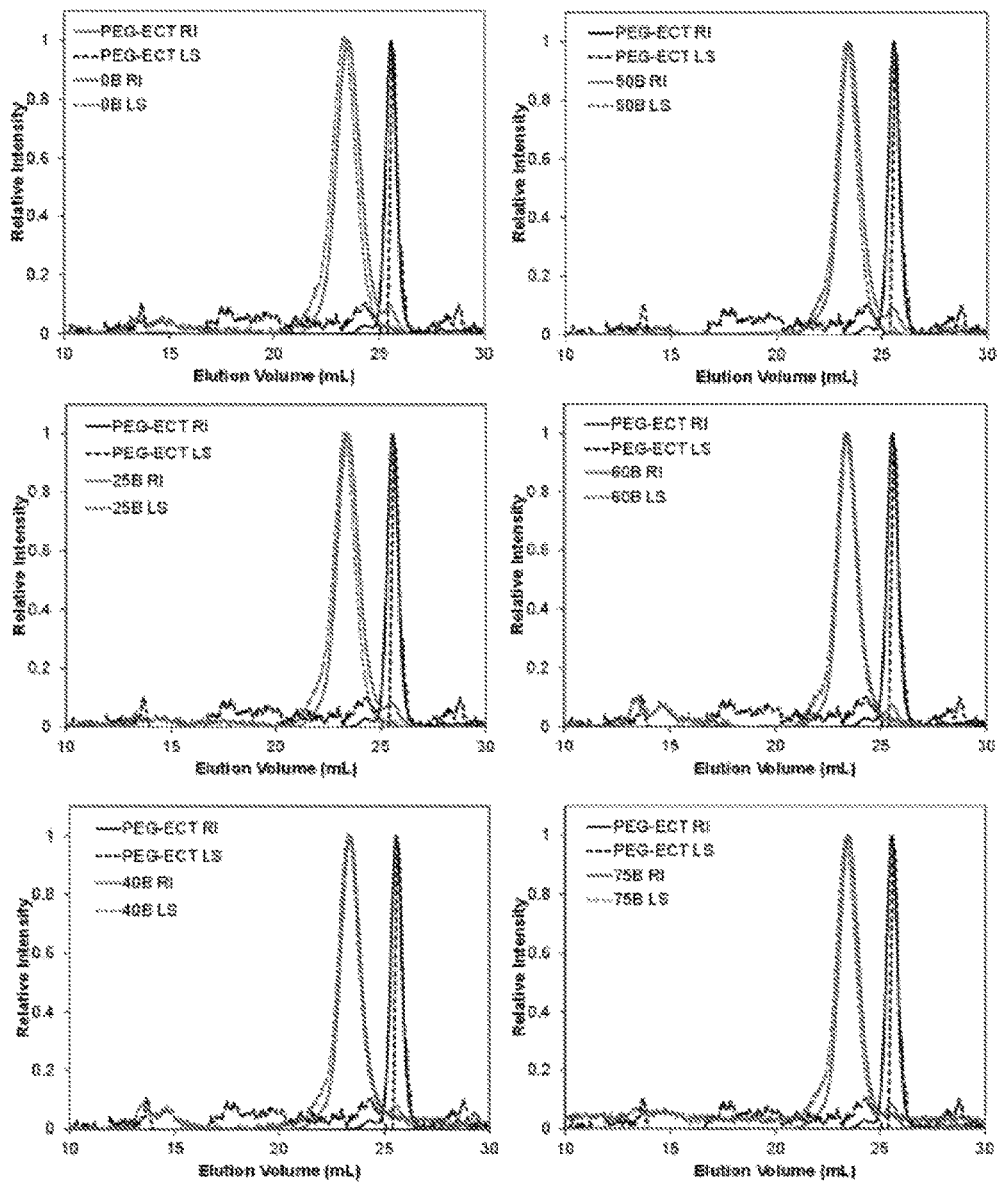
FIG. 3 includes plots showing the molecular weight and polydispersity obtained by GPC, where the molecular weights were quantified with an inline light scattering (dotted lines) and refractive index (solid lines) detectors using calculated dn/dc values determined offline.

Thereafter, RAFT polymerization was used to synthesize a library of copolymers using the PEG-ECT macro-CTA. In all cases, the degree of polymerization (DP) was 150, and the monomer plus CTA was 40% wt/vol in dioxane. The polymerization reaction was carried out at 70° C. for 24 h using AIBN as the initiator with a 5:1 [CTA]:[Initiator] molar ratio. A series of polymerizations were carried out with monomer feed ratios of 0:100 (B0), 25:75 (B25), 40:60 (B40), 50:50 (B50), 60:40 (B60), and 75:25 (B75) mol % [BMA]:[DMAEMA] (Table 1). The reaction was stopped by exposing the polymerization solution to air, and the resulting diblock polymers were precipitated into an excess of pentane. The isolated polymers were vacuum dried, re-dissolved in water, further purified using PD10 columns, and lyophilized. Polymers were characterized for composition and molecular weight by $^1$H nuclear magnetic resonance spectroscopy (NMR; 400 Mhz Spectrometer equipped with 9.4 Tesla Oxford magnet, Bruker Biosciences Corp., Billerica, Mass.;). Absolute molecular weight of the polymers was determined using DMF mobile phase gel permeation chromatography (GPC; Agilent Technologies, Santa Clara, Calif.) with inline Agilent refractive index and Wyatt miniDAWN TREOS light scattering detectors (Wyatt Technology Corp., Santa Barbara, Calif.). All results are shown in FIGS. 2 and 3.

TABLE 1

Molecular weight and percent composition of the polymer library

| Polymer Name (% BMA in feed) | Mn(g/mol) | PDI | % BMA | % DMAEMA |
|---|---|---|---|---|
| 0B | 17035 | 1.092 | 0.0 | 100.0 |
| 25B | 18747 | 1.075 | 23.8 | 76.2 |
| 40B | 20765 | 1.117 | 39.6 | 60.4 |
| 50B | 18040 | 1.040 | 48.3 | 51.7 |
| 60B | 19938 | 1.081 | 58.6 | 41.4 |
| 75B | 17349 | 1.053 | 74.5 | 25.5 |

Figure 4:
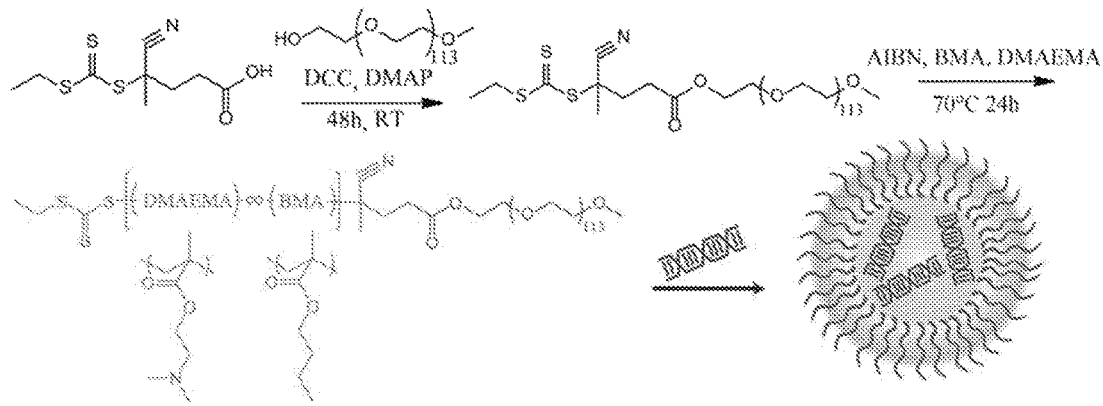
FIG. 4 includes a schematic of the synthesis of PEG-(DMAEMA-co-BMA).

A schematic of the synthesis of the pH-responsive diblock copolymers synthesized from PEG$_{5K}$ macro-CTA using RAFT polymerization is shown in FIG. 4. The synthesis completed by the RAFT polymerization technique resulted in all the polymers having a polydispersity ($M_w/M_n$) of less than or equal to about 1.1. The single step polymerization was a *facile* and scalable synthesis that yielded purified polymers with composition and molecular weight that closely matched the targeted values.

Example 2

This Example describes methods for making nanoparticles in the absence of siRNA and utilizing the polymer synthesized in Example 1. This Example further describes certain properties and characteristics of the exemplary nanoparticles.

Each lyophilized polymer was dissolved in 100% ethanol, and aliquots of this solution were mixed with an 8-fold excess of phosphate buffer at pHs 7.4, 7.1, 6.8, 6.2, 5.6, and 5.2 or citrate buffers of pH 4.6 and 4.0 to make a 1 mg/mL stock solution. Each stock solution was diluted an additional 10-fold into phosphate or citrate buffer of the same pH to form 100 μg/mL polymer stocks. Next, formulation conditions for siRNA packaging were assessed by observing the pH-dependence of self-assembly of each polymer into nanoparticles using dynamic light scattering (DLS; Malvern Zetasizer Nano ZS, Malvern, UK).

For imaging by transmission electron microscopy (TEM), carbon film-backed copper grids (Electron Microscopy Sciences, Hatfield, Pa.) were inverted onto droplets containing aqueous nanoparticle suspensions (1 mg/mL) and blotted dry. Next, samples were inverted onto a droplet of 3% uranyl acetate, allowed to counterstain for 2 min, and again blotted dry. Finally, samples were desiccated in vacuo for 2 h prior to imaging on a Philips CM20 system operating at 200 kV (Philips, EO, Netherlands).

Figure 5A:
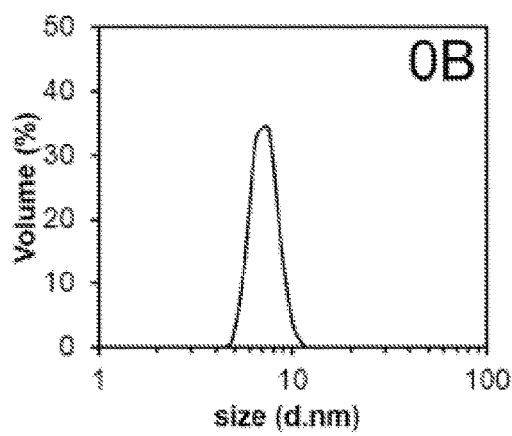
FIG. 5 includes dynamic light scattering (DLS) measurements showing the pH-dependent assembly/disassembly behavior of PEG-(DMAEMA-co-BMA)] polymers for decreasing pH values down to pH 4.0 or until full nanoparticle disassembly occurred with polymers comprising A) 0% BMA, B) 25% BMA, C) 40% BMA, D) 50% BMA, E) 60% BMA, and F) 75% BMA in the (DMAEMA-co-BMA) block. The inset in FIG. 5D shows transmission electron microscopy (TEM) of a 50B polymer at pH 7.4 forming spherical nanoparticles (scale bar=100 nm)
Figure 5B:
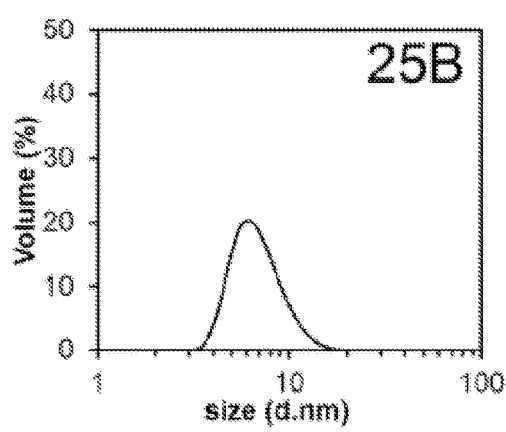
Figure 5C:
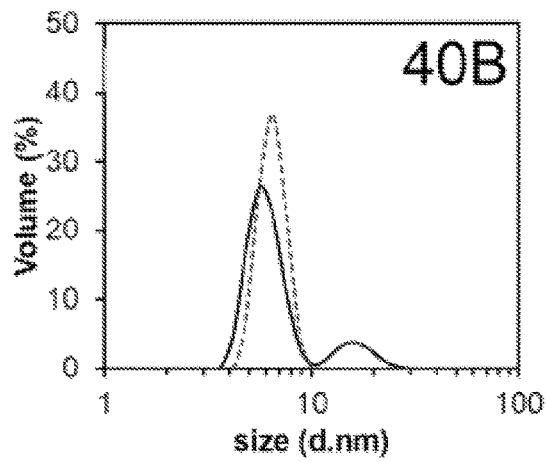
Figure 5D:
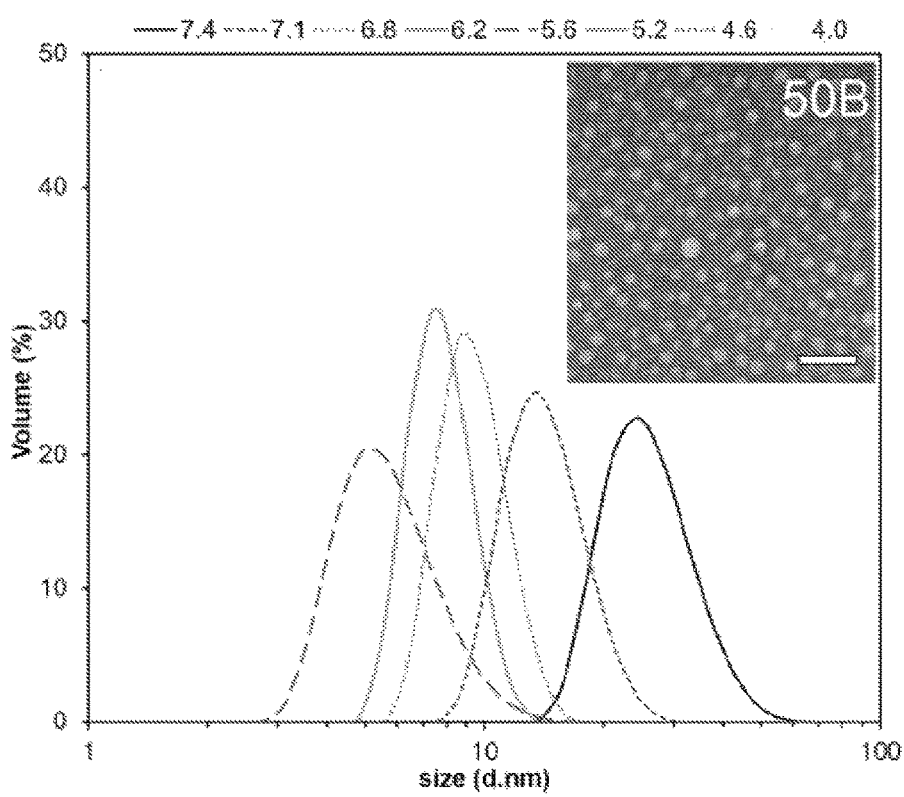
Figure 5E:
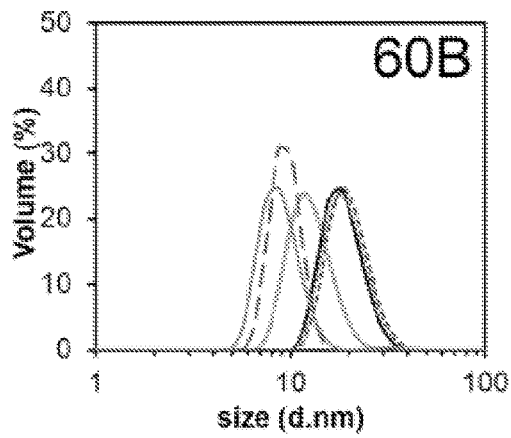
Figure 5F:
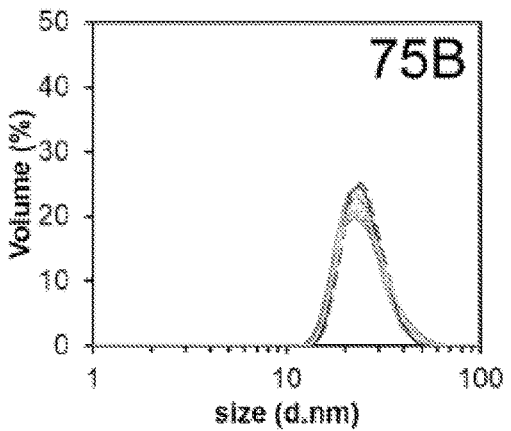

The relative acidity required to trigger polymer micelle disassembly was directly related to the % BMA content in the poly(DMAEMA-co-BMA) block. The 0B and 25B polymers did not spontaneously form nanoparticles at any pH tested, while polymers with 50% or more BMA content formed nanoparticles (~25 nm diameter, FIG. 5) at pH 7.4, with the 40B polymer appearing to be in a transition state at this pH. The 40B, 50B, and 60B polymeric micelles dissociated as the pH was lowered, and the pH where this transition occurred was inversely proportional to the % BMA in the polymer (FIGS. 5C to 5E). TEM images visually confirmed nanoparticle assembly for 50B at pH 7.4 (FIG. 5D inset). The 75B polymer remained in a stable nanoparticle state at all pHs tested (FIG. 5F).

Example 3

This Example describes methods for making nanoparticles that are loaded with siRNA and utilizing the polymer synthesized in Example 1. This Example further describes certain properties and characteristics of the exemplary siRNA-loaded nanoparticles.

siRNA-loaded nanoparticles were made by mixing solutions of polymer and siRNA at N:P ratios of 5, 7, 10, or 20 and at pH 5.2. The final charge ratio was calculated as the molar ratio of cationic amines on the DMAEMA (50% are assumed for this Example to be protonated at physiologic pH) to the anionic phosphates on the siRNA. After mixing, these solutions were diluted 5-fold to 100 µL with phosphate buffer to adjust the final pH to 7.4. It appeared that the N:P ratio required to fully complex siRNA was proportional to the % BMA in the polymer.

After mixing, samples were incubated for 30 minutes, and 15 ng siRNA for each sample was loaded onto a 4% agarose gel containing ethidium bromide to assess siRNA packaging efficiency. The gels were run at 100 volts for 35 minutes and imaged with a UV transilluminator. Quantification was conducted using ImageJ version 1.45 s (Freeware, NIH, Bethesda, Md.). Hydrodynamic diameter and zeta potential of the resulting nanoparticles were measured using a Malvern Zetasizer Nano ZS.

Figure 6A:
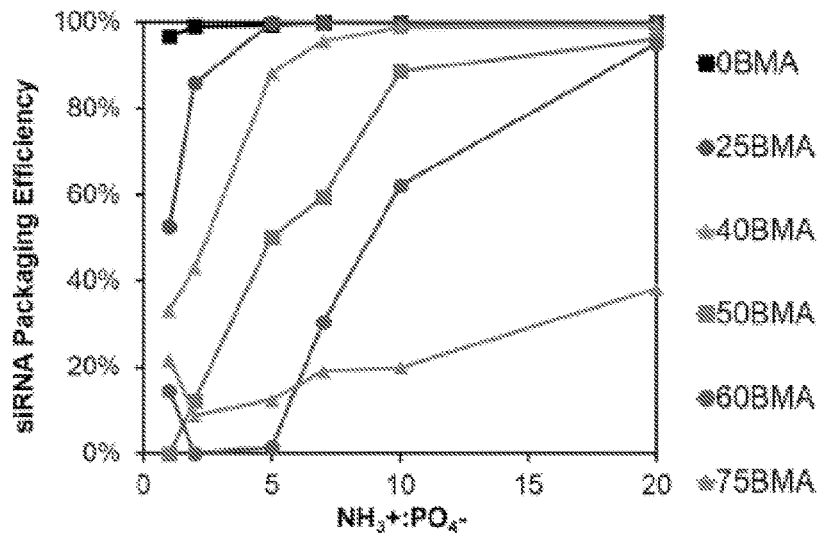
FIG. 6 includes plots and images showing the formulation of siRNA nanoparticles at pH 5.2, where A) shows siRNA packaging efficiency for different polymer compositions and N:P ratios, and B) shows gel images quantifying siRNA packaging efficiency.
Figure 6B:
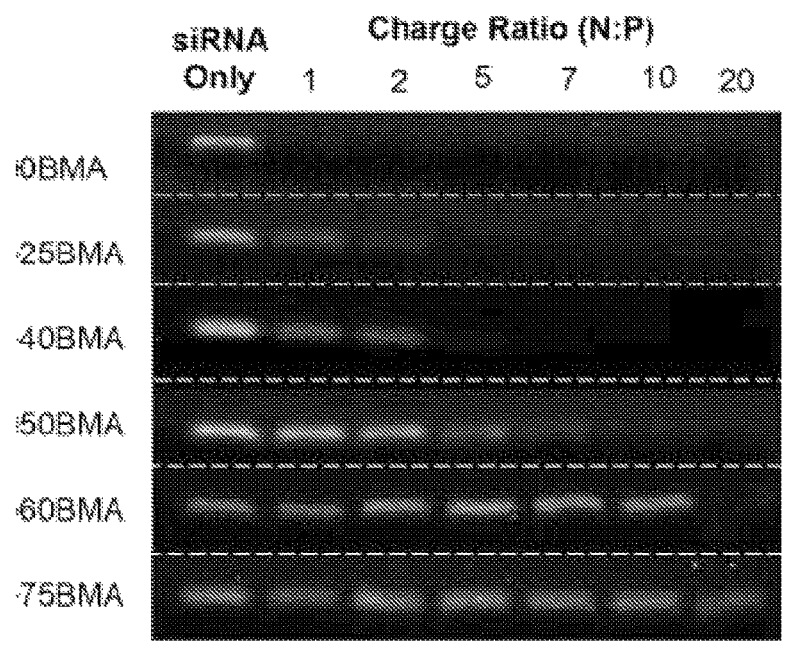
Figure 7:
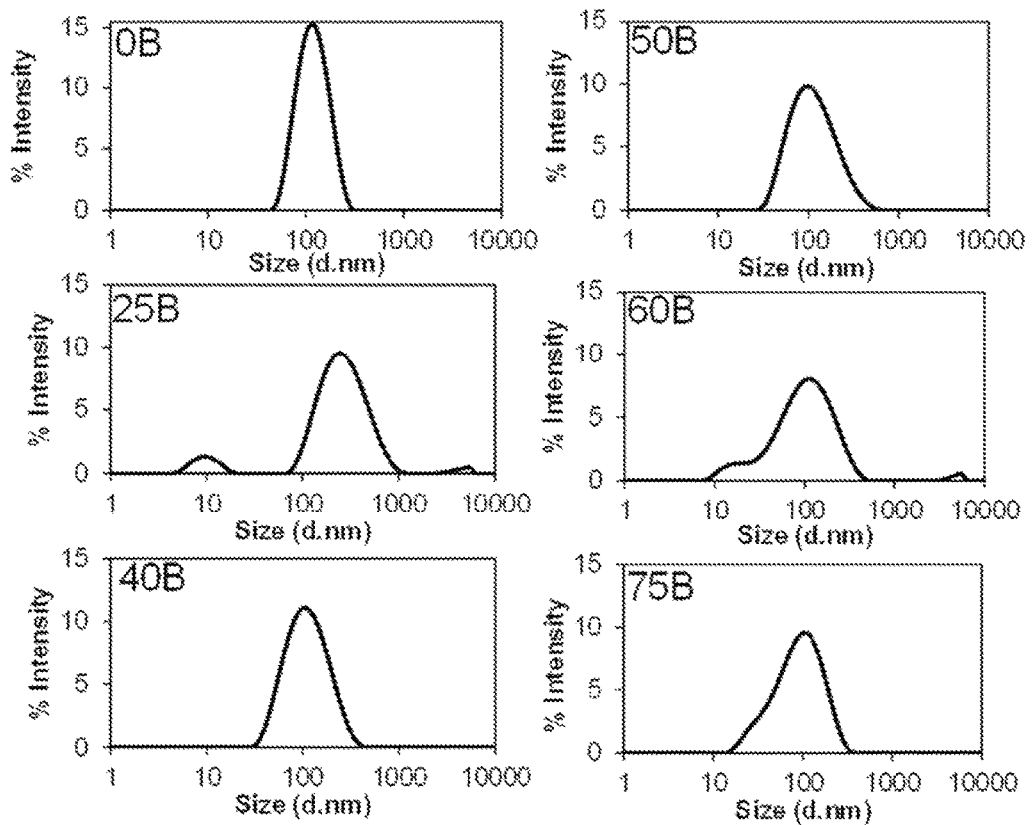
FIG. 7 includes DLS for siRNA nanoparticles at a charge ratio (N:P) of 10:1 showing that the nanoparticles are relatively monodispersed and centered around about 100 nm, and zeta potential measurements for 40B and 50B were −1.05±6.1 mV and −0.9±6.6 mV, respectively.
Figure 8:
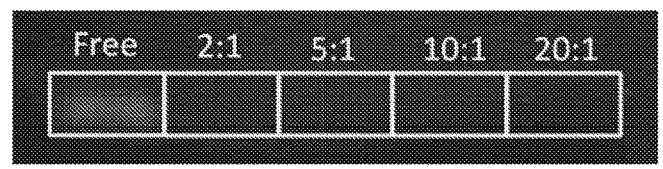
FIG. 8 includes an image showing 82%, 88%, 93% and 97% siRNA complexation by 50B nanoparticles at pH 4.0 comprising a N:P ratios of 2:1, 5:1, 10:1, and 20:1, respectively.

Agarose gel electrophoretic mobility shifts showed the percent siRNA packaging efficiency achieved using different formulation conditions (FIG. 6). Polymers 40B and 50B were able to package siRNA at least at an N:P of 10 or greater. The nanoparticles formed from all polymers at N:P of 10:1 had a hydrodynamic diameter of about 100 nm and approximately neutral zeta potential (FIG. 7). It was also found that siRNA complexed on the 50B polymers at pH to 4.0 and at a charge ratio of 5:1 (FIG. 8). Thus, in certain embodiments siRNA packaging efficiency depended on the surrounding solution's pH.

Example 4

This Example characterizes the behavior the nanoparticles of the previous Examples in vitro. In particular, this Example describes the cellular uptake, gene silencing, cytotoxicity, and endolysosomal escape properties of the exemplary nanoparticles.

Human epithelial breast cancer cells (MDA-MB-231) were cultured in Dulbecco's Modified Eagle's Medium (DMEM, Gibco Cell Culture, Carlsbad, Calif.) supplemented with 10% Fetal Bovine Serum (FBS, Gibco) and 0.1% gentamicin (Gibco). Mouse Embryonic Fibroblasts (NIH3T3) were cultured in Dulbecco's Modified Eagle's Medium (DMEM, Gibco) supplemented with 10% Bovine Calf Serum (BCS, Gibco) and 1% penicillin-streptomycin (Gibco).

The MDA-MB-231 breast cancer cells were seeded in 24-well plates at a density of 40,000 cells/cm$^2$ and allowed to adhere overnight. The cells were treated with nanoparticles loaded with Alexa488-labeled DNA (21mer duplexes mimicking siRNA molecules) at a final concentration in each well of 100 nM in media supplemented with 10% FBS. After the designated treatment time, cells were washed with PBS and trypsinized Cells were centrifuged and resuspended in PBS containing trypan blue to quench extracellular fluorescence. Relative cell fluorescence was quantified via flow cytometry to measure nanoparticle intracellular delivery (FACSCalibur, BD Biosciences, Franklin Lakes, N.J.).

Figure 9A:
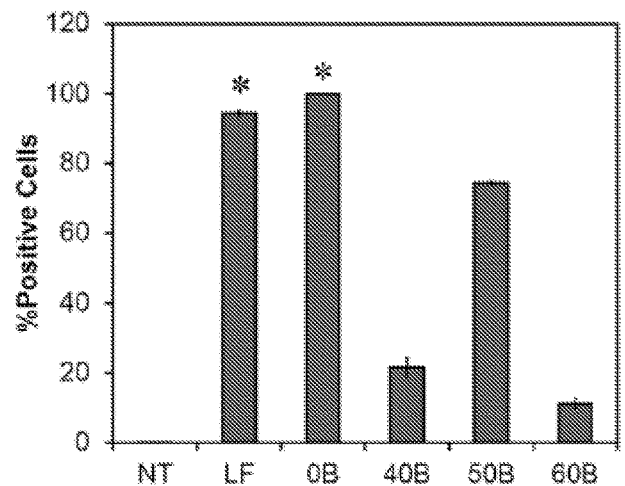
FIG. 9 includes plots for 50B-based nanoparticles in vitro showing A) flow cytometry measurement of transfection efficiency, B) bioluminescence measurement of luciferase knockdown, and C) cytotoxicity measurements. NT=no treatment, LF=Lipofectamine 2000, Statistical significance evaluated by ANOVA at p<0.05.

Flow cytometry revealed that the exemplary 0B nanoparticles had the highest uptake and transfected nearly 100% of the cells, and the exemplary 50B nanoparticles were internalized more than the exemplary 40B or 60B nanoparticles (FIG. 9A).

To determine gene silencing efficiency, the MDA-MB-231 breast cancer cells were transduced with a lentivirus to constitutively express luciferase (L231). L231 cells were seeded in black, clear bottom 96 well plates at a density of 12,500 cells/cm$^2$ and allowed to adhere overnight. Next, cells were treated for 24 h with nanoparticles containing anti-luciferase siRNA (Ambion, Life Technologies, Carlsbad, Calif.) in 10% FBS media. Media was then replaced with luciferin-containing media (150 µg/mL), and bioluminescence was measured using an IVIS 200 Series imaging system (Xenogen). Next, cells were incubated for an additional 24 h in slow growth media (DMEM supplemented with 1% FBS, and 0.1% gentamicin), and bioluminescence was subsequently re-measured. Bioluminescence data was normalized to total protein content in cell lysates which was measured via the Bradford assay (Bio-Rad Laboratories, Inc., Hercules, Calif.).

Figure 9B:
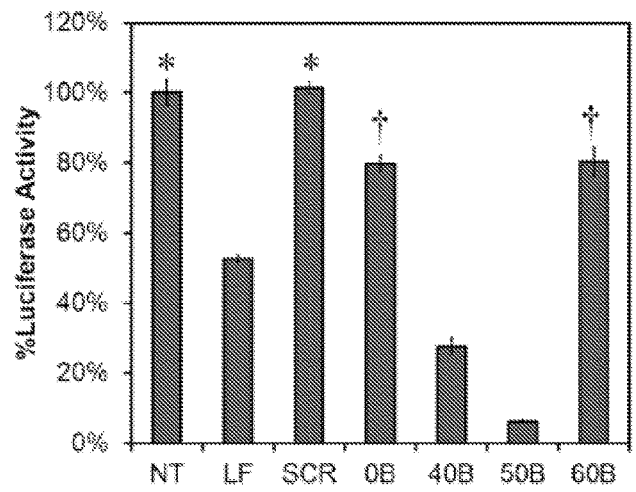
Figure 9C:
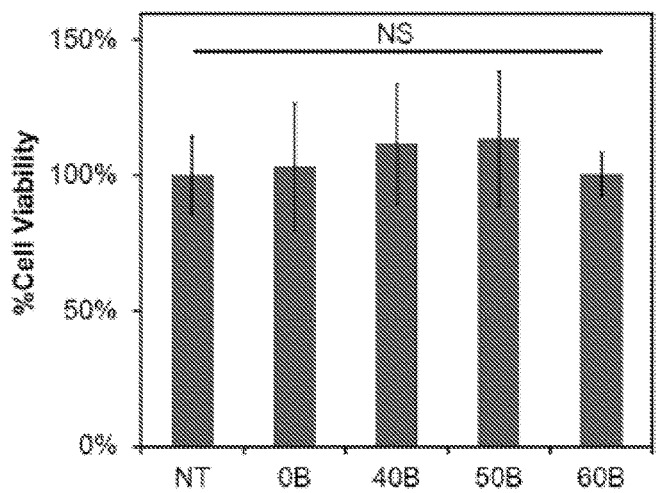
Figure 10:
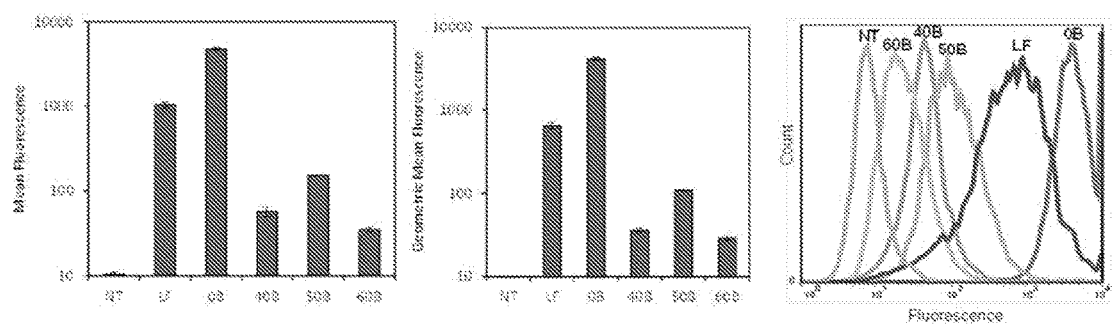
FIG. 10 includes plots of flow cytometry for nanoparticles comprising different polymer chemistry showing cellular uptake in MDA-MB-231 cells. (n=3)
Figure 11:
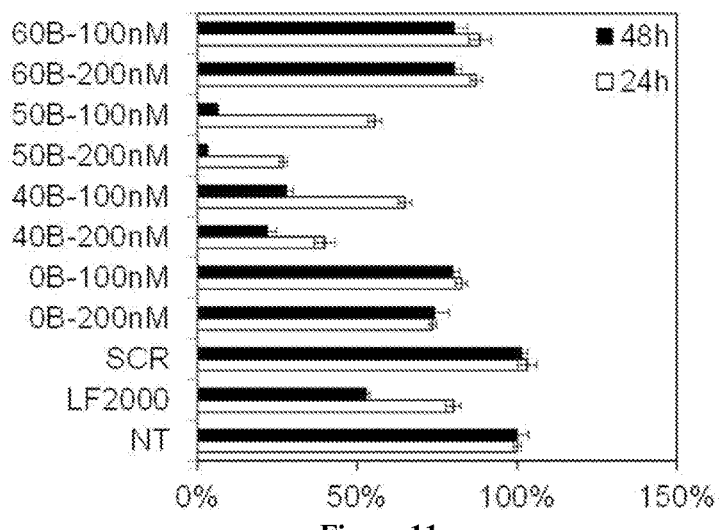
FIG. 11 includes a plot showing luciferase protein level silencing in L231 cells for nanoparticles comprising different polymer compositions and siRNA doses.
Figure 12:
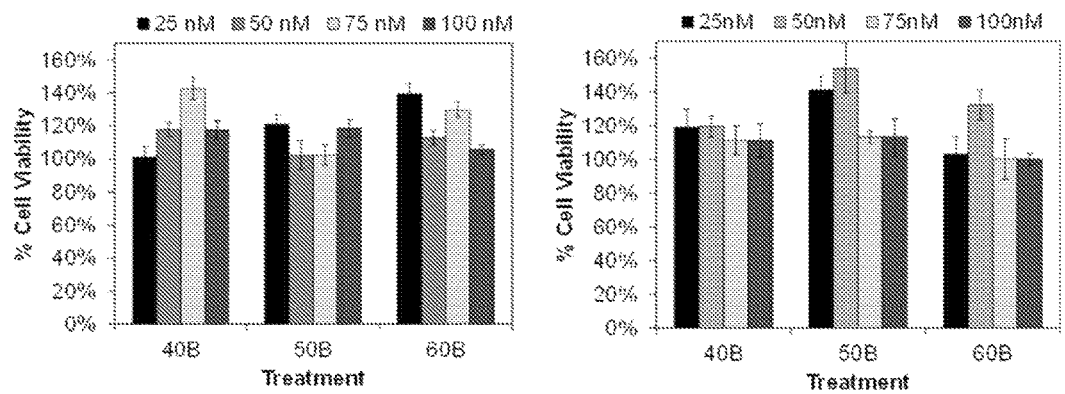
FIG. 12 includes plots showing full panel of cytotoxicity measurements on LR3T3 cells for nanoparticles comprising the 40B, 50B, and 60B polymers at 24 h (left panel) and 48 h (right panel).

The nanoparticles showed luciferase silencing (FIG. 9B), and luciferase silencing of the 50B nanoparticles showed a 94% reduction in the protein level at 48 h when compared to scrambled control siRNA in MDA-MB-231 breast cancer cells transduced to constitutively express luciferase. The benchmark 0B formulation produced 20% luciferase silencing (FIG. 9B, $p<0.05$). Without being bound by theory or mechanism, the gene silencing activity of 50B nanoparticles suggests that they are efficient in navigating intracellular delivery barriers (i.e., increased cytoplasmic release) relative to 0B nanoparticles.

Next, cytotoxicity of siRNA-loaded nanoparticles was determined by measuring relative cell number based on luciferase activity. NIH3T3s were transduced with a lentivirus to constitutively express luciferase (LR-3T3s), and it was confirmed that cell number was directly proportional to luciferase signal. LR-3T3s were seeded in black-walled 96-well plates at a density of 12,500 cells/cm$^2$ and allowed to adhere overnight. Cells were treated with fresh nanoparticles at concentrations of 50, 100, and 200 nM siRNA/well (100 µL volume, n=5 for each treatment). After incubation for 24 h, the cells were given fresh luciferin-containing media (150 µg/mL). Bioluminescence was quantified using an IVIS Imaging System 200 series (Xenogen).

Treatment with the nanoparticles was substantially and/or wholly nontoxic to the MDA-MB-231 cells (not shown) and NIH3T3 fibroblasts at the concentrations used in the gene silencing procedures (FIGS. 9C, 10, 11, and 12).

Example 5

This Example characterizes the endo-lysosomal escape properties of the nanoparticles of the previous Examples in vitro.

Figure 13A:
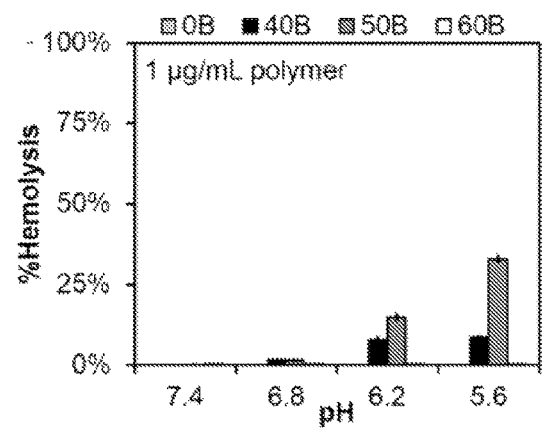
FIG. 13 includes plots and images showing siRNA loaded nanoparticle endosome disruption and escape where plots of percent hemolysis at different pH for nanoparticles made at N:P of 10:1 and comprising different polymers are shown for A) 1 µg/mL, B) 5 µg/mL and C) 40 µg/mL polymer, where D-E) show confocal images of colocalization of the endosome/lysosome dye Lysotracker® with the cy5-labeled dsDNA cargo (colocalization graphs shown as insets), and where F) shows % colocalization of dsDNA cargo with lysosomes relative to Lipofectamine2000 for 50B nanoparticles (* signifies p<0.01).
Figure 13B:
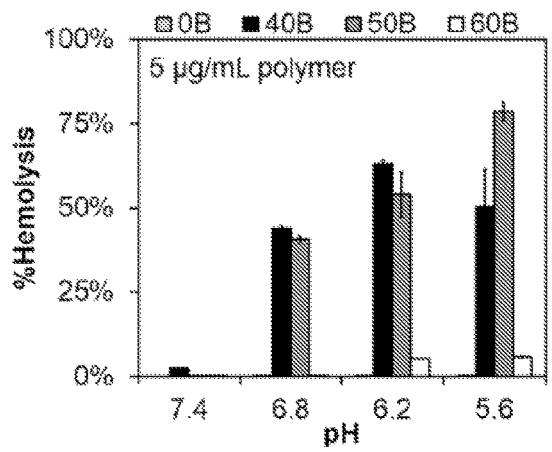
Figure 13C:
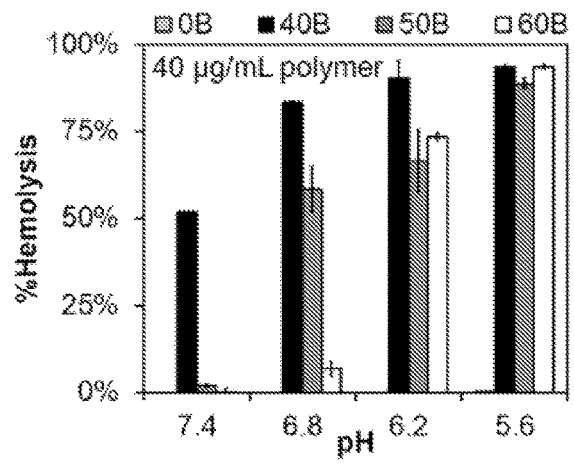

To characterize endosomal escape behavior, the pH-dependent membrane disruptive activity of siRNA-loaded nanoparticles was measured using a red blood cell hemolysis assay. At all the N:P ratios tested, nanoparticles comprised of the 40B, 50B, and 60B polymers generated switch-like, pH-dependent membrane disruption. Percent hemolysis of each polymer increased as the polymer concentration was increased and as the buffer pH was decreased. The pH where the hemolytic transition occurred mirrored the trend seen for destabilization of polymer nanoparticles (FIG. 5) and was inversely dependent on the % BMA content in the poly (DMAEMA-co-BMA) block (FIGS. 13A to 13C).

Figure 14:
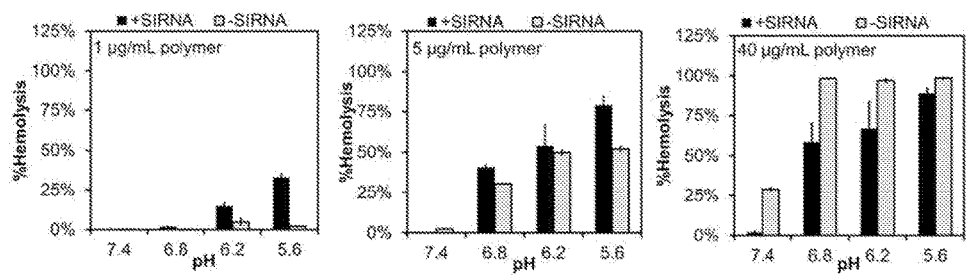
FIG. 14 includes plots of percent hemolysis showing the red blood cell disruptive behavior of free 50B polymer and of 50B siRNA-loaded nanoparticles.
Figure 15:
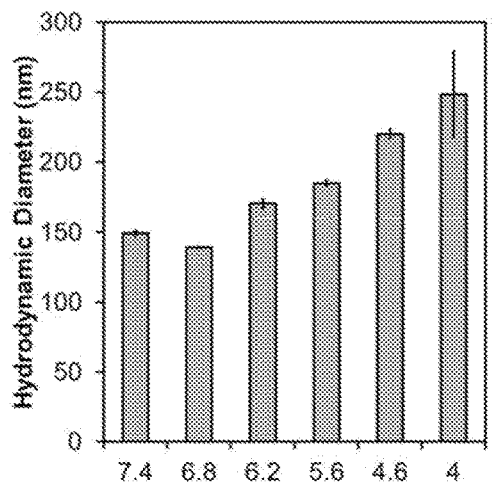
FIG. 15 includes a plot of nanoparticle hydrodynamic diameter at different pH for 50B nanoparticles ($NH_3$/$PO_4$=10/1).
Figure 16A:
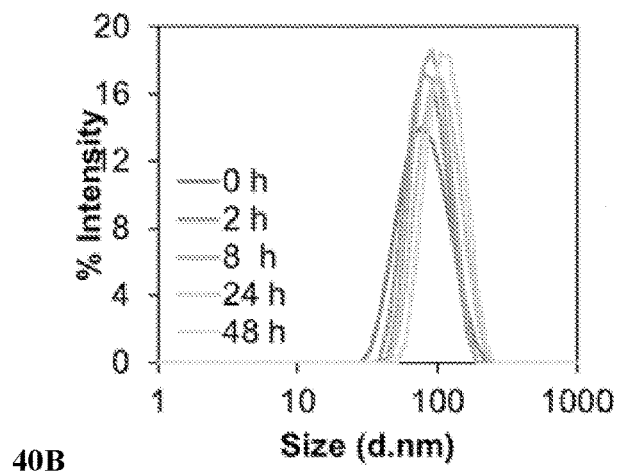
FIG. 16 includes plots, where A-C) show nanoparticles evaluated for stability by incubating in PBS and measuring the size over 48 h, and D) shows FRET measured at 48 h revealing 88% retention of the FRET signal.
Figure 16B:
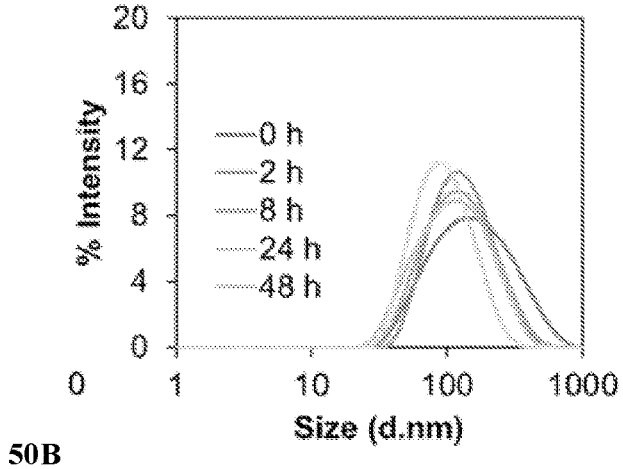
Figure 16C:
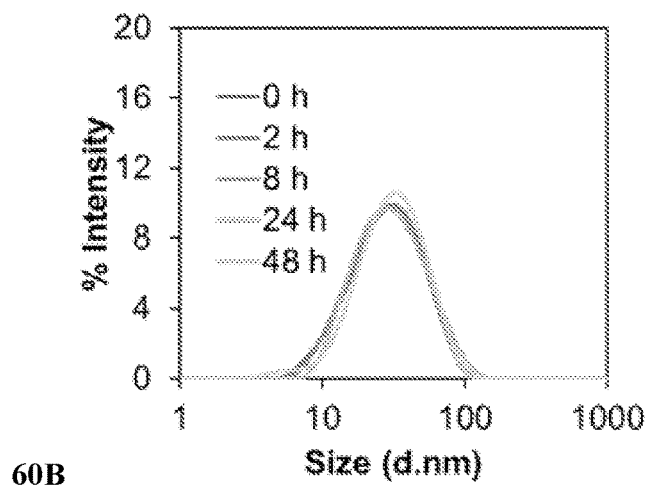
Figure 16D:
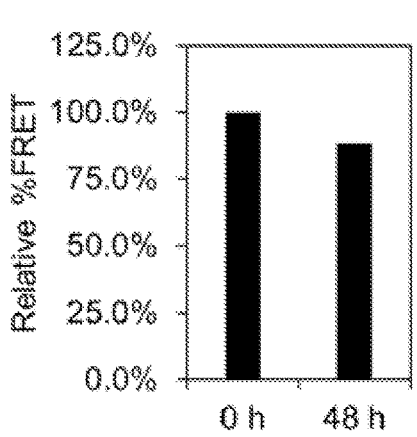

It was further observed that the pH-dependent membrane disruptive behavior of the 50B polymer comprising nanoparticles was similar between the polymer-only nanoparticles and the siRNA loaded nanoparticles (FIG. 14). Without being bound by theory or mechanism, this suggests that presence of the anionic siRNA did not inhibit pH-dependent destabilization and exposure of the membrane disruptive poly(BMA-co-DMAEMA) block of nanoparticles exposed to acidic pH. Although the nanoparticles did not fully disassemble like the polymer-only nanoparticles, the siRNA comprising nanoparticles' hydrodynamic diameter increased (i.e., at least partial disassembly) upon exposure to buffers of decreasing pH, suggesting that swelling and/or reorganization of the nanoparticle structure leads to exposure of the core-forming block under such conditions (FIG. 15).

To assess intracellular trafficking and endo-lysosomal escape, confocal microscopy was used to measure colocalization with the fluorescent dye Lysotracker® (Life Technologies). More specifically, MDA-MB-231 cells were seeded at a density of 12,500 cells/cm$^2$ in 8-well chamber slides (Nunc—Thermo Fisher Scientific Inc., Waltham, Mass.). The cells were treated with cy5-labeled dsDNA loaded nanoparticles at 100 nM or Lipofectamine 2000 according to manufacturer's specifications. After treatment, media was replaced with Lysotracker® (Invitrogen Life Technologies, Grand Island, N.Y.) containing media (75 nM), and cells were incubated for 1 h before imaging with confocal microscopy (Zeiss LSM 710Meta, Oberkochen, Germany) equipped with differential interference contrast (DIC). Images were analyzed using ImageJ with a colocalization extension.

Figure 13D:
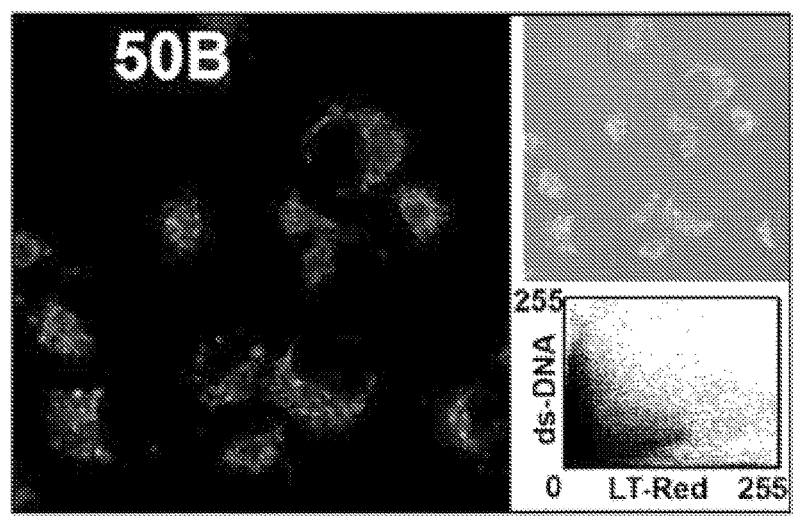
Figure 13E:
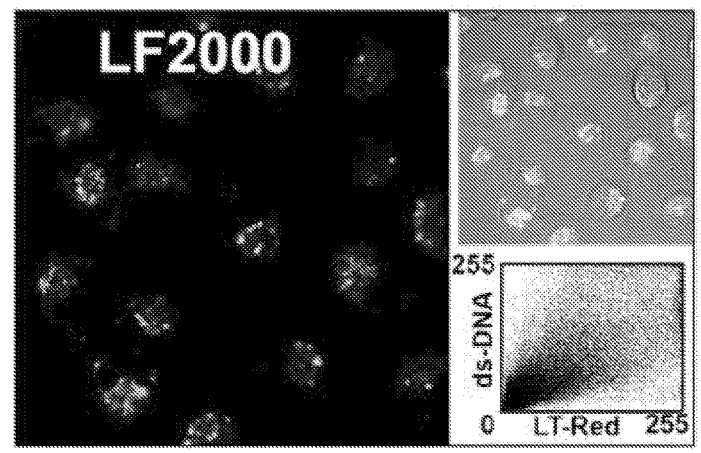
Figure 13F:
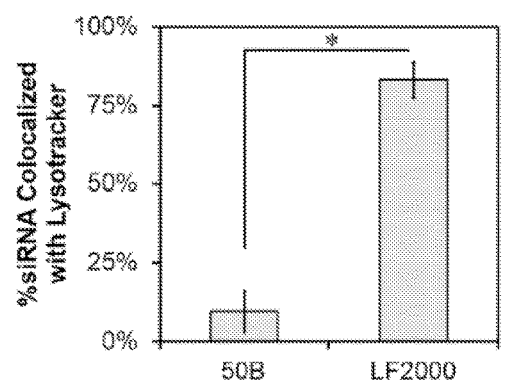

Diffuse staining of the cy5-labeled dsDNA cargo was visualized in cells incubated with 50B nanoparticles for 24 h (FIG. 13D), and 50B nanoparticle delivery resulted in significantly lower Lysotracker® colocalization relative to Lipofectamine (colocalization appears yellow, FIG. 13E). The colocalization was further visualized by plotting color values of non-background image pixels in a dot plot where colocalized signal falls on the y=x line, free siRNA falls on the y-axis, and lysosomes not containing siRNA fall on the x-axis (inset graphs). These combined data quantitatively and qualitatively suggest that nanoparticles are able to efficiently overcome intracellular endo-lysosomal delivery barriers.

Example 6

This Example characterizes the stability and hemocompatibility of the nanoparticles of the previous Examples in vitro and ex vivo.

Whole blood was extracted from anonymous, consenting human donors and red blood cells (RBCs) were isolated according to well established protocols. RBCs were then incubated with the free polymers or with siRNA-loaded nanoparticles (concentrations ranging 1-40 μg/mL) in buffers of pH 7.4, 6.8, 6.2, and 5.6, which model the environments in the extracellular space and in the more acidic vesicles of the endo-lysosomal pathway. After 1 h of incubation, the RBCs were centrifuged and the supernatant was spectrophotometrically analyzed at 451 nm in order to determine percent hemolysis relative to Triton X-100 detergent.

Also, nanoparticles were loaded with Förster Resonance Energy Transfer (FRET, using FAM and Cy5) pair-labeled 23mer dsDNAs (a model for siRNA) (FRET—nanoparticles). Fluorescent intensity was measured using a spectrophotofluorometer with an excitation wavelength of 488 nm (Jobin Yvon/Horiba Fluorolog-3 FL3-111, Horiba Scientific, Kyoto Japan). FAM emission was collected at 520 nm±3 nm, and Cy5 emission was obtained at 670 nm±3 nm. % FRET was calculated as a ratio of the fluorescent intensity as follows:

$$\% \ FRET = \frac{I_{670}}{I_{520} + I_{670}}. \qquad \text{Eqn. 1}$$

For serum stability measurements, FRET-nanoparticles were added into human whole blood diluted 1:3 in PBS at 100 nM (50 nM for each DNA). Treated blood samples were loaded into a black, round bottom 96 well plate and placed on a shaker for 5 minutes before incubating at 37° C. for 1 h. Plates were then centrifuged at 500×g for 5 minutes, and then 50 μL of supernatant (diluted blood serum) from each well was transferred into a black, clear bottom 96 well plate. Fluorescence was measured using a Microplate Reader and % FRET was calculated using Eqn 1. In parallel experiments to assess hemocompatibility ex vivo, nanoparticles loaded with FAM-labeled dsDNA were used to quantify the percent of nanoparticles in the supernatant, as a measure of inertness, or ability to reduce nonspecific adsorption to or aggregation with RBCs.

Loaded nanoparticles made with 40B, 50B, and 60B were stable and did not aggregate or dissociate over a period of 24 h in PBS as assessed with DLS (FIG. 16). Also, FRET-nanoparticles made with 50B also retained an equivalent % FRET after 48 hours of storage at room temperature, further indicating that siRNA remains stably encapsulated in the core of the nanoparticles (FIG. 16).

Figure 17A:
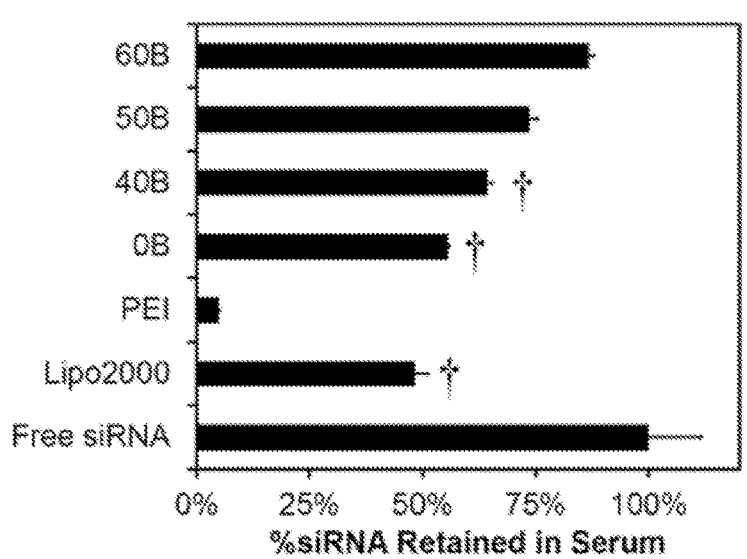
FIG. 17 includes plots and images showing A) a plot percent siRNA retained in serum for different PEGylated nanoparticles incubated in blood at 37° C., B) a plot of percent FRET in serum for FRET-nanoparticles incubated in diluted human whole blood, C) shows a plot of the stability of FRET-nanoparticles incubated in 2 U/mL of heparin for nanoparticles comprised of different polymers, D) shows a plot of percent of injected dose in serum for 50B and 0B nanoparticles showing that circulation half-life was 18.4 min for 50B and 5.8 min for 0B (p<0.05, n=3), E) shows a plot of fluorescence for 50B and 0B injected mice, F) shows a plot of the results of intravital imaging of intravenously injected 50B and 0B nanoparticles that demonstrates relatively more rapid kidney distribution and systemic clearance of 0B than 50B, G) shows time course images of the overall systemic biodistribution of fluorescent siRNA delivered via 50B and 0B nanoparticles, H) shows a plot of siRNA fluorescence in kidneys excised at 5 minutes post injection for 0B (white) and 50B (gray) nanoparticles, I) shows plots of postmortem tissue biodistribution for 50B and 0B loaded nanoparticles at 20 min, 1 hr, and 2 hrs post-injection (p<0.05, n=3). J) shows a plot of cumulative fluorescence in all of the organs at 2 hr post injection (p<0.05), and K) shows representative tissue biodistribution images taken 2 h post-injection.
Figure 17B:
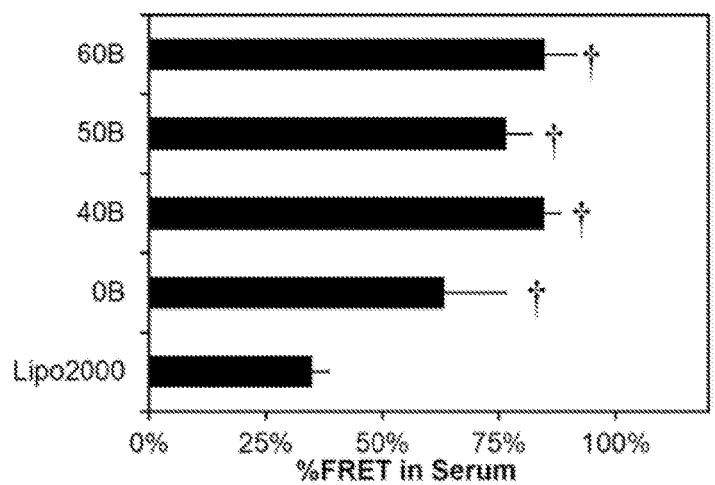

The ex vivo experiments in human whole blood showed that, after a 1 hour incubation in whole blood, loaded nanoparticles made with 50B were 74% retained in the serum fraction, whereas commercial standards PEI (5%) and Lipofectamine 2000 (48%) were more significantly associated with the cellular fraction following centrifugation (FIG. 17A). After incubating FRET-nanoparticles for 1 hour in whole blood, measurement of the FRET signal in the serum fraction showed that the 50B loaded nanoparticles retained a high % FRET signal of 77% while Lipofectamine 2000 showed a significant (p<0.05) decrease in relative % FRET to 35% of the baseline signal (FIG. 17B).

Figure 17C:
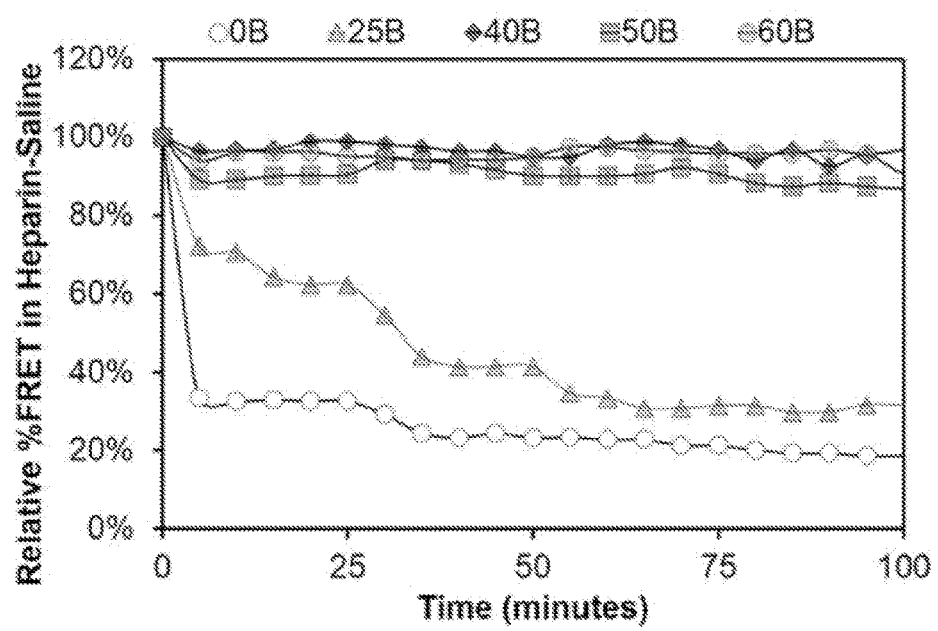
Figure 18:
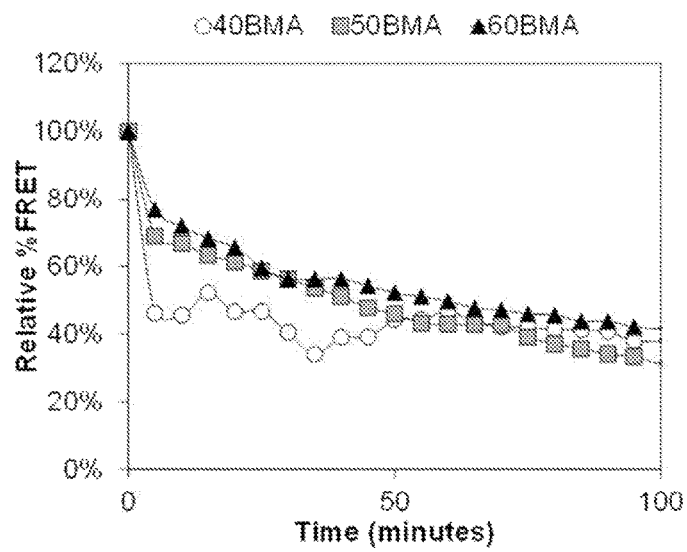
FIG. 18 includes a plot of relative percent FRET over time for nanoparticles comprising 40B, 50B, and 60B polymers showing that the nanoparticles can destabilize in the presence of 10 U heparin/mL over a 100 min time course as demonstrated by the decrease in FRET.

Lastly, because siRNA decomplexation by heparan sulfate-containing glomerular basement membrane (GBM) in the kidney can be a primary cause for rapid systemic clearance of polycation-siRNA nanoparticles, the stability of FRET-nanoparticles was measured in the presence of 2 U/mL of heparin sodium salt in DPBS. The fluorescence emission was measured over time using a microplate reader with an excitation wavelength of 488 nm and an emission wavelength of 670 nm (Tecan Infinite F500, Mannedorf, Switzerland). It was observed that destabilization was dependent on the composition of the core-forming polymer block (FIG. 17C). Higher concentrations of heparin (>10 U/mL) were capable of dissociating the higher % BMA nanoparticles 40B-60B (FIG. 18). These data suggest that incorporation of hydrophobic content will slow the rate of kidney filtration of siRNA-loaded nanoparticles.

Example 7

This Example characterizes the stability and biodistribution of the nanoparticles of the previous Examples in vivo.

Balb/c mice (6-8 weeks of age) were injected intravenously into the tail vein with nanoparticles containing a dsDNA (model for siRNA) labeled with 5' IRDye® 800CW (Integrated DNA Technologies, IDT, Coralville, Iowa). Blood samples were collected at 2, 5, 10, 15, and 20 minutes (maximum 2 blood collections per mouse). Separate cohorts of mice were euthanized for additional blood sample collection and organ harvesting for biodistribution analysis at 5 min, 20 min, 1 hour, and 2 hours post-injection. Blood was centrifuged at 500×g for 5 minutes and the supernatant was measured for fluorescence using a plate reader (Tecan Group Ltd., Switzerland) with 790 nm excitation and 810 nm emission.

Figure 17D:
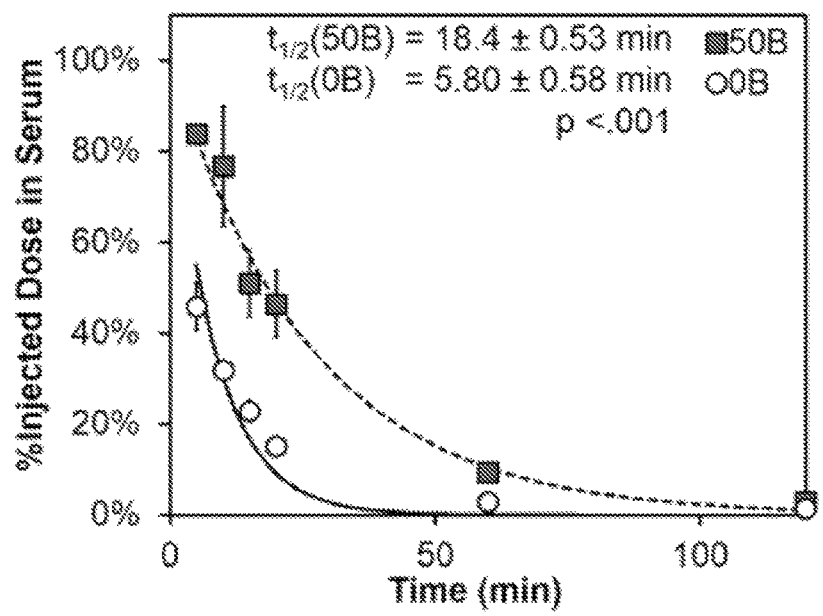

Increased resistance to heparin-mediated destabilization of 50B-based loaded nanoparticles was found to be functionally significant in vivo and yielded a 3.2-fold increase in the blood circulation half-life (18.4±0.53 vs. 5.80±0.58 minutes) and 3.4-fold increase in area under the curve (AUC) (14.0 mg*h/L vs. 4.1 mg*h/L) relative to the benchmark polymer 0B ($p<0.05$ for both half-life and AUC, FIG. 17D). The blood circulation half-life of 0B showed rapid decomplexation and systemic removal in the kidney.

In addition, mice were monitored intravitally using an IVIS 200 for the first 20 minutes post-injection and at postmortem endpoints of 5 min, 20 min, 1 hr, and 2 hr post-injection in order to measure the kinetics of biodistribution to the liver and kidneys. The backs of mice were shaved the day before injection and imaged with the dorsal side facing the camera to visualize and measure kidney and liver biodistribution. Regions of interest (ROIs) were drawn around the liver, kidneys, and the entire mouse to measure organ-specific and total fluorescence, respectively. An IVIS 200 was used to quantify the biodistribution in the explanted lungs, heart, liver, kidney, and spleen using Living Image™ 4.3 quantification software.

Figure 17E:
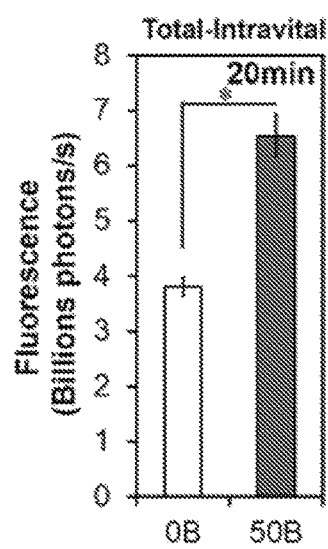
Figure 17F:
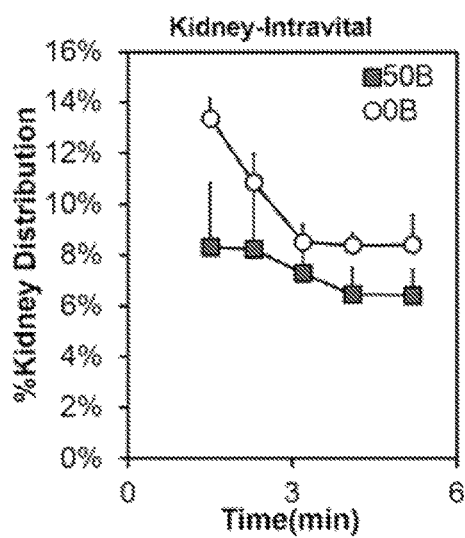
Figure 17G:
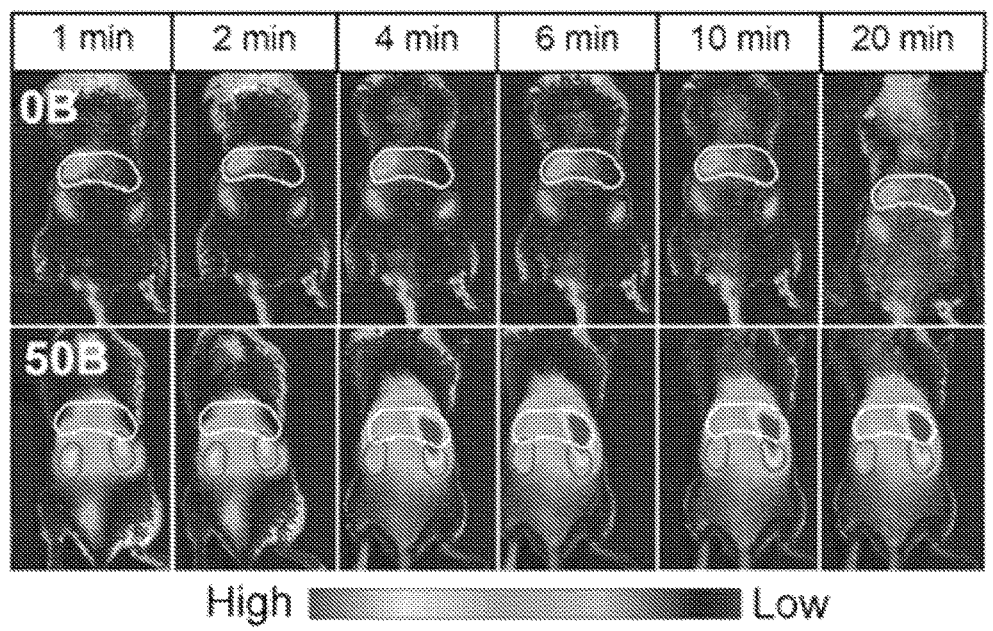

In agreement with the 50B loaded nanoparticles having less rapid renal decomplexation and siRNA removal through the urine acutely following injection than 0B loaded nanoparticles, there was an immediate spike in concentration of siRNA in the kidneys of 0B loaded nanoparticle-treated mice, and overall systemic clearance of siRNA was faster than following delivery with 50B nanoparticles (FIGS. 17E and 17F). This trend was shown visually in representative mice (FIG. 17G), and the full panel of intravital images is shown in FIG. 19.

Figure 17H:
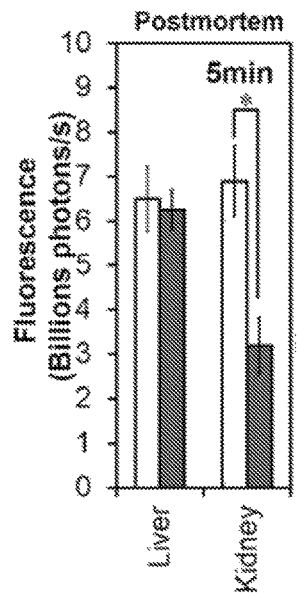
Figure 17I:
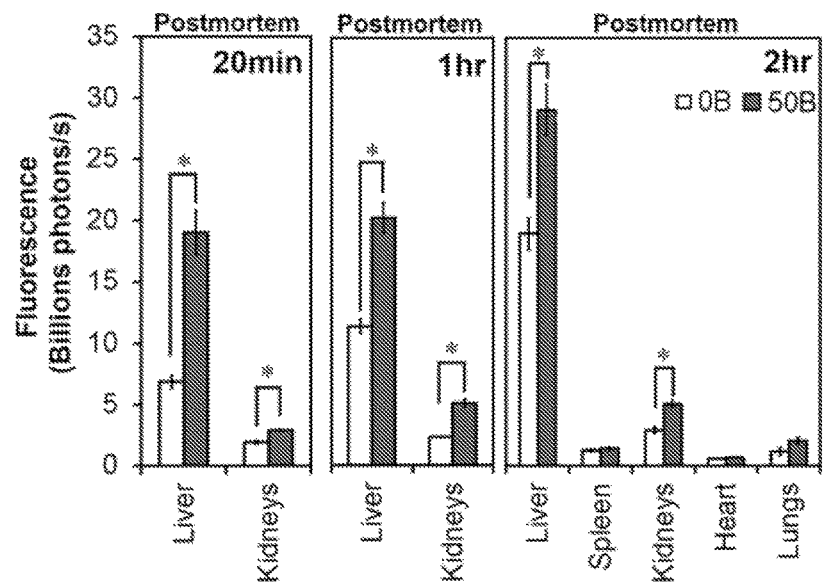
Figure 17J:
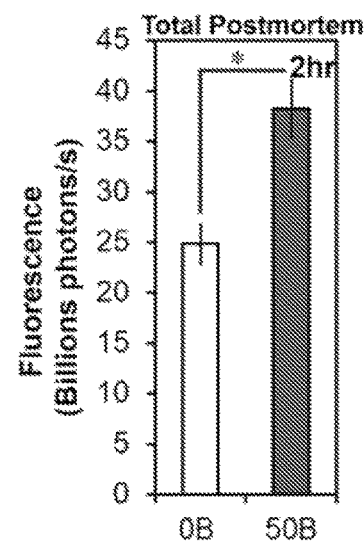
Figure 17K:
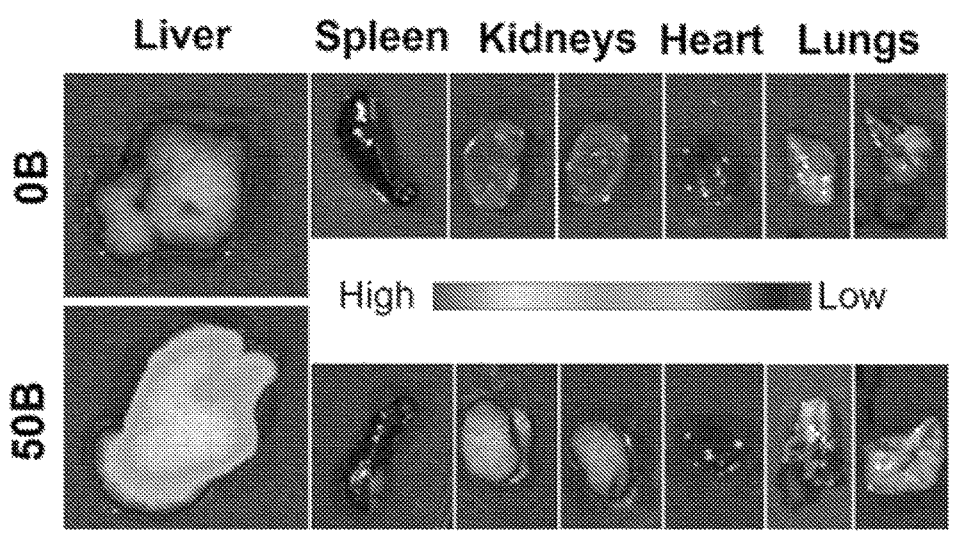
Figure 19:
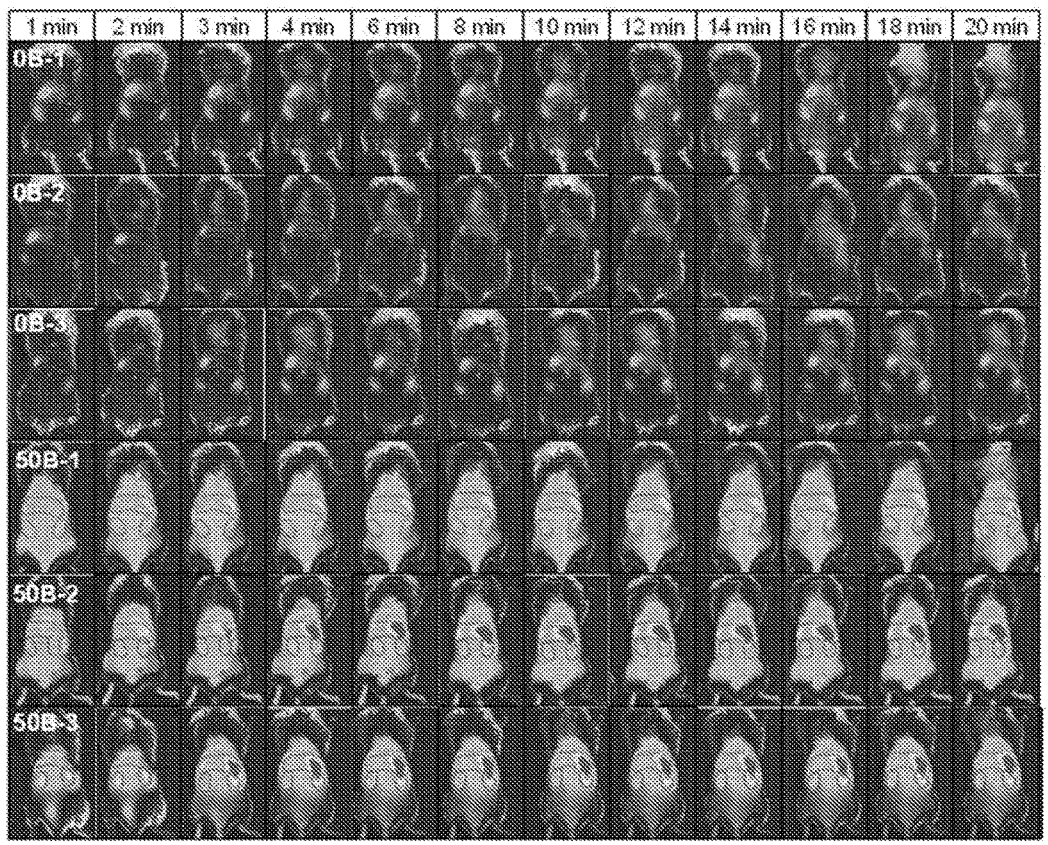
FIG. 19 includes intravital images taken after intravenous administration of loaded nanoparticles showing renal clearance and liver uptake of the nanoparticles in mice.
Figure 20:
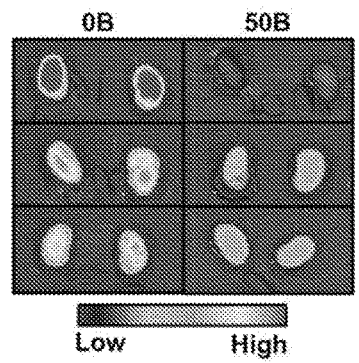
FIG. 20 includes images showing an acute (5 minute post-injection) renal biodistribution of siRNA delivered via 0B nanoparticles relative to 50B nanoparticles.

Imaging of kidneys excised from mice that were euthanized 5 minutes post-injection confirmed the intravital imaging data and showed a 2.2-fold increase in siRNA distribution in the kidney for 0B relative to 50B (FIGS. 17H and 19). Liver biodistribution was noted at 5 min, 20 min, 1 hr and 2 hr endpoints for 0B and 50B nanoparticles and suggested that uptake in the liver is the primary route for removal of intact nanoparticles (FIGS. 17I to 17K). There was greater quantity of siRNA in the liver and kidneys for 50B than 0B ($p<0.05$) at 20 min, 1 hr, and 2 hrs. The kidneys also have higher fluorescence at the later time points based on continued clearance of the relatively longer-circulating 50B formulations. The integrated fluorescence across all organs was 1.5 fold higher in 50B nanoparticles than 0B after 2 h ($p<0.05$, FIG. 17J), which was also consistent with slower removal through the urine and better overall biodistribution of 50B relative to 0B nanoparticles. Relatively less uptake was observed in the lungs and heart that would be associated with acute pulmonary toxicity.

Example 8

This Example characterizes the gene silencing properties of the nanoparticles of the previous Examples in vivo.

Balb/c mice (6-8 weeks of age) were injected intravenously into the tail vein with nanoparticles containing a dicer-substrate siRNA designed against cyclophilin B (PPIB, IDT) at a dose of 2 mg/kg. 25-mer sense strands and 27-mer antisense strand were used, the PPIBs respectively having the sequences 5'-GCAUGGAUGUGGUACG-GAAGGUGGA-3' and 5'-UCCACCUUCCGUACCA-CAUCCAUGCCC-3'. Mice were sacrificed at 48 h, and the RNA was extracted from organs with TRIZOL (Invitrogen, Carlsbad, Calif.) and purified with RNEasy spin column (Qiagen, Venlo, Netherlands). The expression of PPIB was evaluated by RT-PCR using the AACt method normalizing to GAPDH.

Figure 21:
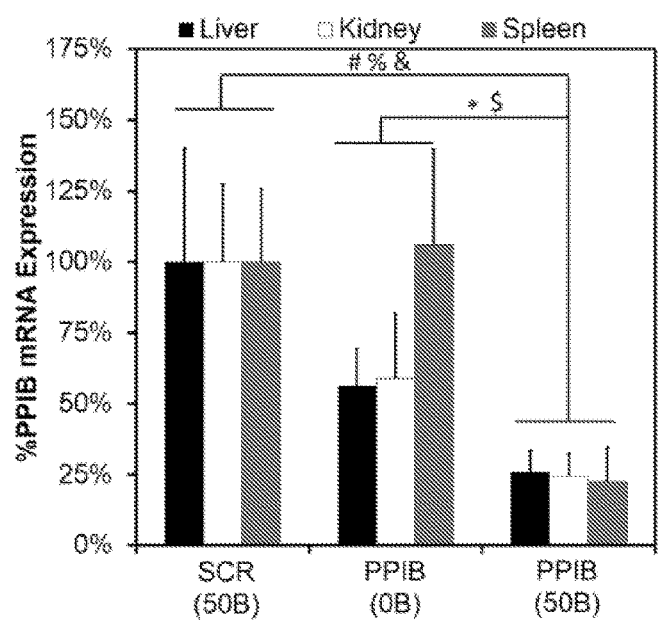
FIG. 21 includes a plot of gene silencing of the model gene PPIB by PCR 48 h after intravenous injection of 2 mg/kg siRNA doses. Markers of statistical differences: #,*—Liver; %—Kidney; &,$—Spleen.
Figure 22:
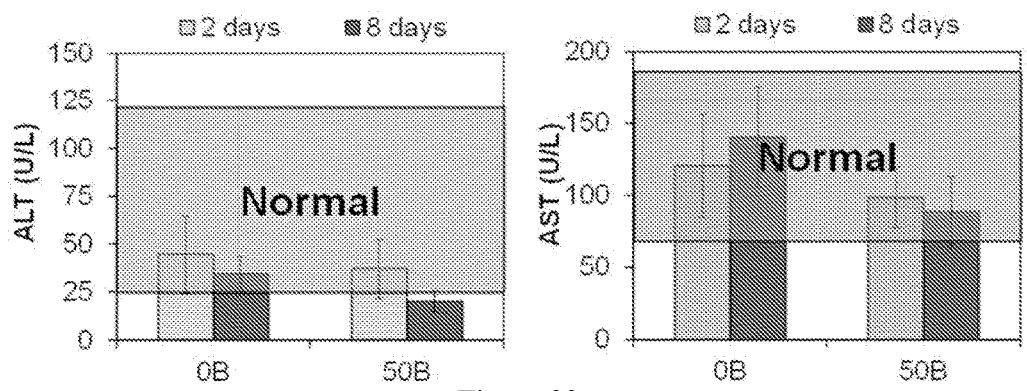
FIG. 22 includes plots of (left) alanine aminotransferase (ALT) and (right) aspartate aminotransferase (AST) measurements on the mouse serum at both 2 days and 8 days post treatment with intravenously injected 0B and 50B loaded nanoparticles.

The liver, kidneys, and spleen were selected as target tissues based on their known reticuloendothelial system (RES) function and the results of the biodistribution analysis. As shown in FIG. 21, 50B loaded nanoparticles robustly silenced PPIB in the liver by about 74% following an intravenous dose of 2 mg/kg siRNA. Furthermore, 50B generated significantly greater gene silencing than 0B nanoparticles injected at the same dose of 2 mg/kg ($p<0.05$). Similarly, 50B nanoparticles significantly silenced PPIB in the kidneys and spleen relative to scrambled controls ($p<0.05$), and 50B silencing was significantly greater in the spleen relative to 0B ($p<0.05$, for 0B versus 50B in the kidney). The similar level of gene silencing measured in the different organs also implies widespread tissue distribution of intact, bioactive 50B nanoparticles and that these nanoparticles may be used to preferentially accumulate in a variety of target tissues if implemented with the appropriate targeting ligand. All nanoparticle injections were well-tolerated by the mice, and no elevation in serum markers of liver toxicity ALT or AST were detected in mice treated with 50B or 0B at days 2 or 8 post-injection (FIG. 22).

Example 9

This Examples describes the synthesis and characterization of nanoparticles comprising pDNA. This Example further compares the embodied nanoparticles to PEI nanoparticles.

Materials

Luciferase reporter plasmid (pPK-CMV-R3) and Promo-Fluor-500 fluorescent labeling kit were purchased from Promokine (Heidelberg, Germany). Live/dead viability/cytotoxicity kit, lipofectamine2000 transfection reagent, Opti-MEM reduced serum media, Dulbecco's phosphate buffered saline (DPBS), Dulbecco's Modified Eagle Medium (DMEM), fetal bovine serum (FBS), penicillin streptomycin, and 0.4% trypan blue stain were purchased from Invitrogen (Grand Island, N.Y.). MDA-MB-231 breast cancer cell line was obtained from ATCC (Manassas, Va.). All other reagents were purchased from Sigma Aldrich (St. Louis, Mo.).

Poly(EG-b-(DMAEMA-co-BMA)) Synthesis and Characterization

RAFT polymerization was used to synthesize a library of diblock copolymers. 4-Cyano-4-(ethylsulfanylthiocarbonyl)sulfanylvpentanoic acid (ECT) was synthesized following standard procedures and was subsequently conjugated to 5 kDa mono-methoxy-PEG using DCC and DMAP, resulting in 91% substitution of the PEG. The polymerization reaction was carried out at 70° C. for 24 h using azobisisobutyronitrile as the initiator with a 5:1 [CTA]:[Initiator] molar ratio. A series of polymerizations were carried out with monomer feed ratios of 40 or 50 mol % BMA and 60 or 50 mol % DMAEMA. For 40 and 50% BMA polymers with short block length, the degree of polymerization was 150, and the polymerization time was 6 h. For 40% BMA with long block length and 50% BMA with medium block length, the degree of polymerization was 150, and the polymerization time was 24 h. For 50% BMA with long block length, the degree of polymerization was 200, and the polymerization time was 24 h. In all cases, the monomer was added at 40% wt/vol in dioxane. The reaction was stopped by exposing the polymerization solution to air, and the resulting diblock polymers were precipitated into an excess of pentane. The isolated polymers were vacuum dried, re-dissolved in water, further purified using PD10 columns, and lyophilized. Polymers were characterized for composition and molecular weight by 1H nuclear magnetic resonance spectroscopy (NMR, Bruker 400 Mhz Spectrometer equipped with 9.4 Tesla Oxford magnet). Absolute molecular weight of the polymers was determined using DMF mobile phase gel permeation chromatography (GPC, Agilent Technologies, Santa Clara, Calif.) with inline Agilent refractive index and Wyatt miniDAWN TREOS light scattering detectors (Wyatt Technology Corp., Santa Barabara, Calif.).

Polymer-pDNA Nanoparticle Formation

Prior to mixing, both pDNA and poly(EG-b-(DMAEMA-co-BMA)) polymers were diluted in 100 mM citric acid/sodium citrate buffer solution (pH 4). Nanoparticles were formed by mixing equal volumes of pDNA and polymer solutions by pipetting. After incubating the nanoparticles 15 min at room temperature, sodium carbonate/bicarbonate buffer (pH 10.8) was added to bring the pH to 7.4. The concentration of pDNA in the final solution was 25 µg/ml, and the concentration of the polymer solution was dependent on the desired amine/phosphate (N/P) ratio (1, 2, 5, 10, 20, or 30). The N/P ratio was defined as the ratio of the total amines in the polymer to the total phosphates in pDNA.

To make control nanoparticles, PEI (25,000 Da, branched) and pDNA were separately diluted in equal volumes of DPBS. Nanoparticles were formed by mixing the PEI and pDNA solutions by pipetting. The mixture was incubated 15 min before adding to cells. The concentration of pDNA in the final solution was 25 µg/ml, and the concentration of the polymer solution was dependent on the desired amine/phosphate (N/P) ratio (1, 2, 5, 10, 20, or 30).

Polymer-pDNA Nanoparticle Lyophilization

Polymer-pDNA nanoparticles were formed as described above. To stabilize nanoparticles during freezing and lyophilization, trehalose was added as an excipient in a ratio of 200:1 trehalose: polymer by mass. Nanoparticles were lyophilized overnight with a vacuum of 0.045 mbar and a collector temperature of −45° C. For transfection and uptake experiments, nanoparticles were reconstituted in water and incubated for 15 min before adding to cells.

Agarose Gel Electrophoresis

To determine the ability of the polymers to efficiently package pDNA, agarose gel electrophoresis was performed. Polymer-pDNA nanoparticles were formed as described above. Samples containing 300 ng pDNA were loaded onto a 0.8% agarose gel and subjected to electrophoresis at 100 V for 45 min. Ethidium bromide was then added to the gel to visualize pDNA.

Dynamic Light Scattering (DLS)

Nanoparticles were formed as described above and diluted to a concentration of 1.5 µg/ml pDNA in DPBS or KCl solutions. Nanoparticle size was measured using a Zetasizer Nano ZS at the Vanderbilt Institute of Nanoscale Science and Engineering (Malvern Instruments, Worcestershire, UK). DLS was performed with a wavelength of 633 nm using a 4.0 mW Helium-Neon laser at a backscattering angle of 173°. Nanoparticle size was determined from the average of at least 10 runs of 10 seconds each. For the aggregation study, nanoparticles were incubated at room temperature, and size was measured using DLS at various time points up to 72 h. For $\zeta$-potential measurements, nanoparticles were diluted in 1 mM KCl at pH 7, and $\zeta$-potential was determined from the average of at least 10 runs using a universal dip cell.

Transmission Electron Microscopy (TEM)

Nanoparticles were formed were formed as described above and diluted to a concentration of 10 µg/ml pDNA in DPBS. Formvar film-backed copper grids with 400 mesh size (Electron Microscopy Sciences, Hatfield, Pa.) were inverted onto droplets containing nanoparticles and blotted dry. Next, all samples were counterstained by inverting onto droplets of 3% uranyl acetate. After blotting dry, samples were further desiccated in vacuo overnight prior to imaging on a Philips CM20 system operating at 200 kV. Images were collected using a CCD camera with AMT Image Capture Engine software (v 600.335 h; Advanced Microscopy Techniques, Danvers, Mass.).

In Vitro Transfection

MDA-MB-231 human breast cancer cells were plated in complete DMEM (10% FBS, 100 U/ml penicillin, and 100 µg/ml streptomycin) at a density of 20,000 cells/well in 96-well plates 24 hours prior to transfection. Immediately before transfection, media were aspirated and replaced with 100 µl Opti-MEM+2% FBS. Nanoparticle solution containing 150 ng pDNA was added to each well. 24 h after transfection, transfection media was aspirated and replaced with 100 µl of 1 mg/ml luciferin in complete DMEM. 15 min after luciferin was added, luminescence was measured using a Xenogen IVIS 200 bioluminescence imaging system (Perkin Elmer, Waltham, Mass.) at the Vanderbilt University Institute of Imaging Science (Nashville, Tenn.). Relative luminescence in each well was quantified using Living Image™ software.

Cell Viability

The cytotoxicity of nanoparticles was determined using calcein AM staining to detect live cells. In vitro transfection experiments were carried out as described above. 24 h after transfection, media was aspirated and replaced with 200 μl of a solution of 1 μg/ml calcein AM in DPBS. After incubating 30 min at 37° C., fluorescence intensity was measured using an FL600 microplate reader with an excitation wavelength of 485 nm and an emission wavelength of 530 nm (Bio-Tek Instruments, Winooski, Vt.).

pH-Dependent Red Blood Cell Hemolysis Assay

To screen for endosomolytic activity, a red blood cell hemolysis assay was used to measure the pH-dependent membrane disruptive activity of nanoparticles. Nanoparticles with N/P ratio of 10 were prepared as described above. Human red blood cells were incubated with nanoparticles for one hour in buffers with pH 7.4, 6.8, 6.2, or 5.6 to mimic different stages in the endo-lysosomal pathway. After centrifugation to remove intact cells, the absorbance of the supernatant was measured at 405 nm to determine the amount of hemoglobin released. The absorbance of supernatant from untreated cells was subtracted, and the percent red blood cell disruption was normalized to positive control samples lysed with Triton X-100.

Confocal Microscopy

Colocalization of plasmid and endosomes was analyzed using confocal microscopy. Plasmid DNA was fluorescently labeled using a PromoFluor-500 labeling kit according to the manufacturer's instructions (PromoKine). MDA-MB-231 cells were plated in complete DMEM at a density of 50,000 cells/well in 24-well plates 24 hours prior to transfection. Nanoparticles were formed as described above using fluorescently labeled plasmid, and 375 ng pDNA was added per well into a volume of 500 μl Opti-MEM+2% FBS. 24 h after transfection, media was aspirated and replaced with complete DMEM+75 nM LysoTracker Red probe+1 μg/ml Hoechst stain. After 30 min incubation, cells were imaged with a fluorescent confocal microscope (Zeiss LSM 710 Meta Oberkochen, Germany) to determine distribution of plasmid and endosomes within the cells.

Statistical Analysis

One way analysis of variance (ANOVA) was used to evaluate the statistical significance of results. p values less than 0.05 were considered statistically significant.

Poly(EG-b-(DMAEMA-co-BMA)) Characterization

A library of diblock copolymers with varying compositions and molecular weights were synthesized. Results of polymer characterization using GPC and NMR are shown in Table 2. The abbreviated names of the polymers indicate the mol % BMA in the DMAEMA-co-BMA block (40 or 50%) and the relative length of the DMAEMA-co-BMA block (short [S], medium [M], or long [L]). PEG block mass was held constant at 5000 Da.

TABLE 2

Block lengths and composition of poly(EG-b-(DMAEMA-co-BMA)) polymers

| Polymer Name | PEG (Da) | DMAEMA-co-BMA (Da) | % BMA in DMAEMA-co-BMA block | PDI |
|---|---|---|---|---|
| 40S | 5000 | 12,428 | 39.3% | 1.079 |
| 40L | 5000 | 20,765 | 39.6% | 1.117 |
| 50S | 5000 | 13,683 | 48.5% | 1.045 |
| 50M | 5000 | 18,041 | 48.3% | 1.040 |
| 50L | 5000 | 22,857 | 49.7% | 1.161 |

Agarose Gel Electrophoresis

Figure 23:
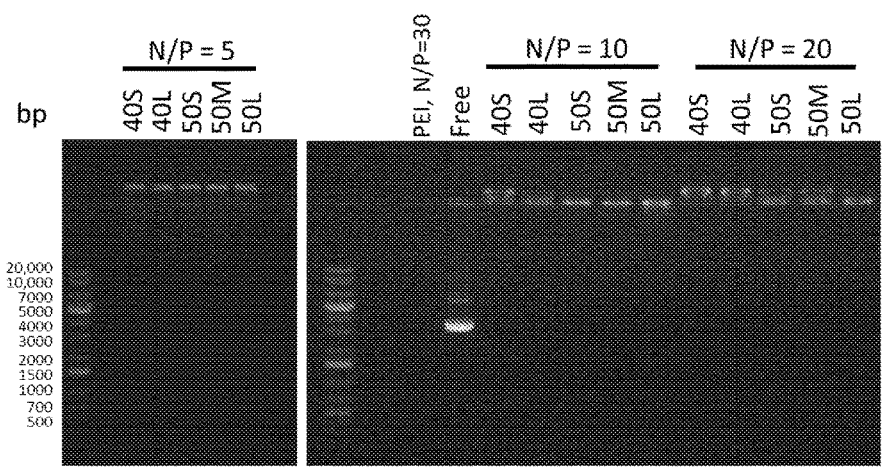
FIG. 23 includes images showing poly(EG-b-(DMAEMA-co-BMA)) nanoparticles with N/P ratios of 5, 10, or 20 were loaded onto a 0.8% agarose gel, where PEI nanoparticles with N/P ratio of 30 and free plasmid DNA were included as controls. The DNA ladder is shown on the left side of each gel.

Agarose gel electrophoresis was performed to assess the ability of the transfection reagents to form nanoparticles with pDNA, as shown in FIG. 23. Poly(EG-b-(DMAEMA-co-BMA))-pDNA nanoparticles with N/P ratios of 5, 10, and 20 did not migrate out of the loading wells, and no free pDNA (FIG. 23) was detected at any of the N/P ratios investigated. These results indicate that poly(EG-b-(DMAEMA-co-BMA)) polymers efficiently encapsulate pDNA at N/P ratios of 5 or above.

Nanoparticle Size and ζ-Potential

Figure 24:
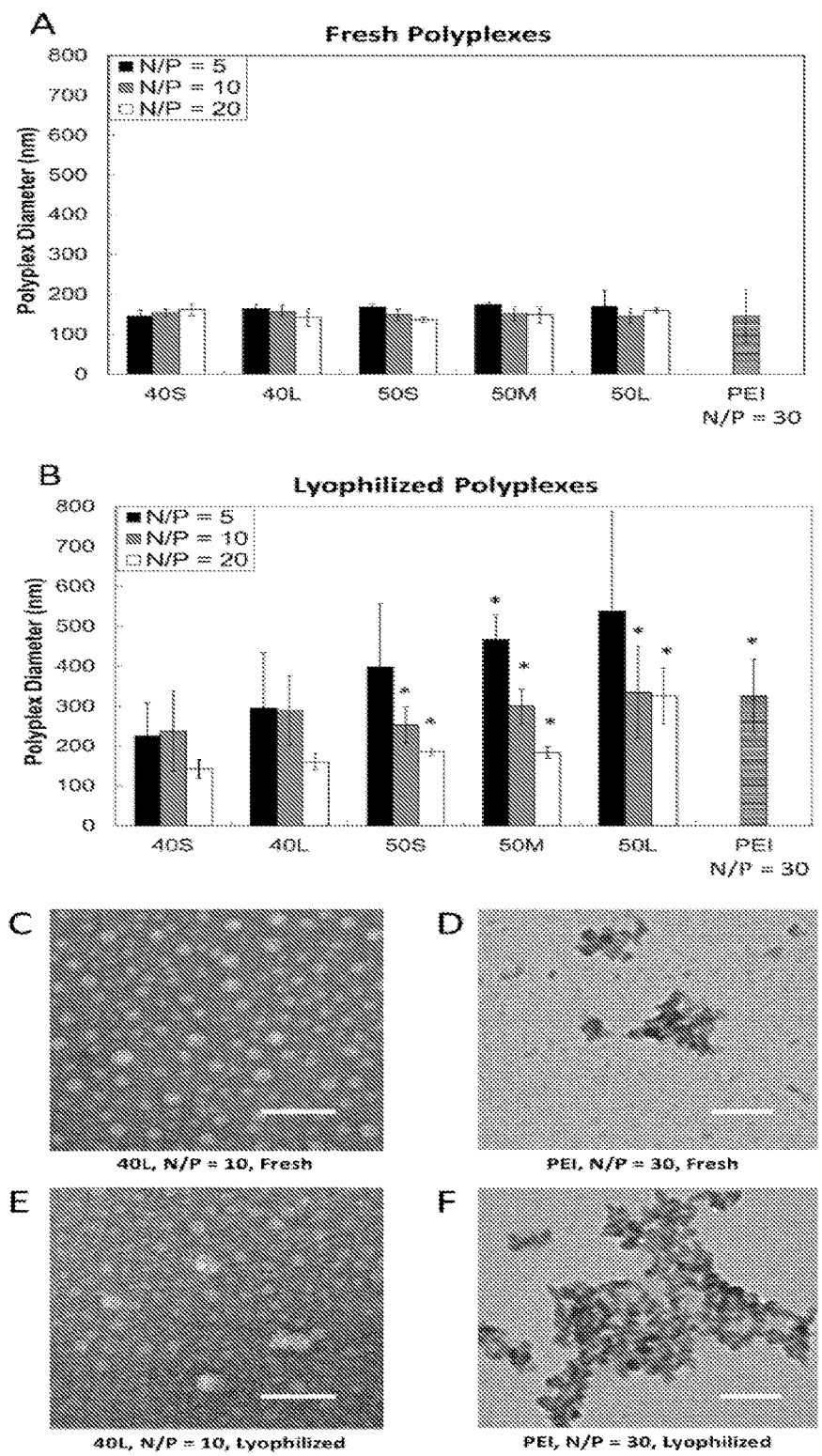
FIG. 24 includes nanoparticles diluted to a concentration of 1.5 µg/ml pDNA in DPBS, where (A) shows a plot of hydrodynamic diameter of nanoparticles before lyophilization, (B) shows a plot of hydrodynamic diameter of nanoparticles after lyophilization and subsequent reconstitution, (C-E) show TEM images of 40L-pDNA nanoparticles before (C) and after (E) lyophilization, and (D-F) show TEM images of PEI-pDNA nanoparticles before (D) and after (F) lyophilization. Scale bar=100 nm.

Initial nanoparticles size was measured in DPBS (FIG. 24A). Before lyophilization, the sizes of all nanoparticulate nanoparticles were below 200 nm, and the diameter of poly(EG-b-(DMAEMA-co-BMA)) nanoparticles ranged from 130-180 nm. N/P ratio, BMA content, or block length did not significantly affect initial nanoparticle size. The mean diameters of poly(EG-b-(DMAEMA-co-BMA)) nanoparticles were similar to the mean size of PEI nanoparticles (150 nm).

After lyophilization, the sizes of PEI nanoparticles and most of the formulations containing 50% BMA poly(EG-b-(DMAEMA-co-BMA))-pDNA nanoparticles increased significantly ($p<0.05$) as shown in FIG. 24B. In contrast, the sizes of 40S and 40L nanoparticles with N/P ratio of 20 remained below 200 nm and did not significantly increase after lyophilization. In general, increasing the N/P ratio increased the stability of poly(EG-b-(DMAEMA-co-BMA)) nanoparticles, leading to smaller increases in diameter after lyophilization. FIGS. 24C and 24E show TEM images of spherical 40L-pDNA nanoparticles, which exhibited minimal increase in size after lyophilization. FIGS. 24D and F show TEM images of loosely associated PEI-pDNA nanoparticles that increased in size after lyophilization.

Figure 25:
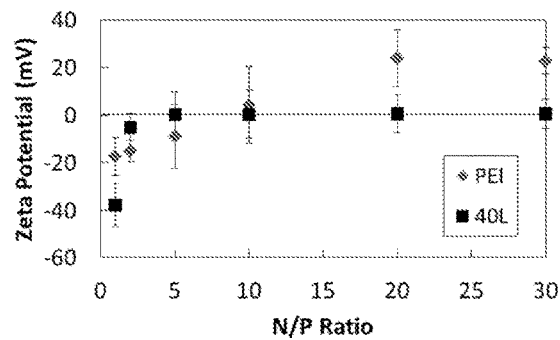
FIG. 25 includes a plot showing ζ-potential measured in 1 mM KCl.

As shown in FIG. 25, the ζ-potential of 40L and PEI nanoparticles increased as N/P ratio increased. At N/P ratios≥5, the ζ-potential of 40L nanoparticles approached 0 mV. At higher N/P of 20 and 30, the ζ-potential of 40L nanoparticles was neutral due to shielding of the excess cationic charge in the nanoparticle core by the PEG corona. In contrast, the ζ-potential of PEI nanoparticles increased up to an N/P ratio of 20, at which point it asymptotically approached +20 mV.

Aggregation Study

The aggregation kinetics of nanoparticles in DPBS were assessed at N/P ratios of 5 (FIG. 26A) and 10 (FIG. 26B) and compared to PEI at N/P ratio of 30. PEI nanoparticles exhibited faster aggregation than poly(EG-b-(DMAEMA-co-BMA)) nanoparticles, forming aggregates >1000 nm after 24 h. Poly(EG-b-(DMAEMA-co-BMA)) nanoparticles with N/P ratio of 5 were less stable than those with N/P ratio of 10. 40L nanoparticles with N/P ratio of 10 exhibited the greatest stability, remaining <200 nm after more than 60 hours in DPBS.

Figure 26:
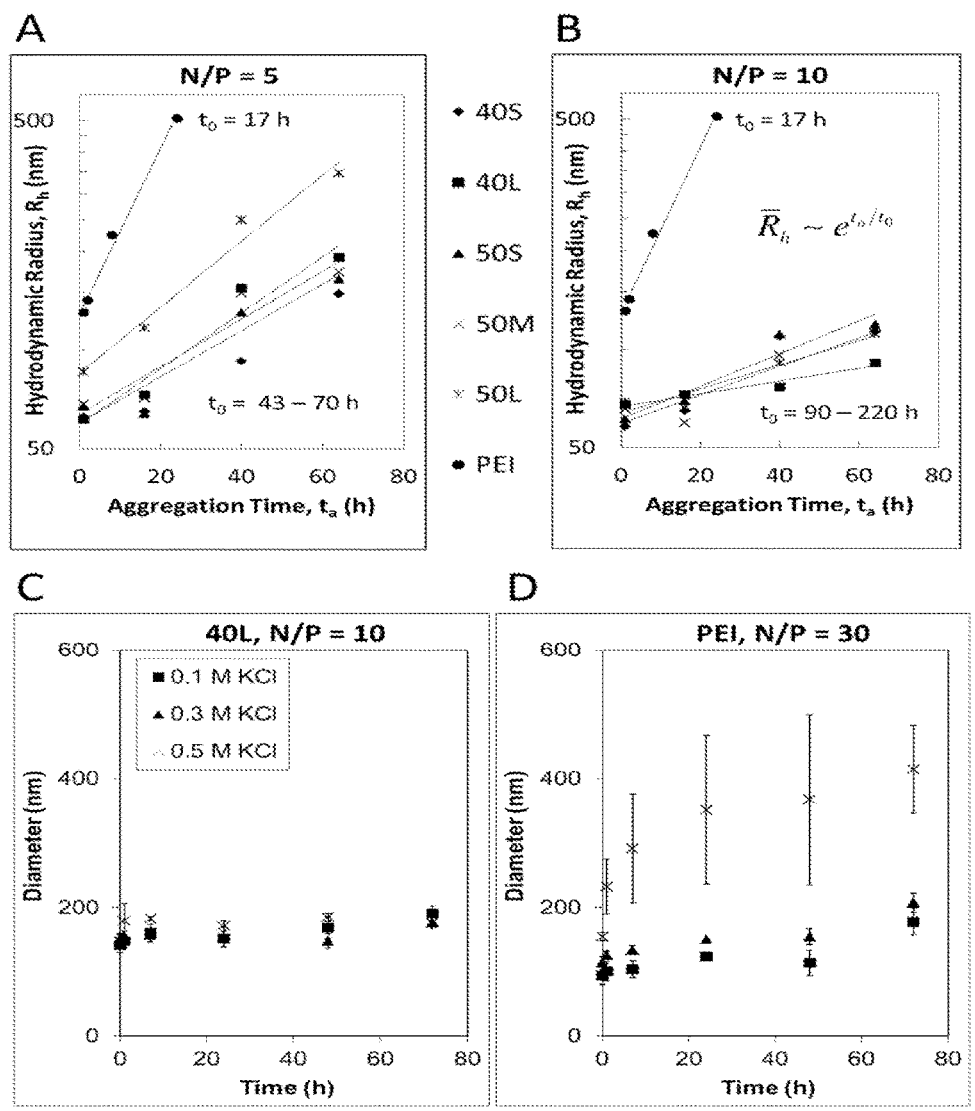
FIG. 26 includes plots showing aggregation of nanoparticles with N/P ratio of 5 (A) and 10 (B) in DPBS over time. Size of PEI nanoparticles with N/P ratio of 30 is included as a comparison, and data were fit to the reaction-limited colloidal aggregation model. $R^2$ values ranged from 0.85-0.995; and includes plots showing the effects of ionic strength of KCl on aggregation of 40L (C) and PEI (D) nanoparticles.

Previous studies have shown that for slow Brownian flocculation, the floc diameter grows exponentially with time. Weitz described a reaction-limited colloidal aggregation model for systems with stability ratio >>1:[23]

$$\bar{R}_h \sim e^{t_a/t_0} \quad (1)$$

where $R_h$ is a scaling parameter approximating the average hydrodynamic radius, $t_a$ is aggregation time, and $t_0$ is an aggregation time constant that varies with initial particle concentration and single particle sticking probability. The reaction-limited aggregation model was applied to quantify the aggregation time constants. The exponential model fit well for all nanoparticles investigated (FIGS. 26A and 26B). The time constants for aggregation determined from these fits provided quantitative evidence for the increased stability of poly(EG-b-(DMAEMA-co-BMA)) nanoparticles compared to PEI. The aggregation time constants for poly(EGb-(DMAEMA-co-BMA)) nanoparticles with N/P ratio of 5 were more than 2.5 times greater than the time constant for PEI. Furthermore, increasing the N/P ratio from 5 to 10 approximately doubled the aggregation time constants for 40L nanoparticles.

Effects of Ionic Strength on Aggregation 40L (FIG. 26C) and PEI (FIG. 26D) nanoparticles stability was also investigated as a function of ionic strength by varying KCl concentration. As [KCl] increased, PEI nanoparticles aggregated more rapidly, a behavior that was consistent with the notion that PEI nanoparticles are stabilized, at least in part, by electrostatic repulsion. In contrast, [KCl] had no effect on aggregation rate of 40L nanoparticles. 40L nanoparticles did not aggregate substantially, remaining <200 nm in diameter after 72 h at all KCl concentrations investigated. These observations suggested that 40L nanoparticles are stabilized by steric and hydrophobic interactions and not by electrostatic repulsion; hence, ionic strength does not affect their aggregation rate.

In Vitro Transfection and Cytotoxicity

Figure 27:
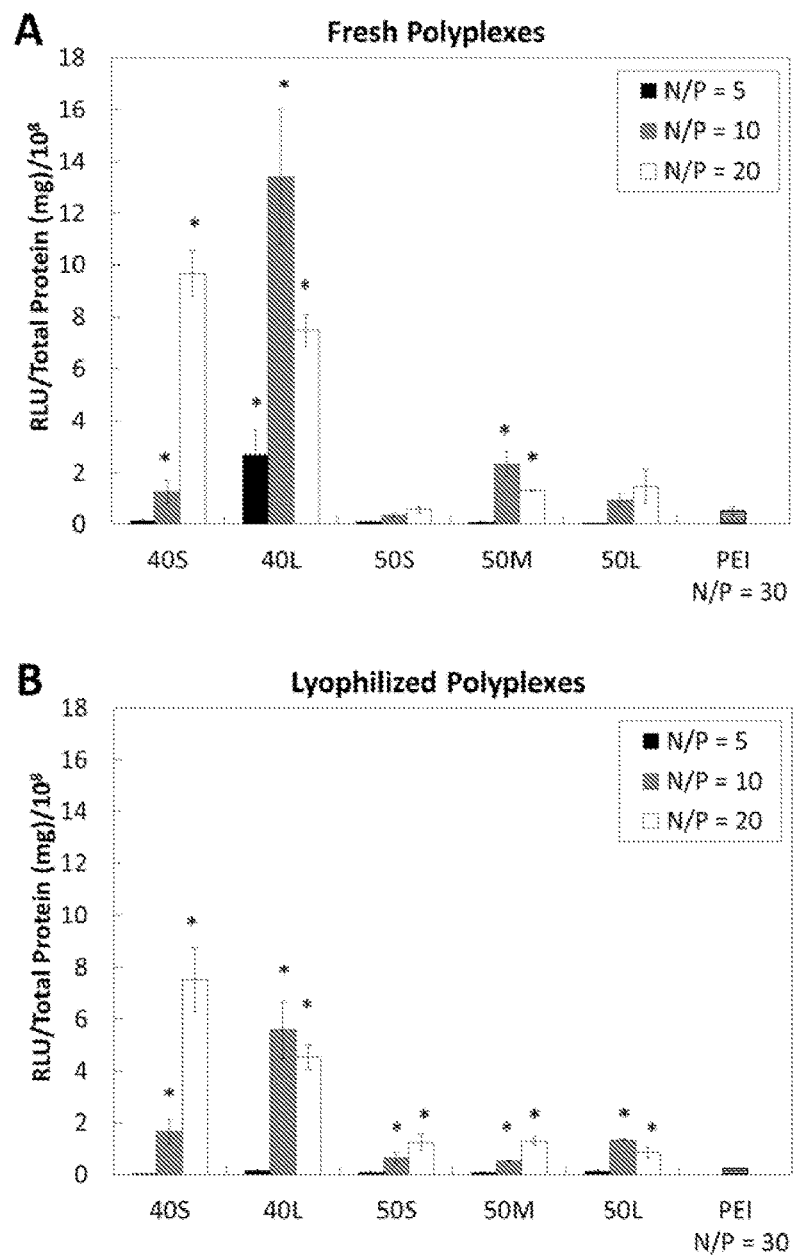
FIG. 27 includes plots showing (A) luminescence produced by cells transfected with fresh nanoparticles normalized to total protein, and (B) luminescence produced by cells transfected with lyophilized nanoparticles normalized to total protein. Asterisks indicate significant increase in transfection compared to PEI (p<0.05). Data are plotted as mean±standard deviation.

The ability of the polymers to transfect MDA-MB-231 cells in vitro was assessed by delivering a luciferase reporter plasmid (FIG. 27). Fresh 40S nanoparticles with N/P ratio of 10 and 20; 40L nanoparticles with N/P ratio of 5, 10, and 20; and 50M nanoparticles with N/P ratio of 10 and 20 had significantly higher transfection than fresh PEI nanoparticles (FIG. 27A). All lyophilized poly(EG-b-(DMAEMA-co-BMA)) nanoparticles with N/P ratio of 10 and 20 had significantly higher transfection efficiency than lyophilized PEI nanoparticles (FIG. 27B).

Figure 28:
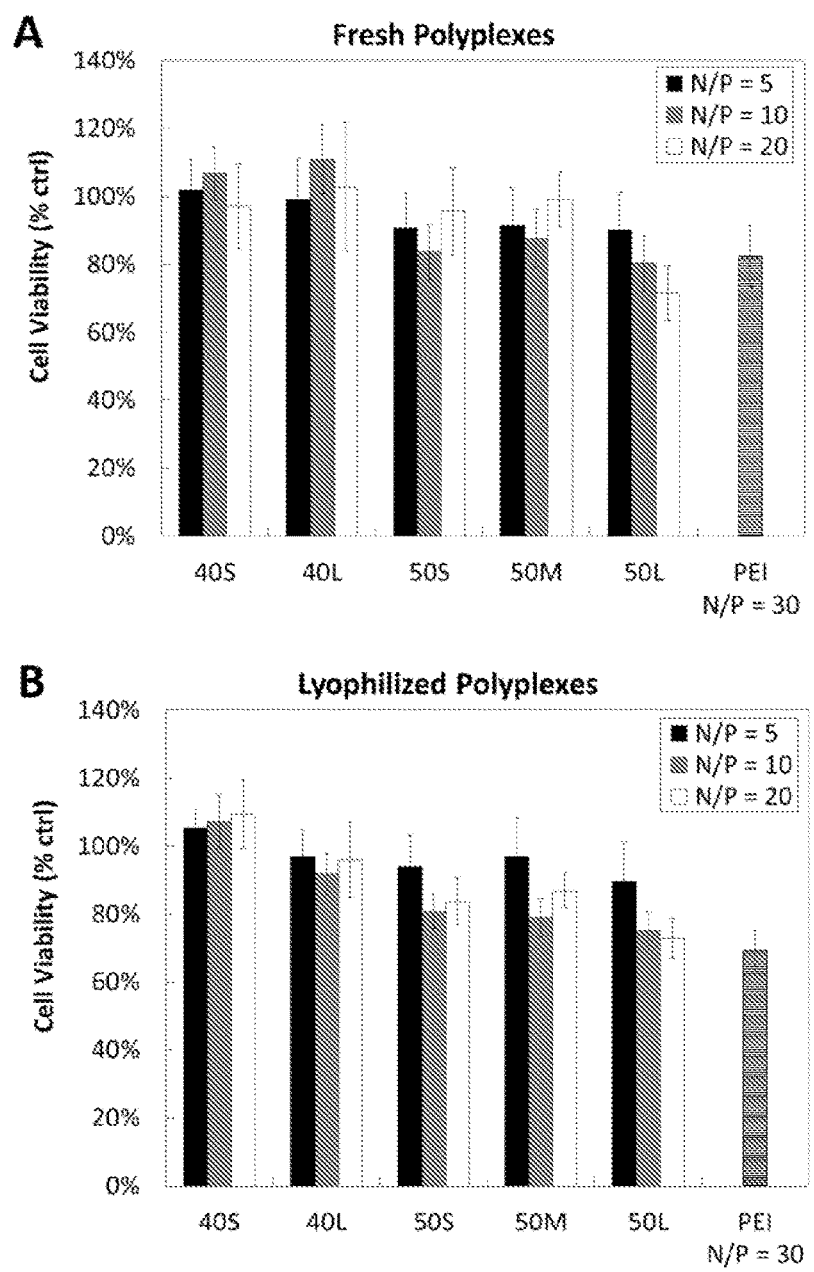
FIG. 28. includes plots showing cell viability after transfection with fresh (A) or lyophilized (B) nanoparticles relative to untreated cells was assessed using calcein AM staining Data are plotted as mean±standard deviation.

To determine cytotoxicity of fresh and lyophilized nanoparticles, calcein AM staining was used to quantify number of live cells after transfection (FIG. 28). All wells treated with poly(EG-b-(DMAEMA-co-BMA)) nanoparticles had >70% viability relative to untreated wells. The viability of cells treated with poly(EG-b-(DMAEMA-co-BMA)) nanoparticles was comparable to or higher than cells treated with PEI nanoparticles.

pH-Dependent Membrane Disruption and Endosomal Escape

Figure 29:
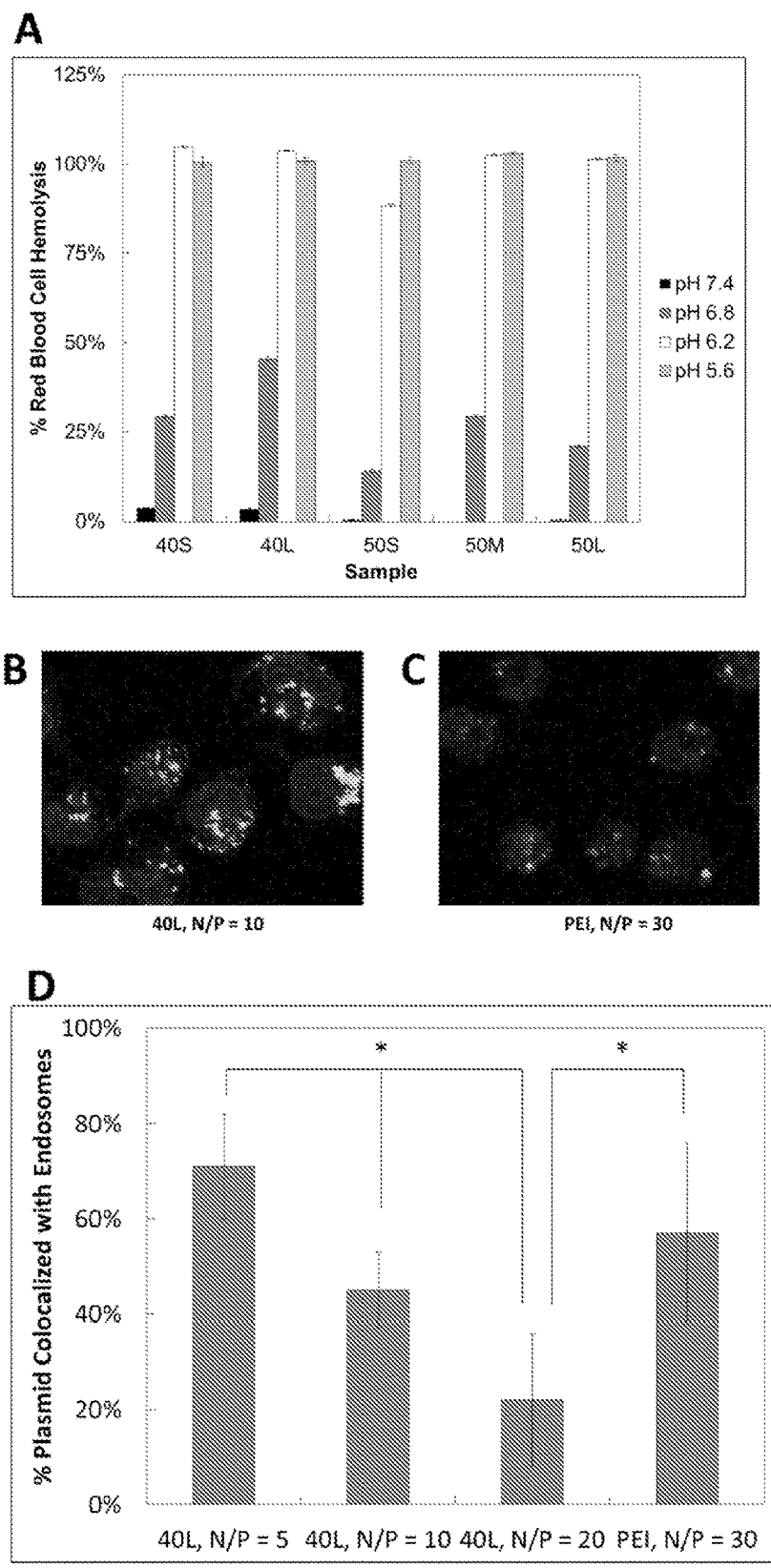
FIG. 29 includes images and plots showing (A) a pH-dependent red blood cell hemolysis assay, confocal microscopy images of MDA-MB-231 cells transfected with 40L-pDNA includes plots showing with N/P ratio of 10 (B) or PEI-pDNA nanoparticles with N/P ratio of 30 (C) showing distribution of plasmid (green), endosomes (red), and nuclei (blue), and (D) percentage of plasmid located within endosomes. Data are plotted as mean±standard error, and asterisks indicate statistically significant difference (p<0.05).

A red blood cell hemolysis assay was performed to determine pH-dependent membrane disruption by the nanoparticles. As shown in FIG. 29A, all nanoparticles had <5% hemolysis at pH 7.4 (mimicking extracellular and cytosolic pH). As pH decreased, hemolytic behavior of the nanoparticles increased significantly. All nanoparticles produced 100% hemolysis (statistically equivalent to Triton X detergent) at pH 5.6 (mimicking late endosomes), suggesting that the nanoparticles can achieve efficient endosomal escape.

Images of cells transfected with 40L or PEI nanoparticles were analyzed to quantify the co-localization of green (plasmid) and red (endosomes) fluorescent probes. As the N/P ratio of 40L increased from 5 to 20, the fraction of green co-localized with red decreased significantly ($p<0.05$). Furthermore, 40L nanoparticles with N/P ratio of 20 had significantly less endosomal co-localization than PEI nanoparticle with N/P ratio of 30. These results provide evidence that the active, pH-dependent membrane disruptive mechanism of 40L is concentration dependent and is superior to the proton sponge mechanism of PEI.

It will be understood that various details of the presently disclosed subject matter can be changed without departing from the scope of the subject matter disclosed herein. Furthermore, the description provided herein is for the purpose of illustration only, and not for the purpose of limitation.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a polymer" includes a plurality of such polymers, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments±20%, in some embodiments±10%, in some embodiments±5%, in some embodiments±1%, in some embodiments±0.5%, and in some embodiments±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Throughout this document, various references are mentioned. All such references are incorporated herein by reference, including the references set forth in the following list:

REFERENCES

1. Fire, A.; Xu, S. Q.; Montgomery, M. K.; Kostas, S. A.; Driver, S. E.; Mello, C. C., Potent and Specific Genetic Interference by Double-Stranded Rna in *Caenorhabditis Elegans*. *Nature* 1998, 391, 806-811.
2. White, P. J., Barriers to Successful Delivery of Short Interfering Rna after Systemic Administration. *Clin Exp Pharmacol Physiol* 2008, 35, 1371-6.
3. Li, H. M.; Nelson, C. E.; Evans, B. C.; Duvall, C. L., Delivery of Intracellular-Acting Biologics in Pro-Apoptotic Therapies. *Curr Pharm Design* 2011, 17, 293-319.
4. Rettig, G. R.; Behlke, M. A., Progress toward in Vivo Use of Simas-Ii. *Mol Ther* 2012, 20, 483-512.
5. Mislick, K. A.; Baldeschwieler, J. D., Evidence for the Role of Proteoglycans in Cation-Mediated Gene Transfer. *Proc Natl Acad Sci USA* 1996, 93, 12349-54.

6. Alexis, F.; Pridgen, E.; Molnar, L. K.; Farokhzad, O. C., Factors Affecting the Clearance and Biodistribution of Polymeric Nanoparticles. *Mol Pharm* 2008, 5, 505-15.
7. Lv, H.; Zhang, S.; Wang, B.; Cui, S.; Yan, J., Toxicity of Cationic Lipids and Cationic Polymers in Gene Delivery. *J Control Release* 2006, 114, 100-9.
8. Dash, P. R.; Read, M. L.; Barrett, L. B.; Wolfert, M. A.; Seymour, L. W., Factors Affecting Blood Clearance and in Vivo Distribution of Polyelectrolyte Complexes for Gene Delivery. *Gene Ther* 1999, 6, 643-50.
9. Verbaan, F. J.; Oussoren, C.; van Dam, I. M.; Takakura, Y.; Hashida, M.; Crommelin, D. J.; Hennink, W. E.; Storm, G., The Fate of Poly(2-Dimethyl Amino Ethyl) Methacrylate-Based Polyplexes after Intravenous Administration. *Int J Pharm* 2001, 214, 99-101.
10. Petersen, H.; Fechner, P. M.; Martin, A. L.; Kunath, K.; Stolnik, S.; Roberts, C. J.; Fischer, D.; Davies, M. C.; Kissel, T., Polyethylenimine-Graft-Poly(Ethylene Glycol) Copolymers: Influence of Copolymer Block Structure on DNA Complexation and Biological Activities as Gene Delivery System. *Bioconjugate Chem* 2002, 13, 845-854.
11. Rungsardthong, U.; Deshpande, M.; Bailey, L.; Vamvakaki, M.; Armes, S. P.; Garnett, M. C.; Stolnik, S., Copolymers of Amine Methacrylate with Poly(Ethylene Glycol) as Vectors for Gene Therapy. *J Control Release* 2001, 73, 359-80.
12. Venkataraman, S.; Ong, W. L.; Ong, Z. Y.; Joachim Loo, S. C.; Ee, P. L.; Yang, Y. Y., The Role of Peg Architecture and Molecular Weight in the Gene Transfection Performance of Pegylated Poly(Dimethylaminoethyl Methacrylate) Based Cationic Polymers. *Biomaterials* 2011, 32, 2369-78.
13. Mishra, S.; Webster, P.; Davis, M. E., Pegylation Significantly Affects Cellular Uptake and Intracellular Trafficking of Non-Viral Gene Delivery Particles. *Eur J Cell Biol* 2004, 83, 97-111.
14. Sato, A.; Choi, S. W.; Hirai, M.; Yamayoshi, A.; Moriyama, R.; Yamano, T.; Takagi, M.; Kano, A.; Shimamoto, A.; Maruyama, A., Polymer Brush-Stabilized Polyplex for a Sirna Carrier with Long Circulatory Half-Life. *Journal of Controlled Release* 2007, 122, 209-216.
15. Verbaan, F. J.; Oussoren, C.; Snel, C. J.; Crommelin, D. J.; Hennink, W. E.; Storm, G., Steric Stabilization of Poly(2-(Dimethylamino)Ethyl Methacrylate)-Based Polyplexes Mediates Prolonged Circulation and Tumor Targeting in Mice. *J Gene Med* 2004, 6, 64-75.
16. Glodde, M.; Sirsi, S. R.; Lutz, G. J., Physiochemical Properties of Low and High Molecular Weight Poly (Ethylene Glycol)-Grafted Poly(Ethylene Imine) Copolymers and Their Complexes with Oligonucleotides. *Biomacromolecules* 2006, 7, 347-356.
17. Itaka, K.; Yamauchi, K.; Harada, A.; Nakamura, K.; Kawaguchi, H.; Kataoka, K., Polyion Complex Micelles from Plasmid DNA and Poly(Ethylene Glycol)-Poly(L-Lysine) Block Copolymer as Serum-Tolerable Polyplex System: Physicochemical Properties of Micelles Relevant to Gene Transfection Efficiency. *Biomaterials* 2003, 24, 4495-506.
18. Luo, D.; Haverstick, K.; Belcheva, N.; Han, E.; Saltzman, W. M., Poly(Ethylene Glycol)-Conjugated Pamam Dendrimer for Biocompatible, High-Efficiency DNA Delivery. *Macromolecules* 2002, 35, 3456-3462.
19. Taratula, O.; Garbuzenko, O. B.; Kirkpatrick, P.; Pandya, I.; Savla, R.; Pozharov, V. P.; He, H. X.; Minko, T., Surface-Engineered Targeted Ppi Dendrimer for Efficient Intracellular and Intratumoral Sirna Delivery. *Journal of Controlled Release* 2009, 140, 284-293.
20. Deshpande, M. C.; Garnett, M. C.; Vamvakaki, M.; Bailey, L.; Armes, S. P.; Stolnik, S., Influence of Polymer Architecture on the Structure of Complexes Formed by Peg-Tertiary Amine Methacrylate Copolymers and Phosphorothioate Oligonucleotide. *J Control Release* 2002, 81, 185-99.
21. Behr, J. P., The Proton Sponge, a Means to Enter Cells Viruses Never Thought Of. *M S-Med Sci* 1996, 12, 56-58.
22. Behr, J. P., The Proton Sponge: A Trick to Enter Cells the Viruses Did Not Exploit. *Chimia* 1997, 51, 34-36.
23. Lee, H.; Jeong, J. H.; Park, T. G., A New Gene Delivery Formulation of Polyethylenimine/DNA Complexes Coated with Peg Conjugated Fusogenic Peptide. *J Control Release* 2001, 76, 183-92.
24. Convertine, A. J.; Benoit, D. S. W.; Duvall, C. L.; Hoffman, A. S.; Stayton, P. S., Development of a Novel Endosomolytic Diblock Copolymer for Sirna Delivery. *Journal of Controlled Release* 2009, 133, 221-229.
25. Duvall, C. L.; Convertine, A. J.; Benoit, D. S.; Hoffman, A. S.; Stayton, P. S., Intracellular Delivery of a Proapoptotic Peptide Via Conjugation to a Raft Synthesized Endosomolytic Polymer. *Mol Pharm* 2010, 7, 468-76.
26. Convertine, A. J.; Diab, C.; Prieve, M.; Paschal, A.; Hoffman, A. S.; Johnson, P. H.; Stayton, P. S., Ph-Responsive Polymeric Micelle Carriers for Sirna Drugs. *Biomacromolecules* 2010.
27. Manganiello, M. J.; Cheng, C.; Convertine, A. J.; Bryers, J. D.; Stayton, P. S., Diblock Copolymers with Tunable Ph Transitions for Gene Delivery. *Biomaterials* 2012, 33, 2301-9.
28. Cheng, C.; Convertine, A. J.; Stayton, P. S.; Bryers, J. D., Multifunctional Triblock Copolymers for Intracellular Messenger Rna Delivery. *Biomaterials* 2012, 33, 6868-6876.
29. Liu, Z.; Zhang, Z.; Zhou, C.; Jiao, Y., Hydrophobic Modifications of Cationic Polymers for Gene Delivery. *Progress in Polymer Science* 2010, 35, 1144-1162.
30. Gary, D. J.; Lee, H.; Sharma, R.; Lee, J. S.; Kim, Y.; Cui, Z. Y.; Jia, D.; Bowman, V. D.; Chipman, P. R.; Wan, L., et al., Influence of Nano-Carrier Architecture on in Vitro Sirna Delivery Performance and in Vivo Biodistribution: Polyplexes Vs Micelleplexes. *ACS Nano* 2011, 5, 3493-505.
31. Xiao, K.; Li, Y.; Luo, J.; Lee, J. S.; Xiao, W.; Gonik, A. M.; Agarwal, R. G.; Lam, K. S., The Effect of Surface Charge on in Vivo Biodistribution of Peg-Oligocholic Acid Based Micellar Nanoparticles. *Biomaterials* 2011, 32, 3435-46.
32. Arvizo, R. R.; Rana, S.; Miranda, O. R.; Bhattacharya, R.; Rotello, V. M.; Mukherjee, P., Mechanism of Anti-Angiogenic Property of Gold Nanoparticles: Role of Nanoparticle Size and Surface Charge. *Nanomedicine: nanotechnology, biology, and medicine* 2011, 7, 580-7.
33. Moad, G.; Chiefari, J.; Chong, Y. K.; Ercole, F.; Krstina, J.; Jeffery, J.; Le, T. P. T.; Mayadunne, R. T. A.; Meijs, G. F.; Moad, C. L., et al., Living Free-Radical Polymerization by Reversible Addition-Fragmentation Chain Transfer: The Raft Process. *Macromolecules* 1998, 31, 5559-5562.
34. Boyer, C.; Bulmus, V.; Davis, T. P.; Ladmiral, V.; Liu, J.; Perrier, S., Bioapplications of Raft Polymerization. *Chem Rev* 2009, 109, 5402-36.
35. Medina-Kauwe, L. K.; Xie, J.; Hamm-Alvarez, S., Intracellular Trafficking of Nonviral Vectors. *Gene Ther* 2005, 12, 1734-51.
36. Evans, B. C.; Nelson, C. E.; Yu, S. S.; Beavers, K. R.; J., K. A.; Li, H.; Nelson, H. M.; Giorgio, T. D.; Duvall, C.

L., Ex Vivo Red Blood Cell Hemolysis Assay for the Evaluation of Ph-Responsive Endosomolytic Agents for Cytosolic Delivery of Biomacromolecular Drugs. *J. Vis. Exp.* 2012, e50166, doi:10.3791/50166.
37. Bartlett, D. W.; Davis, M. E., Physicochemical and Biological Characterization of Targeted, Nucleic Acid-Containing Nanoparticles. *Bioconjug Chem* 2007, 18, 456-68.
38. Gupta, M. K.; Meyer, T. A.; Nelson, C. E.; Duvall, C. L., Poly(Ps-B-Dma) Micelles for Reactive Oxygen Species Triggered Drug Release. *J Control Release* 2012, 162, 591-598.
39. Zuckerman, J. E.; Choi, C. H. J.; Han, H.; Davis, M. E., Polycation-Sirna Nanoparticles Can Disassemble at the Kidney Glomerular Basement Membrane. *P Natl Acad Sci USA* 2012, 109, 3137-3142.
40. Naeye, B.; Deschout, H.; Caveliers, V.; Descamps, B.; Braeckmans, K.; Vanhove, C.; Demeester, J.; Lahoutte, T.; De Smedt, S. C.; Raemdonck, K., In Vivo Disassembly of Iv Administered Sirna Matrix Nanoparticles at the Renal Filtration Barrier. *Biomaterials* 2013, 34, 2350-2358.
41. Chong, Y. K.; Le, T. P. T.; Moad, G.; Rizzardo, E.; Thong, S. H., A More Versatile Route to Block Copolymers and Other Polymers of Complex Architecture by Living Radical Polymerization: The Raft Process. *Macromolecules* 1999, 32, 2071-2074.
42. Joshi, R. V.; Nelson, C. E.; Poole, K. M.; Skala, M. C.; Duvall, C. L., Dual Ph- and Temperature-Responsive Microparticles for Protein Delivery to Ischemic Tissues. *Acta Biomaterialia* 2013, 9, 6526-6534.
43. Bolte, S.; Cordelieres, F. P., A Guided Tour into Subcellular Colocalization Analysis in Light Microscopy. *J Microsc-Oxford* 2006, 224, 213-232.
44. Kim, D. H.; Behlke, M. A.; Rose, S. D.; Chang, M. S.; Choi, S.; Rossi, J. J., Synthetic Dsrna Dicer Substrates Enhance Rnai Potency and Efficacy. *Nat Biotechnol* 2005, 23, 222-226.
45. Behlke, M. A., Chemical Modification of Sirnas for in Vivo Use. *Oligonucleotides* 2008, 18, 305-319.
46. Judge, A.; MacLachlan, I., Overcoming the Innate Immune Response to Small Interfering Rna. *Hum Gene Ther* 2008, 19, 111-124.
47. Judge, A. D.; Bola, G.; Lee, A. C.; MacLachlan, I., Design of Noninflammatory Synthetic Sirna Mediating Potent Gene Silencing in Vivo. *Mol Ther* 2006, 13, 494-505.
48. Truong, N. P.; Jia, Z.; Burgess, M.; Payne, L.; McMillan, N. A.; Monteiro, M. J., Self-Catalyzed Degradable Cationic Polymer for Release of DNA. *Biomacromolecules* 2011, 12, 3540-3548.
49. Boussif, O.; Lezoualc'h, F.; Zanta, M. A.; Mergny, M. D.; Scherman, D.; Demeneix, B.; Behr, J. P., A versatile vector for gene and oligonucleotide transfer into cells in culture and in vivo: polyethylenimine. *Proc Natl Acad Sci USA* 1995, 92, (16), 7297-301.
50. Chemg, J.-Y.; van de Wetering, P.; Talsma, H.; Crommelin, D. A.; Hennink, W., Effect of Size and Serum Proteins on Transfection Efficiency of Poly ((2-dimethylamino)ethyl Methacrylate)-Plasmid Nanoparticles. *Pharmaceutical Research* 1996, 13, (7), 1038-1042.
51. Wang, S.; Ma, N.; Gao, S. J.; Yu, H.; Leong, K. W., Transgene expression in the brain stem effected by intramuscular injection of polyethylenimine/DNA complexes. *Mol Ther* 2001, 3, (5 Pt 1), 658-64.
52. Kichler, A.; Chillon, M.; Leborgne, C.; Danos, O.; Frisch, B., Intranasal gene delivery with a polyethylenimine-PEG conjugate. *J Control Release* 2002, 81, (3), 379-88.
53. Aoki, K.; Furuhata, S.; Hatanaka, K.; Maeda, M.; Remy, J. S.; Behr, J. P.; Terada, M.; Yoshida, T., Polyethylenimine-mediated gene transfer into pancreatic tumor dissemination in the murine peritoneal cavity. *Gene Ther* 2001, 8, (7), 508-14.
54. Lei, P.; Padmashali, R. M.; Andreadis, S. T., Cell-controlled and spatially arrayed gene delivery from fibrin hydrogels. *Biomaterials* 2009, 30, (22), 3790-9.
55. Trentin, D.; Hubbell, J.; Hall, H., Non-viral gene delivery for local and controlled DNA release. *J Control Release* 2005, 102, (1), 263-75.
56. Lei, Y.; Huang, S.; Sharif-Kashani, P.; Chen, Y.; Kavehpour, P.; Segura, T., Incorporation of active DNA/cationic polymer polyplexes into hydrogel scaffolds. *Biomaterials* 2010, 31, (34), 9106-16.
57. Lei, Y.; Rahim, M.; Ng, Q.; Segura, T., Hyaluronic acid and fibrin hydrogels with concentrated DNA/PEI polyplexes for local gene delivery. *J Control Release* 2011, 153, (3), 255-61.
58. Vader, P.; van der Aa, L. J.; Engbersen, J. F.; Storm, G.; Schiffelers, R. M., Physicochemical and biological evaluation of siRNA polyplexes based on PEGylated Poly (amido amine)s. *Pharm Res* 2012, 29, (2), 352-61.
59. Zhou, J.; Liu, J.; Cheng, C. J.; Patel, T. R.; Weller, C. E.; Piepmeier, J. M.; Jiang, Z.; Saltzman, W. M., Biodegradable poly(amine-co-ester) terpolymers for targeted gene delivery. *Nat Mater* 2012, 11, (1), 82-90.
60. Piest, M.; Engbersen, J. F. J., Effects of charge density and hydrophobicity of poly(amido amine)s for non-viral gene delivery. *Journal of Controlled Release* 2010, 148, (1), 83-90.
61. Lin, M. Y.; Lindsay, H. M.; Weitz, D. A.; Ball, R. C.; Klein, R.; Meakin, P., Universal reaction-limited colloid aggregation. *Phys Rev A* 1990, 41, (4), 41.
62. Oster, C. G.; Wittmar, M.; Unger, F.; Barbu-Tudoran, L.; Schaper, A. K.; Kissel, T., Design of amine-modified graft polyesters for effective gene delivery using DNA-loaded nanoparticles. *Pharm Res* 2004, 21, (6), 927-31.
63. Ogris, M.; Brunner, S.; Schuller, S.; Kircheis, R.; Wagner, E., PEGylated DNA/transferrin-PEI complexes: reduced interaction with blood components, extended circulation in blood and potential for systemic gene delivery. *Gene Ther* 1999, 6, (4), 595-605.
64. Weitz, D. A.; Huang, J. S.; Lin, M. Y.; Sung, J., Limits of the Fractal Dimension for Irreversible Kinetic Aggregation of Gold Colloids. *Phys Rev Lett* 1985, 54, (13), 1416-9.
65. Jiang, D.; Salem, A. K., Optimized dextran-polyethylenimine conjugates are efficient non-viral vectors with reduced cytotoxicity when used in serum containing environments. *Int J Pharm* 2012, 427, (1), 71-9.
66. Dong, X.; Lin, L.; Chen, J.; Guo, Z.; Tian, H.; Li, Y.; Wei, Y.; Chen, X., A serum-tolerant hydroxyl-modified polyethylenimine as versatile carriers of pDNA/siRNA. *Macromol Biosci* 2013, 13, (4), 512-22.
67. Sharma, R.; Lee, J. S.; Bettencourt, R. C.; Xiao, C.; Konieczny, S. F.; Won, Y. Y., Effects of the incorporation of a hydrophobic middle block into a PEG-polycation diblock copolymer on the physicochemical and cell interaction properties of the polymer-DNA complexes. *Biomacromolecules* 2008, 9, (11), 3294-307.
68. Boeckle, S.; Fahrmeir, J.; Roedl, W.; Ogris, M.; Wagner, E., Melittin analogs with high lytic activity at endosomal pH enhance transfection with purified targeted PEI polyplexes. *Journal of Controlled Release* 2006, 112, (2), 240-248.

69. Schellinger, J. G.; Pahang, J. A.; Johnson, R. N.; Chu, D. S. H.; Sellers, D. L.; *Maris*, D. O.; Convertine, A. J.; Stayton, P. S.; Homer, P. J.; Pun, S. H., Melittin-grafted HPMA-oligolysine based copolymers for gene delivery. *Biomaterials* 2013, 34, (9), 2318-2326.

What is claimed is:

1. A nanoparticle, comprising:
   a plurality of polymers that include:
   a first block that includes hydrophilic monomers, the first block substantially forming an outer shell of the nanoparticle; and
   a second block that includes cationic monomers and hydrophobic monomers, the second block substantially forming a core of the nanoparticle; and
   a polynucleotide that is bound to the cationic monomers and substantially located within the core of the nanoparticle.

2. The nanoparticle of claim 1, wherein the hydrophilic monomers include ethylene glycol (EG) monomers.

3. The nanoparticle of claim 2, wherein the ethylene glycol (EG) monomers form a poly(ethylene glycol) including a molecular weight of about 500 Da to about 20,000 Da.

4. The nanoparticle of claim 1, wherein the cationic monomers are cationic at about pH 7.0, at about endosomal pH, or a combination thereof.

5. The nanoparticle of claim 1, wherein the cationic monomers have a greater cationic charge below about pH 7.0 than at about pH 7.0.

6. The nanoparticle of claim 1, wherein the cationic monomers include N,N-di($C_1$-$C_6$)alkyl-amino($C_1$-$C_6$)alkyl-ethacrylate, N,N-di($C_1$-$C_6$)alkyl-amino($C_1$-$C_6$)alkyl-methacrylate, N,N-di($C_1$-$C_6$)alkyl-amino($C_1$-$C_6$)alkyl-acrylate, or combinations thereof.

7. The nanoparticle of claim 1, wherein the cationic monomers include 2-(dimethylamino)ethyl methacrylate (DMAEMA).

8. The nanoparticle of claim 1, wherein the hydrophobic monomers include ($C_2$-$C_8$)alkyl-ethacrylate, ($C_2$-$C_8$)alkyl-methacrylate, ($C_2$-$C_8$)alkyl-acrylate, or combinations thereof.

9. The nanoparticle of claim 8, wherein the hydrophobic monomer includes butyl methacrylate (BMA).

10. The nanoparticle of claim 1, wherein the polynucleotide is electrostatically bound to at least one of the cationic monomers.

11. The nanoparticle of claim 1, wherein the polynucleotide can induce RNAi.

12. The nanoparticle of claim 11, wherein the polynucleotide includes siRNA.

13. The nanoparticle of claim 1, wherein the polynucleotide includes a plasmid.

14. The nanoparticle of claim 1, wherein the plurality of polymers at least partially disassemble at a pH below about pH 7.0.

15. The nanoparticle of claim 14, wherein the plurality of polymers at least partially disassemble at below about pH 6.0.

16. The nanoparticle of claim 14, wherein the plurality of polymers at least partially disassemble at below about pH 5.5.

17. The nanoparticle of claim 1, wherein the plurality of polymers include a polydispersity of about less than 1.10.

18. The nanoparticle of claim 17, wherein the plurality of polymers include a polydispersity of about less than 1.05.

19. The nanoparticle of claim 1, wherein the second block is a diblock copolymer.

20. The nanoparticle of claim 19, wherein:
    the diblock copolymer includes a cationic block and a hydrophobic block,
    the cationic block includes the cationic monomers, and
    the hydrophobic block includes the hydrophobic monomers.

21. The nanoparticle of claim 20, wherein the hydrophobic block links the first block to the cationic block.

22. The nanoparticle of claim 1, wherein the second block comprises about 5 mol % to about 75 mol % of the hydrophobic monomer.

23. The nanoparticle of claim 22, wherein the second block comprises about 10 mol % to about 60 mol % of the hydrophobic monomer.

24. The nanoparticle of claim 22, wherein the second block comprises about 25 mol % to about 50 mol % of the hydrophobic monomer.

25. The nanoparticle of claim 1, wherein a N:P ratio of the nanoparticle is about 0.5 to about 20.

26. The nanoparticle of claim 1, wherein the second block consists essentially of a cationic block that includes the cationic monomers and a hydrophobic block that includes the hydrophobic monomers.

27. The nanoparticle of claim 26, wherein the second block consists of the cationic block that includes the cationic monomers and the hydrophobic block that includes the hydrophobic monomers.

28. The nanoparticle of claim 1, wherein the nanoparticle further comprises a targeting agent.

29. A method for inducing RNAi in a cell, comprising:
    contacting a nanoparticle to the cell, the nanoparticle including:
    a plurality of polymers each comprising a first block that includes hydrophilic monomers, the first block substantially forming an outer shell of the nanoparticle, and a second block that includes cationic monomers and hydrophobic monomers, the second block substantially forming a core of the nanoparticle; and
    a polynucleotide that is bound to the cationic monomers and substantially located within the core of the nanoparticles, the polynucleotide being capable of inducing RNAi in the cell.

30. The method of claim 29, wherein the polynucleotide is capable of inhibiting proliferation of the cell.

31. The method of claim 30, wherein the cell is a cancer cell.

32. The method of claim 29, wherein the hydrophilic monomers include ethylene glycol (EG) monomers.

33. The method of claim 29, wherein the cationic monomers include N,N-di($C_1$-$C_6$)alkyl-amino($C_1$-$C_6$)alkyl-ethacrylate, N,N-di($C_1$-$C_6$)alkyl-amino($C_1$-$C_6$)alkyl-methacrylate, N,N-di($C_1$-$C_6$)alkyl-amino($C_1$-$C_6$)alkyl-acrylate, or combinations thereof.

34. The method of claim 29, wherein the polynucleotide includes siRNA.

35. The method of claim 29, wherein the nanoparticle further comprises a targeting agent specific for the cell.

* * * * *